US009718793B2

(12) United States Patent
Drysdale et al.

(10) Patent No.: US 9,718,793 B2
(45) Date of Patent: *Aug. 1, 2017

(54) ISOXAZOLE COMPOUNDS AS INHIBITORS OF HEAT SHOCK PROTEINS

(71) Applicants: Vernalis (R&D) Limited, Winnersh, Berkshire (GB); Cancer Research Technology Limited, London (GB); The Institute of Cancer Research, London (GB)

(72) Inventors: Martin James Drysdale, Abington (GB); Brian William Dymock, Abington (GB); Harry Finch, Abington (GB); Paul Webb, Abington (GB); Edward McDonald, London (GB); Karen Elizabeth James, London (GB); Kwai Ming Cheung, London (GB); Thomas Peter Matthews, London (GB)

(73) Assignees: Vernalis (R&D) Ltd., Winnersh, Berkshire (GB); Cancer Research Technology Limited, London (GB); The Institute of Cancer Research, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/929,098

(22) Filed: Jun. 27, 2013

(65) Prior Publication Data

US 2013/0289026 A1 Oct. 31, 2013

Related U.S. Application Data

(60) Continuation of application No. 12/708,686, filed on Feb. 19, 2010, now Pat. No. 8,507,480, which is a
(Continued)

(30) Foreign Application Priority Data

Feb. 11, 2003 (GB) .................................. 0303105.1
Mar. 21, 2003 (GB) .................................. 0306560.4
Jun. 13, 2003 (GB) .................................. 0313751.0

(51) Int. Cl.
C07D 261/08 (2006.01)
C07D 261/10 (2006.01)
(Continued)

(52) U.S. Cl.
CPC ......... *C07D 261/08* (2013.01); *C07D 261/10* (2013.01); *C07D 413/04* (2013.01); (Continued)

(58) Field of Classification Search
CPC .. C07D 261/08; C07D 261/10; C07D 495/04; C07D 413/10; C07D 413/04; C07D 417/14
See application file for complete search history.

(56) References Cited

U.S. PATENT DOCUMENTS 6,187,797 B1 * 2/2001 Pruitt et al. ............... 514/340
7,705,027 B2  4/2010 Drysdale et al.
8,507,480 B2 * 8/2013 Drysdale et al. ......... 514/227.8

FOREIGN PATENT DOCUMENTS

EP  1251126  10/2002
JP  2002363079 A  12/2002
(Continued)

OTHER PUBLICATIONS

Yun et al., J. Immunol 2011, 186, 563-575.*
(Continued)

*Primary Examiner* — Sun Jae Yoo
(74) *Attorney, Agent, or Firm* — Banner & Witcoff, Ltd.

(57) ABSTRACT

Isoxazoles of formula (A) or (B) are inhibitors of HSP90 activity, and useful for treatment of, for example cancers:

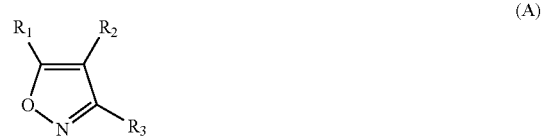

(A)

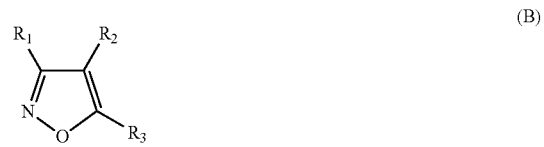

(B)

wherein $R_1$, is a group of formula (IA): —$Ar^1$-$(Alk^1)_p$-$(Z)_r$-$(Alk^2)_s$-Q, wherein in any compatible combination $Ar^1$ is an optionally substituted aryl or heteroaryl radical, $Alk^1$ and $Alk^2$ are optionally substituted divalent $C_1$-$C_6$ alkylene or $C_2$-$C_6$ alkenylene radicals, p, r and s are independently 0 or 1, Z is —O—, —S—, —(C=O)—, —(C=S)—, —$SO_2$—, —C(=O)O—, —C(=O)$NR^4$—, —C(=S)$NR^4$—, —$SO_2NR^4$—, —$NR^4$C(=O)—, —$NR^4SO_2$— or —$NR^4$— wherein $R^4$ is hydrogen or $C_1$-$C_6$ alkyl, and Q is hydrogen or an optionally substituted carbocyclic or heterocyclic radical; $R_2$ is (i) a group of formula (IA) above or (ii) a carboxamide radical; or (iii) a non aromatic carbocyclic or heterocyclic ring wherein a ring carbon is optionally substituted, and/or a ring nitrogen is optionally substituted by a group of formula -$(Alk^1)p$-$(Z)_r$-$(Alk^2)_s$-Q wherein Q, $Alk^1$, $Alk^2$, Z, p, r and s are as defined above in relation to group (IA); and $R_3$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide, or carboxyl ester group.

29 Claims, No Drawings

Related U.S. Application Data division of application No. 10/544,443, filed as application No. PCT/GB2004/000506 on Feb. 9, 2004, now Pat. No. 7,705,027.

(51) Int. Cl.
- *C07D 495/04* (2006.01)
- *C07D 413/10* (2006.01)
- *C07D 413/04* (2006.01)
- *C07D 417/14* (2006.01)
- *C07D 417/04* (2006.01)

(52) U.S. Cl.
CPC ......... *C07D 413/10* (2013.01); *C07D 417/04* (2013.01); *C07D 495/04* (2013.01)

(56) References Cited

FOREIGN PATENT DOCUMENTS

| WO | 9424095 A | 10/1994 |
|----|-----------|---------|
| WO | 00/08001 A | 2/2000 |
| WO | 0112621 | 2/2001 |
| WO | 0112621 A | 2/2001 |

OTHER PUBLICATIONS

Neckers et al., http://www.ncbi.nlm.nih.gov/pmc/articles/PMC3252205/, 2013.*
Naik et al., caplus an 1999:813305.*
Black et al., caplus an 1979:38242.
Newman et al., DDT vol. 8, Oct. 2003, p. 898-90.
Chawla et al., CRIPS vol. 5, No. 1, Jan.-Mar. 2004, p. 9-12.
Fischer et al., Cancer Treatment Reviews 2007, 33, 391-406.
Arbiser, The Journal of Clinical Investigation, 117, 10, 2762-2765.
Madhusudan et al., Clinical Biochemistry, 2004, 37, 618-635.
Tanespimycin (2007); http://www.bio-medicine.org/medicine-technology/Kosan-Presents-Data-on-Lead-Hsp90-Inhibitor-Tanespimycin-Showing-OAPromising-Antitumor-Activity-in-Multiple-Myeloma-at-ASCO-507-1/.
Brough et al., Bioorg Med Chem Lett, 15, 2005, 5197-5201.
Patent Abstracts of Japan, vol. 2003, No. 04, Apr. 2, 2003.
Lisac, caplus an 1977:127275.
Taldone et al., Bioorg. Med. Chem. 19, 2011, 2603-2614.
Zapf et al., Bioorg. Med. Chem. Lett, 21, 2011, 3627-3631.
Gupta, 1998, Main line Signature in Hsp 90 Protein Distinguishing Gram Positive and Gram Negative Bacteria, Abstract.
AUY92, 2013, http://www.vernalis.com/development/nce-pipeline/oncology/auy922.
AT13387, 2013, http://astx.com/pepeline/products/clinical.
Ganetespib, 2013, http://www.syntapharma.com/prdHsp90.aspx.
Pruitt et al., caplus an 1998: 816875.
17-AAG, 2013, http://www.selleckchem.com/products/17-AAG-(Geldanamycin).html.
Kamal, Adeela et al., Therapeutic and diagnostic implications of Hsp90 activation, TRENDS in Molecular Medicine, vol. 10, No. 6, dated Jun. 2004.
Mosser, Dick D., Molecular chaperones and the stress of oncogenesis, Oncogene, vol. 23, pp. 2907-2918, dated 2004.
Workman, Paul, Combinatorial attack on multistep oncogenesis by inhibiting the Hsp90 molecular chaperone, Cancer Letters, vol. 206, pp. 149-157, dated 2004.
Maloney, Alison et al., HSP90 as a new therapeutic target for cancer therapy: the story unfolds, Expert Opin. Biol. Ther., vol. 2(1), pp. 3-24, dated 2002.
Whitesell, Luke, et al., HSP90 and The Chaperoning of Cancer, Nature Reviews, vol. 5, pp. 761-772, dated 2005.

\* cited by examiner

ISOXAZOLE COMPOUNDS AS INHIBITORS OF HEAT SHOCK PROTEINS

CROSS REFERENCE TO RELATED APPLICATIONS

This application is a continuation of U.S. patent application serial number 12/708,686, filed Feb. 19, 2010, now U.S. Pat. No. 8,507,480, which is a divisional of U.S. patent application Ser. No. 10/544,443, filed Apr. 21, 2006, now U.S. Pat. No. 7,705,027, issued Apr. 27, 2010, which is a U.S. National Stage application of co-pending PCT application PCT/GB2004/000506, filed Feb. 9, 2004, which claims the priority of Great Britain Patent Application No. 0303105.1, filed Feb. 11, 2003, Great Britain Patent Application No. 0306560.4, filed Mar. 21, 2003, and Great Britain Patent Application No. 0313751.0, filed Jun. 13, 2003. These applications are incorporated herein by reference in their entireties.

This invention relates to substituted isoxazoles having HSP90 inhibitory activity, to the use of such compounds in medicine, in relation to diseases which are responsive to inhibition of HSP90 activity such as cancers, and to pharmaceutical compositions containing such compounds.

BACKGROUND TO THE INVENTION

Molecular chaperones maintain the appropriate folding and conformation of proteins and are crucial in regulating the balance between protein synthesis and degradation. They have been shown to be important in regulating many important cellular functions, such as cell proliferation and apoptosis (Jolly and Morimoto, 2000; Smith et al., 1998; Smith, 2001).

Heat Shock Proteins (HSPs)

Exposure of cells to a number of environmental stresses, including heat shock, alcohols, heavy metals and oxidative stress, results in the cellular accumulation of a number of chaperones, commonly known as heat shock proteins (HSPs). Induction of HSPs protects the cell against the initial stress insult, enhances recovery and leads to maintenance of a stress tolerant state. It has also become clear, however, that certain HSPs may also play a major molecular chaperone role under normal, stress-free conditions by regulating the correct folding, degradation, localization and function of a growing list of important cellular proteins.

A number of multigene families of HSPs exist, with individual gene products varying in cellular expression, function and localization. They are classified according to molecular weight, e.g., HSP70, HSP90, and HSP27. Several diseases in humans can be acquired as a result of protein misfolding (reviewed in Tytell et al., 2001; Smith et al., 1998). Hence the development of therapies which disrupt the molecular chaperone machinery may prove to be beneficial. In some conditions (e.g., Alzheimer's disease, prion diseases and Huntington's disease), misfolded proteins can cause protein aggregation resulting in neurodegenerative disorders. Also, misfolded proteins may result in loss of wild type protein function, leading to deregulated molecular and physiological functions in the cell.

HSPs have also been implicated in cancer. For example, there is evidence of differential expression of HSPs which may relate to the stage of tumour progression (Martin et al., 2000; Conroy et al., 1996; Kawanishi et al., 1999; Jameel et al., 1992; Hoang et al., 2000; Lebeau et al., 1991). As a result of the involvement of HSP90 in various critical oncogenic pathways and the discovery that certain natural products with anticancer activity are targeting this molecular chaperone, the fascinating new concept has been developed that inhibiting HSP function may be useful in the treatment of cancer. The first molecular chaperone inhibitor is currently undergoing clinical trials.

HSP90

HSP90 constitutes about 1-2% of total cellular protein, and is usually present in the cell as a dimer in association with one of a number of other proteins (see, e.g., Pratt, 1997). It is essential for cell viability and it exhibits dual chaperone functions (Young et al., 2001). It plays a key role in the cellular stress response by interacting with many proteins after their native conformation has been altered by various environmental stresses, such as heat shock, ensuring adequate protein folding and preventing non-specific aggregation (Smith et al., 1998). In addition, recent results suggest that HSP90 may also play a role in buffering against the effects of mutation, presumably by correcting the inappropriate folding of mutant proteins (Rutherford and Lindquist, 1998). However, HSP90 also has an important regulatory role. Under normal physiological conditions, together with its endoplasmic reticulum homologue GRP94, HSP90 plays a housekeeping role in the cell, maintaining the conformational stability and maturation of several key client proteins. These can be subdivided into three groups: (a) steroid hormone receptors, (b) Ser/Thr or tyrosine kinases (e.g., ERBB2, RAF-1, CDK4, and LCK), and (c) a collection of apparently unrelated proteins, e.g., mutant p53 and the catalytic subunit of telomerase hTERT. All of these proteins play key regulatory roles in many physiological and biochemical processes in the cell. New HSP90 client proteins are continuously being identified.

The highly conserved HSP90 family in humans consists of four genes, namely the cytosolic HSP90α and HSP90β isoforms (Hickey et al., 1989), GRP94 in the endoplasmic reticulum (Argon et al., 1999) and HSP75/TRAP1 in the mitochondrial matrix (Felts et al., 2000). It is thought that all the family members have a similar mode of action, but bind to different client proteins depending on their localization within the cell. For example, ERBB2 is known to be a specific client protein of GRP94 (Argon et al., 1999) and type 1 tumour necrosis factor receptor (TNFR1) and RB have both been shown to be clients of TRAP1 (Song et al., 1995; Chen et al., 1996).

HSP90 participates in a series of complex interactions with a range of client and regulatory proteins (Smith, 2001). Although the precise molecular details remain to be elucidated, biochemical and X-ray crystallographic studies (Prodromou et al., 1997; Stebbins et al., 1997) carried out over the last few years have provided increasingly detailed insights into the chaperone function of HSP90.

Following earlier controversy on this issue, it is now clear that HSP90 is an ATP-dependent molecular chaperone (Prodromou et al, 1997), with dimerization of the nucleotide binding domains being essential for ATP hydrolysis, which is in turn essential for chaperone function (Prodromou et al, 2000a). Binding of ATP results in the formation of a toroidal dimer structure in which the N terminal domains are brought into closer contact with each other resulting in a conformational switch known as the 'clamp mechanism' (Prodromou and Pearl, 2000b).

Known HSP90 Inhibitors

The first class of HSP90 inhibitors to be discovered was the benzoquinone ansamycin class, which includes the compounds herbimycin A and geldanamycin. They were shown to reverse the malignant phenotype of fibroblasts transformed by the v-Src oncogene (Uehara et al., 1985), and subsequently to exhibit potent antitumour activity in both in vitro (Schulte et al., 1998) and in vivo animal models (Supko et al., 1995).

Immunoprecipitation and affinity matrix studies have shown that the major mechanism of action of geldanamycin involves binding to HSP90 (Whitesell et al., 1994; Schulte and Neckers, 1998). Moreover, X-ray crystallographic studies have shown that geldanamycin competes at the ATP binding site and inhibits the intrinsic ATPase activity of HSP90 (Prodromou et al., 1997; Panaretou et al., 1998). This in turn prevents the formation of mature multimeric HSP90 complexes capable of chaperoning client proteins. As a result, the client proteins are targeted for degradation via the ubiquitin proteasome pathway. 17-Allylamino, 17-demethoxygeldanamycin (17AAG) retains the property of HSP90 inhibition resulting in client protein depletion and antitumour activity in cell culture and xenograft models (Schulte et al, 1998; Kelland et al, 1999), but has significantly less hepatotoxicity than geldanamycin (Page et al, 1997). 17AAG is currently being evaluated in Phase I clinical trials.

Radicicol is a macrocyclic antibiotic shown to reverse the malignant phenotype of v-Src and v-Ha-Ras transformed fibroblasts (Kwon et al, 1992; Zhao et al, 1995). It was shown to degrade a number of signalling proteins as a consequence of HSP90 inhibition (Schulte et al., 1998). X-ray crystallographic data confirmed that radicicol also binds to the N terminal domain of HSP90 and inhibits the intrinsic ATPase activity (Roe et al., 1998). Radicicol lacks antitumour activity in vivo due to the unstable chemical nature of the compound.

Coumarin antibiotics are known to bind to bacterial DNA gyrase at an ATP binding site homologous to that of the HSP90. The coumarin, novobiocin, was shown to bind to the carboxy terminus of HSP90, i.e., at a different site to that occupied by the benzoquinone ansamycins and radicicol which bind at the N-terminus (Marcu et al., 2000b). However, this still resulted in inhibition of HSP90 function and degradation of a number of HSP90-chaperoned signalling proteins (Marcu et al., 2000a). Geldanamcyin cannot bind HSP90 subsequent to novobiocin; this suggests that some interaction between the N and C terminal domains must exist and is consistent with the view that both sites are important for HSP90 chaperone properties.

A purine-based HSP90 inhibitor, PU3, has been shown to result in the degradation of signalling molecules, including ERBB2, and to cause cell cycle arrest and differentiation in breast cancer cells (Chiosis et al., 2001).

HSP90 as a Therapeutic Target

Due to its involvement in regulating a number of signalling pathways that are crucially important in driving the phenotype of a tumour, and the discovery that certain bioactive natural products exert their effects via HSP90 activity, the molecular chaperone HSP90 is currently being assessed as a new target for anticancer drug development (Neckers et al., 1999).

The predominant mechanism of action of geldanamycin, 17AAG, and radicicol involves binding to HSP90 at the ATP binding site located in the N-terminal domain of the protein, leading to inhibition of the intrinsic ATPase activity of HSP90 (see, e.g., Prodromou et al., 1997; Stebbins et al., 1997; Panaretou et al., 1998).

Inhibition of HSP90 ATPase activity prevents recruitment of co-chaperones and encourages the formation of a type of HSP90 heterocomplex from which these client proteins are targeted for degradation via the ubiquitin proteasome pathway (see, e.g., Neckers et al., 1999; Kelland et al., 1999).

Treatment with HSP90 inhibitors leads to selective degradation of important proteins involved in cell proliferation, cell cycle regulation and apoptosis, processes which are fundamentally important in cancer.

Inhibition of HSP90 function has been shown to cause selective degradation of important signalling proteins involved in cell proliferation, cell cycle regulation and apoptosis, processes which are fundamentally important and which are commonly deregulated in cancer (see, e.g., Hostein et al., 2001). An attractive rationale for developing drugs against this target for use in the clinic is that by simultaneously depleting proteins associated with the transformed phenotype, one may obtain a strong antitumour effect and achieve a therapeutic advantage against cancer versus normal cells. These events downstream of HSP90 inhibition are believed to be responsible for the antitumour activity of HSP90 inhibitors in cell culture and animal models (see, e.g., Schulte et al., 1998; Kelland et al., 1999).

BRIEF DESCRIPTION OF THE INVENTION

The present invention relates to the use of a class of substituted isoxazole compounds as HSP90 inhibitors; for example for inhibition of cancer cell proliferation. The invention also includes novel isoxazole compounds per se, and pharmaceutical compositions containing them

DETAILED DESCRIPTION OF THE INVENTION

According to the present invention there is provided the use of a compound of formula (A) or (B) or a salt, N-oxide, hydrate or solvate thereof, or a prodrug thereof, in the preparation of a composition for inhibition of HSP90 activity:

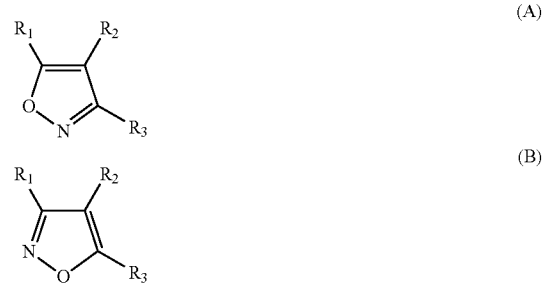

wherein
R$_1$ is a group of formula (IA):

$$—Ar^1-(Alk^1)_p-(Z)_r-(Alk^2)_s-Q \qquad (IA)$$

wherein in any compatible combination
Ar$^1$ is an optionally substituted aryl or heteroaryl radical,
Alk$^1$ and Alk$^2$ are optionally substituted divalent C$_1$-C$_6$ alkylene or C$_2$-C$_6$ alkenylene radicals,
p, r and s are independently 0 or 1,
Z is —O—, —S—, —(C=O)—, —(C=S)—, —SO$_2$—, —C(=O)O—, —C(=O)NR$^A$—, —C(=S)NR$^A$—, —SO$_2$NR$^A$—, —NR$^A$C(=O)—, —NR$^A$SO$_2$— or —NR$^A$— wherein R$^A$ is hydrogen or C$_1$-C$_6$ alkyl, and Q is hydrogen or an optionally substituted carbocyclic or heterocyclic radical;

$R_2$ is (i) a group of formula (IA) as defined in relation to $R_1$;

(ii) a carboxamide radical; or (iii) a non aromatic carbocyclic or heterocyclic ring wherein a ring carbon is optionally substituted, and/or a ring nitrogen is optionally substituted by a group of formula -(Alk$^1$)$_p$-(Z)$_r$-(Alk$^2$)$_s$-Q wherein Q, Alk$^1$, Alk$^2$, Z, p, r and s are as defined above in relation to group (IA); and $R_3$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide, or carboxyl ester group.

In general, the class of compounds defined above in relation to formula (I) is believed to be novel, and the invention includes all novel members of that class and their salts, hydrates and solvates, and prodrugs thereof.

As used herein:

the term "carboxyl group" refers to a group of formula —COOH;

the term "carboxyl ester group" refers to a group of formula —COOR, wherein R is a radical actually or notionally derived from the hydroxyl compound ROH; and the term "carboxamide group" refers to a group of formula —CONR$_a$R$_b$, wherein —NR$_a$R$_b$ is a primary or secondary (including cyclic) amino group actually or notionally derived from ammonia or the amine HNR$_a$R$_b$.

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein, the term "($C_a$-$C_b$)alkenyl" wherein a and b are integers refers to a straight or branched chain alkenyl radical having from a to b carbon atoms and containing at least one double bond of E or Z configuration, including for example, ethenyl and allyl.

As used herein the term "divalent ($C_a$-$C_b$)alkenylene radical" wherein a and b are integers refers to a hydrocarbon chain having from a to b carbon atoms, at least one double bond, and two unsatisfied valences.

As used herein, the term "($C_a$-$C_b$)alkynyl" wherein a and b are integers refers to a straight or branched chain alkenyl radical having from a to b carbon atoms and containing at least one triple bond, including for example, ethynyl and prop-2-ynyl.

As used herein, the term "divalent ($C_a$-$C_b$)alkynylene radical" wherein a and b are integers refers to a straight or branched chain alkynyl radical having from a to b carbon atoms and containing at least one triple bond, and two unsatisfied valencies.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "aryl" refers to a mono-, bi- or tri-cyclic carbocyclic aromatic radical. Illustrative of such radicals are phenyl, biphenyl and napthyl.

As used herein the term "carbocyclic" refers to a cyclic radical whose ring atoms are all carbon, and includes monocyclic aryl, cycloalkyl and cycloalkenyl radicals.

As used herein the term "heteroaryl" refers to a mono-, bi- or tri-cyclic aromatic radical containing one or more heteroatoms selected from S, N and O. Illustrative of such radicals are thienyl, benzothienyl, furyl, benzofuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$)alkyl, ($C_1$-$C_6$)alkoxy, hydroxy, hydroxy($C_1$-$C_6$) alkyl, mercapto, mercapto($C_1$-$C_6$)alkyl, ($C_1$-$C_6$)alkylthio, halo (including fluoro, bromo and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a ($C_1$-$C_6$)alkyl group. An "optional substituent" may be one of the foregoing substituent groups. Of the above substituents, ($C_1$-$C_6$)alkyl, halo, trifluoromethyl, trifluoromethoxy, trifluoromethylsulfonyl, and phenyl are those most commonly regarded as lipophilic. Other substituents listed which contain alkyl groups may be lipophilic depending on the particular alkyl groups present.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, be4nzoic, benzenesulfonic, glutamic, lactic, and mandelic acids and the like.

The term "lipophilic" as used herein in relation to a substituent means that it has a positive substituent hydrophobicity constant (π). (A positive value for π indicates that the substituent is more lipophilic than hydrogen, whereas a negative value indicates it is less lipophilic, i.e. more hydrophilic, than hydrogen).

Some compounds of the invention contain one or more actual or potential chiral centres because of the presence of asymmetric carbon atoms. The presence of several asymmetric carbon atoms gives rise to a number of diastereoisomers with R or S stereochemistry at each chiral centre. The invention includes all such diastereoisomers and mixtures thereof.

An aspect of the invention includes compounds of formula (A) or (B) above and a salts, N-oxides, hydrates or solvates thereof and prodrugs thereof, except the following three compounds (X), (Y) and (Z) which are commercially available:

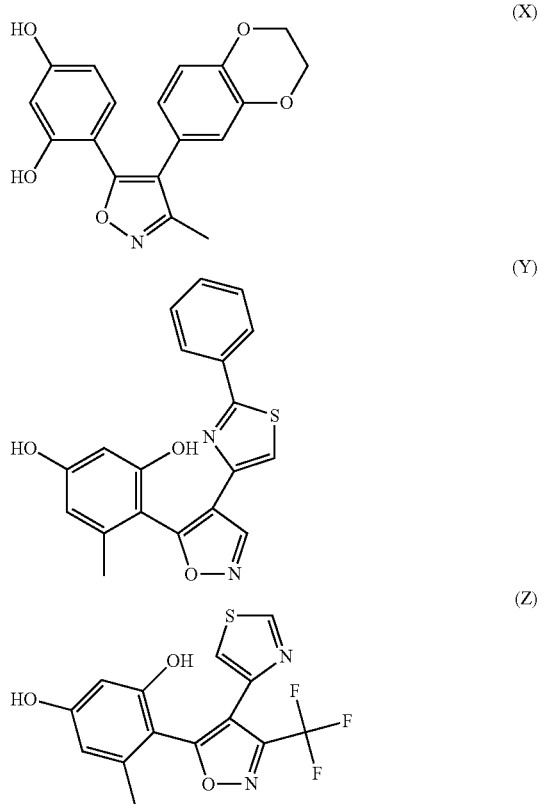

Subject to those exclusions, the invention particularly includes those wherein the substituents $R_1$, $R_2$ and $R_3$ are as discussed and specified in the following sections headed "The radical $R_1$", "The radical $R_2$", and "The radical $R_3$". Another aspect includes the use of such compounds for the treatment of diseases responsive to inhibition of HSP90 activity.

The Radical $R_1$

In general, it is currently preferred that the radical $Ar^1$ present in the $R_1$ group is optionally substituted phenyl, preferably with one of the optional substituents being a hydroxy group in position 2 relative to the point of attachment of the phenyl ring to isoxazole ring. In other words, the group $R_1$ preferably has formula (IB)

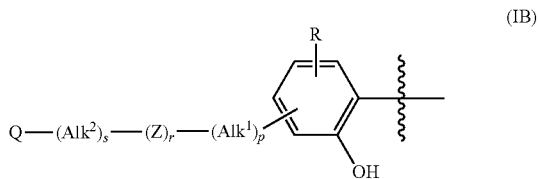

wherein $Alk^1$, $Alk^2$, p, r, s, Z and Q are as defined above in relation to $R_1$, and R represents one or more optional substituents. In such structures, it is further preferred that the ring carbon atom adjacent the hydroxyl group be unsubstituted. In the further discussion of $R_1$ which follows, this preference applies in addition to any other possibilities mentioned.

In the simplest structures with which the invention is concerned, each of p, r and s may be 0, and Q may be hydrogen, so that $R_1$ is optionally substituted aryl or heteroaryl. In such cases, $R_1$ may be, for example, optionally substituted phenyl, preferably 2-hydroxyphenyl which may be further substituted, for example by one or more of hydroxy, methyl, ethyl, methoxy, ethoxy, chloro, or bromo. Currently preferred are compounds wherein $R_1$ is 2,4-dihydroxyphenyl, substituted in the 5-position by a small lipophilic substituent, for example having a molecular volume equal to or less than that of tert-butyl, such as methyl, ethyl, isopropyl, isobutyl, tert-butyl, chloro, or bromo, especially ethyl, isopropyl, or chloro. In such 5-substituted, 2,4-dihydroxy phenyl compounds of the invention, the hydroxyl groups may be protected by groups which are cleaved in the body to release the hydroxyl groups. Known prodrug-type groups of this kind which are cleaved to hydroxyls include alkylcarbonyloxy groups such as methylcarbonyloxy, and alkylaminocarbonyloxy groups such as dialkylamino- or isopropylamino-carbonyloxy.

In other simple structures with which the invention is concerned, p, r and s may again each be 0, and Q may be an optionally substituted carbocyclic or heterocyclic ring, for example a phenyl or pyridyl ring. In such cases, Q is a direct substituent in the optionally substituted $Ar^1$ ring In more complex structures with which the invention is concerned, one or more of p, r and s may be 1, and Q may be hydrogen or an optionally substituted carbocyclic or heterocyclic ring. For example, p and/or s may be 1 and r may be 0, so that Q is linked to $Ar^1$ by an alkylene or alkenylene radical, for example a $C_1$-$C_3$ alkylene radical, which is optionally substituted. In other cases each of p, r, and s may be 1, in which cases, Q is linked to $Ar^1$ by an alkylene or alkenylene radical which is interrupted by the hetero atom-containing Z radical. In still other cases, p and s may be 0 and r may be 1, in which case Q is linked to $Ar^1$ via the hetero atom-containing Z radical.

Specific examples of $R_1$ groups of the above types are present in the compounds of the Examples herein.

The Radical $R_2$

When $R_2$ is of type (i), i.e. a group of formula (IA), examples include phenyl, 2-, 3-, or 4-pyridyl, 2- or 3-furanyl, 2- or 3-thienyl, and thiazolyl wherein optional substituents include any of those listed above in the definition of "substituted", for example methoxy, ethoxy, methylenedioxy, ethylenedioxy, fluoro, chloro, bromo, and trifluoromethyl. For example $R_2$ may be phenyl substituted in the 4 position by $C_1$-$C_6$ alkoxy such as methoxy or ethoxy, or by fluoro, chloro, bromo, piperazinyl, N-methylpiperazinyl, or piperidinyl.

Presently preferred $R_2$ substituents include those having the partial structure:

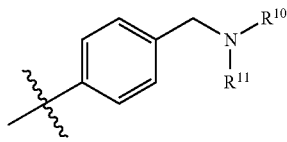

wherein the substituted amino group —$NR^{10}R^{11}$ is a solubilising group. Many such solubilising groups are known in medicinal chemistry. Examples include morpholinyl, piperidinyl, piperazinyl, pyrrolidinyl, ethylamino, isopropylamino, diethylamino, cyclohexylamino, cyclopentylamino, methoxyethylamino, piperidin-4-yl, N-acetylpiperazinyl, methylsulfonylamino, thiomorpholinyl, thiomorpholinyldioxide, 4-hydroxyethylpiperidinyl, and 4-hydroxypiperidinyl.

Our copending international patent application no. PCT/GB2003/005275 discloses HSP90 inhibiting pyrazole compounds analogous to the isoxazoles with which this invention is concerned, and which are believed to bind to the HSP90 target in an analogous fashion. Those pyrazole compounds have a carboxamide group in the position corresponding to $R_2$ of the present isoxazoles. Hence, when $R_2$ in the present isoxazoles is a carboxamide radical of type (ii) above, examples include those present in the pyrazole compounds of PCT/GB2003/005275, for example carboxamides of formula —$CONR^B(Alk)_nR^A$ wherein Alk is a divalent alkylene, alkenylene or alkynylene radical, for example a —$CH_2$—, —$CH_2CH_2$—, —$CH_2CH_2CH_2$—, —$CH_2CH=CH$—, or —$CH_2CCCH_2$-radical, and the Alk radical may be optionally substituted, n is 0 or 1, $R^B$ is hydrogen or a $C_1$-$C_6$ alkyl or $C_2$-$C_6$ alkenyl group, for example methyl, ethyl, n- or iso-propyl, or allyl, $R^A$ is hydroxy or optionally substituted carbocyclic, for example hydroxy and/or chloro-substituted phenyl and 3,4 methylenedioxyphenyl; or heterocyclyl, for example pyridyl, furyl, thienyl, N-piperazinyl, or N-morpholinyl any of which heterocyclic rings may be substituted, or $R^A$ and $R^B$ taken together with the nitrogen to which they are attached form an N-heterocyclic ring which may optionally contain one or more additional hetero atoms selected from O, S and N, and which may optionally be substituted on one or more ring C or N atoms, examples of such N-heterocyclic rings including morpholino, piperidinyl, piperazinyl and N-phenylpiperazinyl.

The Radical $R_3$ $R_3$ may be, for example, hydrogen, methyl, ethyl, n- or iso-propyl, trifluoromethyl, hydroxyethyl, methylsulfonaminomethyl, or a carboxamide group —$CONR^B(Alk)_nR^A$ as discussed above for $R_2$. A carboxamide group is presently preferred, especially ethylaminocarbonyl and isopropylaminocarbonyl.

A particular sub-set of the compounds with which this invention is concerned consists of those of formula (ID), and the formula B regioisomers thereof, and their salts, solvates and hydrates, and prodrugs thereof:

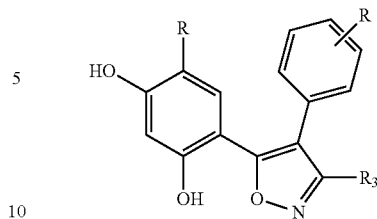

(ID)

wherein each R independently represents an optional substituent and $R^3$ represents a carboxamide group.

A preferred sub-set of the compounds with which this invention is concerned consists of those of formula (IE), and the formula (B) regioisomers thereof, and their salts, solvates and hydrates, and prodrugs thereof:

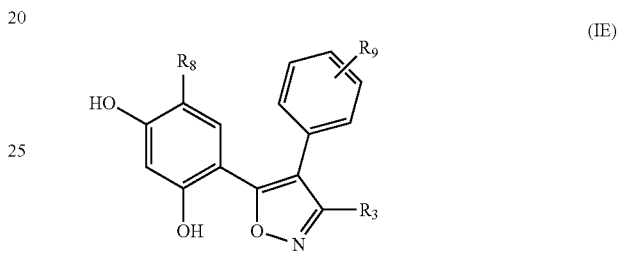

(IE)

wherein $R_3$ represents a carboxamide group (such as ethylaminocarbonyl $CH_3CH_2NHC(=O)$—, or isopropylaminocarbonyl $(CH_3)_2CHNHC(=O)$—); $R_9$ represents —$CH_2NR^{10}R^{11}$ or —$NR^{10}R^{11}$ wherein the substituted amino group —$NR^{10}R^{11}$ is a solubilising group, (such as morpholinyl, piperidinyl, piperazinyl, pyrrolidinyl, ethylamino, isopropylamino, diethylamino, cyclohexylamino, cyclopentylamino, methoxyethylamino, piperidin-4-yl, N-acetylpiperazinyl, N-methylpiperazinyl, methylsulfonylamino, thiomorpholinyl, thiomorpholinyl-dioxide, 4-hydroxyethylpiperidinyl, and 4-hydroxypiperidinyl); and $R_8$ represents an optional substituent, especially a small lipophilic group (such as ethyl, isopropyl, bromo, or chloro).

Specific compounds with which the invention is concerned include those of the Examples, particularly the following, and their salts, N-oxides, hydrates and solvates, and prodrugs thereof:

5-(2,4-Dihydroxy-5-isopropyl-phenyl)-4-(4-morpholin-4-ylmethyl-phenyl)-isoxazole-3-carboxylic acid ethylamide 5-(2,4-Dihydroxy-5-isopropyl-phenyl)-4-(4-piperidin-1-ylmethyl-phenyl)-isoxazole-3-carboxylic acid ethylamide 4-(4-Diethylaminomethyl-phenyl)-5-(2,4-dihydroxy-5-isopropyl-phenyl)-isoxazole-3-carboxylic acid ethylamide 5-(2,4-Dihydroxy-5-isopropyl-phenyl)-4-[4-(4-methyl-piperazin-1-ylmethyl)-phenyl]-isoxazole-3-carboxylic acid ethylamide 5-(2,4-Dihydroxy-5-isopropyl-phenyl)-4-(4-ethylaminomethyl-phenyl)-isoxazole-3-carboxylic acid ethylamide 5-(2,4-Dihydroxy-5-isopropyl-phenyl)-4-[4-(isopropylamino-methyl)-phenyl]-isoxazole-3-carboxylic acid ethylamide 4-(4-Cyclohexylaminomethyl-phenyl)-5-(2,4-dihydroxy-5-isopropyl-phenyl)-isoxazole-3-carboxylic acid ethylamide 4-[4-(tert-Butylamino-methyl)-phenyl]-5-(2,4-dihydroxy-5-isopropyl-phenyl)-isoxazole-3-carboxylic acid ethylamide 5-(2,4-Dihydroxy-5-isopropyl-phenyl)-4-{4-[(2-methoxy-ethylamino)-methyl]-phenyl}-isoxazole-3-carboxylic acid ethylamide
5-(2,4-Dihydroxy-5-isopropyl-phenyl)-4-(4-morpholin-4-ylmethyl-phenyl)-isoxazole-3-carboxylic acid isopropylamide
5-(2,4-Dihydroxy-5-isopropyl-phenyl)-4-[4-(4-methyl-piperazin-1-ylmethyl)-phenyl]-isoxazole-3-carboxylic acid isopropylamide
5-(5-tert-Butyl-2,4-dihydroxy-phenyl)-4-[4-(4-methyl-piperazin-1-ylmethyl)-phenyl]-isoxazole-3-carboxylic acid ethylamide
5-(5-tert-Butyl-2,4-dihydroxy-phenyl)-4-(4-piperidin-1-ylmethyl-phenyl)-isoxazole-3-carboxylic acid ethylamide
5-(2,4-Dihydroxy-5-isobutyl-phenyl)-4-(4-morpholin-4-ylmethyl-phenyl)-isoxazole-3-carboxylic acid ethylamide
5-(2,4-Dihydroxy-5-isobutyl-phenyl)-4-(4-piperidin-1-ylmethyl-phenyl)-isoxazole-3-carboxylic acid ethylamide
5-(5-tert-Butyl-2,4-dihydroxy-phenyl)-4-(4-morpholin-4-ylmethyl-phenyl)-isoxazole-3-carboxylic acid ethyl amide
5-(5-tert-Butyl-2,4-dihydroxy-phenyl)-4-(4-diethylaminomethyl-phenyl)-isoxazole-3-carboxylic acid ethylamide
3-(5-Chloro-2,4-dihydroxy-phenyl)-4-(4-morpholin-4-ylmethyl-phenyl)-isoxazole-5-carboxylic acid ethylamide
4-(4-Diethylaminomethyl-phenyl)-5-(4,6-dihydroxy-2'-methyl-biphenyl-3-yl)-isoxazole-3-carboxylic acid ethylamide
4-(4-Diethylaminomethyl-phenyl)-5-(4'-fluoro-4,6-dihydroxy-biphenyl-3-yl)-isoxazole-3-carboxylic acid ethylamide
4-(4-Diethylaminomethyl-phenyl)-5-(4,6-dihydroxy-biphenyl-3yl)-isoxazole-3-carboxylic acid ethylamide
5-(2'-Fluoro-4,6-dihydroxy-biphenyl-3-yl)-4-(4-pyrrolidin-1-ylmethyl-phenyl)-isoxazole-3-carboxylic acid ethylamide
5-(4,6-Dihydroxy-biphenyl-3-yl)-4-(4-morpholin-4-ylmethyl-phenyl)-isoxazole-3-carboxylic acid ethylamide
5-(2,4-Dihydroxy-5-phenethyl-phenyl)-4-(4-morpholin-4-ylmethyl-phenyl)-isoxazole-3-carboxylic acid ethylamide
5-(5-Chloro-2,4-dihydroxy-phenyl)-4-(4-piperidin-1-ylmethyl-phenyl)-isoxazole-3-carboxylic acid isopropylamide
4-(4-Diethylaminomethyl-phenyl)-5-(5-ethyl-2,4-dihydroxy-phenyl)-isoxazole-3-carboxylic acid ethylamide
5-(5-Ethyl-2,4-dihydroxy-phenyl)-4-[4-(4-methyl-piperazin-1-ylmethyl)-phenyl]-isoxazole-3-carboxylic acid ethylamide
5-(5-Ethyl-2,4-dihydroxy-phenyl)-4-(4-morpholin-4-ylmethyl-phenyl)-isoxazole-3-carboxylic acid ethylamide
5-(5-Chloro-2,4-dihydroxy-phenyl)-4-(4-diethylaminomethyl-phenyl)-isoxazole-3-carboxylic acid ethylamide
5-(5-Chloro-2,4-dihydroxy-phenyl)-4-[4-(4-methyl-piperazin-1-ylmethyl)-phenyl]-isoxazole-3-carboxylic acid ethylamide
5-(5-Chloro-2,4-dihydroxy-phenyl)-4-(4-morpholin-4-ylmethyl-phenyl)-isoxazole-3-carboxylic acid ethylamide Compounds with which the invention is concerned may be prepared by literature methods, such as those of the preparative Examples herein, and methods analogous thereto.

For example, some compounds of formula (IA) may be prepared by reaction of hydroxylamine and a compound of formula (III),

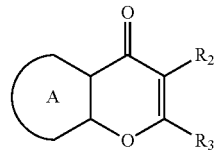

wherein ring A corresponds to the group $R_1$ of compounds (IA) and $R_2$ and $R_3$ are as defined in relation to formula (I). Compounds prepared in this way may then be chemically modified to introduce desired substituents, to produce other compounds of formula (A) For example where $R_1$ is a phenyl ring, optionally already carrying substituents, the introduction of a bromo substituent will often enable introduction of other substituents at the bromo site by sp2 coupling.

In another route to some compounds of formula (A), the isoxazole ring is formed by the reaction of a compound (IV) with hydroxylamine

wherein $R'_1$ and $R'_3$ are members of the substituent classes $R_1$ and $R_3$ defined above, to produce the isoxazole (V)

followed by introduction of the additional substituent $R_2$ (for example by bromination or iodination of the ring carbon in (V) and sp2 coupling, and/or modification of the resultant $R'_1$, $R'_3$ and $R_2$ substituents of the isoxazole.

Furthermore, some isoxazole regioisomers (B) may be prepared from the isoxazoles (A) by reaction with trimethyloxonium boron trifluoride, and again compounds prepared in this way may then be chemically modified to introduce desired substituents, to produce other compounds of formula (IA).

It will be understood that during the above syntheses, it may be desirable to protect any reactive groups such as hydroxyls, and to deprotect later. Further synthetic details are described in the examples herein.

The compounds of the invention are inhibitors of HSP90 and are thus useful in the treatment of diseases which are responsive to inhibition of HSP90 activity such as cancers; viral diseases such as Hepatitis C(HCV) (Waxman, 2002); Immunosupression such as in transplantation (Bijlmakers, 2000 and Yorgin, 2000); Anti-inflammatory diseases (Bucci, 2000) such as Rheumatoid arthritis, Asthma, MS, Type I Diabetes, Lupus, Psoriasis and Inflammatory Bowel Disease; Cystic fibrosis (Fuller, 2000); Angiogenesis-related diseases (Hur, 2002 and Kurebayashi, 2001): diabetic retinopathy, haemangiomas, psoriasis, endometriosis and tumour angiogenesis. Also an Hsp90 inhibitor of the invention may protect normal cells against chemotherapy-induced toxicity and be useful in diseases where failure to undergo apoptosis is an underlying factor. Such an Hsp90 inhibitor may also be useful in diseases where the induction of a cell stress or heat shock protein response could be beneficial, for example, protection from hypoxia-ischemic injury due to elevation of Hsp70 in the heart (Hutter, 1996 and Trost, 1998) and brain (Plumier, 1997 and Rajder, 2000). An Hsp900 inhibitor could also be useful in diseases where protein misfolding or aggregation is a major causal factor, for example, scrapie/CJD, Huntingdon's and Alzheimer's (Sittler, 2001; Trazelt, 1995 and Winklhofer, 2001).

Accordingly, the invention also provides:
(i) a method of treatment of diseases or conditions responsive to inhibition of HSP90 activity in mammals, particularly humans, which method comprises administering to the mammal an amount of a compound of formula (A) or (B) as defined above, or a salt, hydrate or solvate thereof, effective to inhibit said HSP90 activity; and
(ii) a compound of formula (A) or (B) as defined above, or a salt hydrate or solvate thereof, for use in human or veterinary medicine, particularly in the treatment of diseases or conditions responsive to inhibition of HSP90 activity;
(iii) a pharmaceutical composition comprising a compound of formula (A) or (B) as defined and specified above, together with a pharmaceutically acceptable carrier. In particular, the invention includes a solution or suspension of such compound in a sterile, physiologically acceptable carrier, for example aqueous saline.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants, such as a local anaesthetic, preservative and buffering agents, can be dissolved in the vehicle.

Compounds of the invention are also useful in in vitro assays dependent on inhibition of HSP90 activity, for example in screening for alternative classes of HSP90 inhibitors wherein the test compound competes with or displaces a compound of this invention. Accordingly, in yet another aspect, the invention includes a method of inhibiting HSP90 activity, comprising bringing into contact, in vitro, an HSP90 enzyme and a compound of formula (A) or (B) as defined and specified above.

The following examples illustrate the preparation and activities of specific compounds of the invention.

Examples 1-4

Scheme 1: preparation of bromo intermediate and subsequent arylation

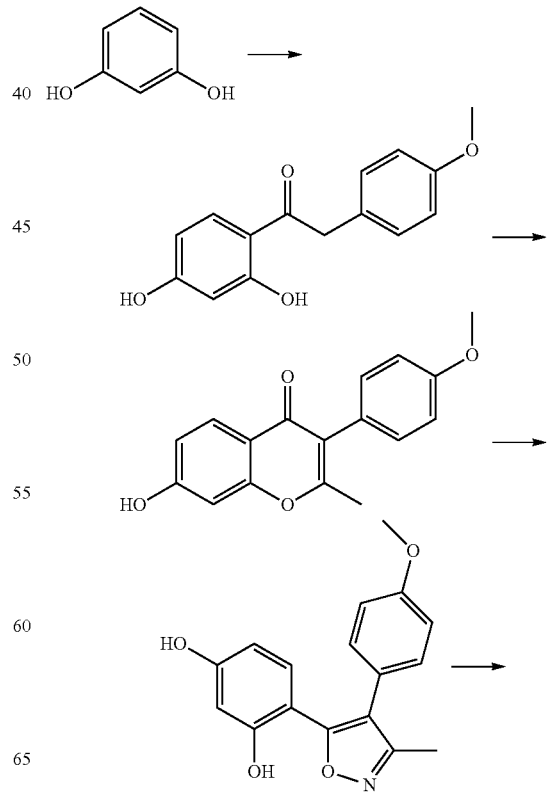

-continued

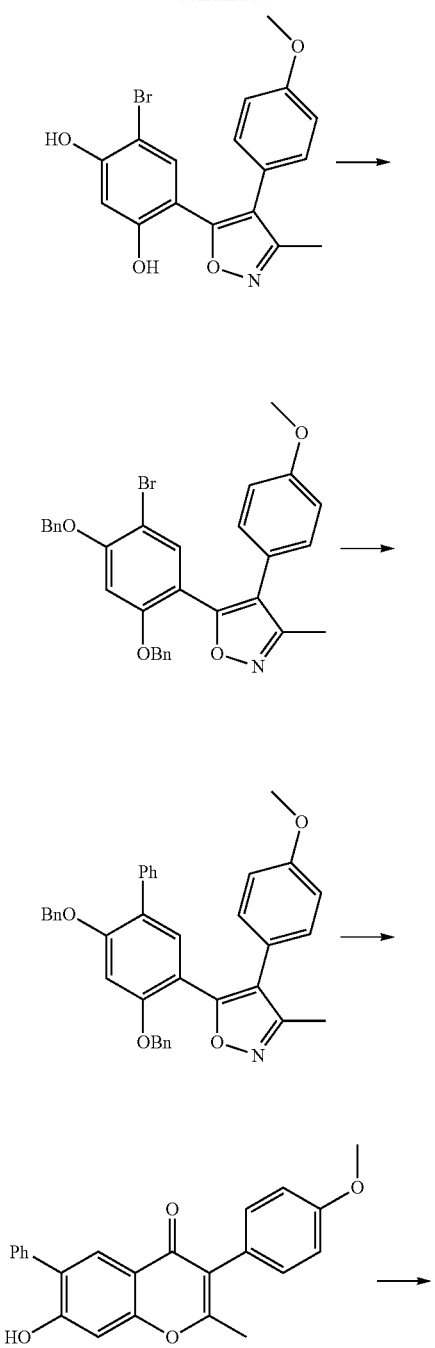

Example 1

4-[4-(4-Methoxy-phenyl)-3-methyl-isoxazol-5-yl]-benzene-1,3-diol

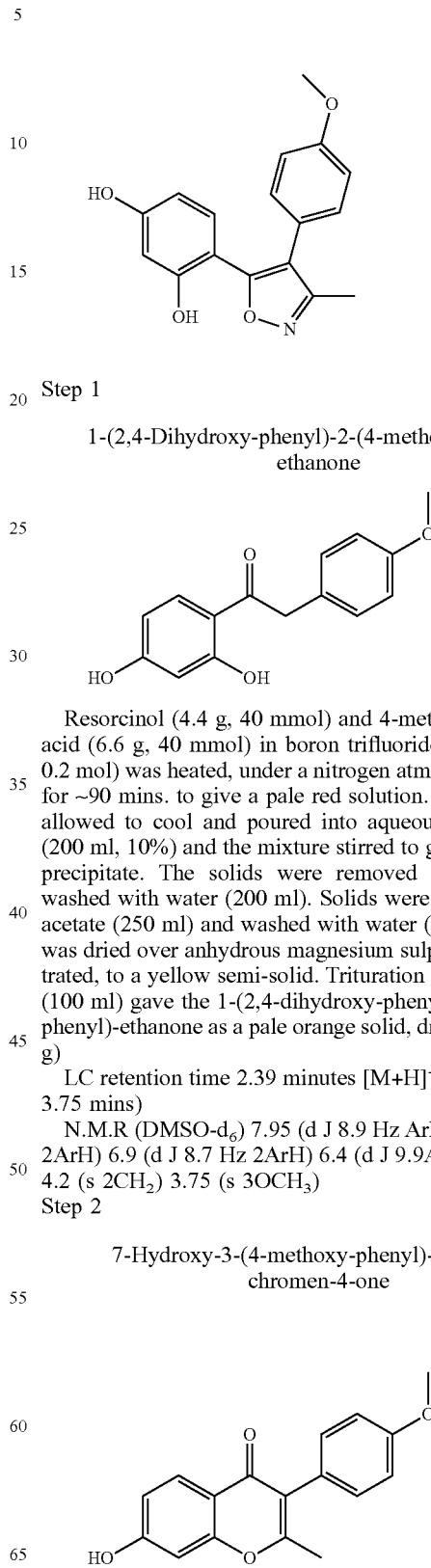

Step 1

1-(2,4-Dihydroxy-phenyl)-2-(4-methoxy-phenyl)-ethanone

Resorcinol (4.4 g, 40 mmol) and 4-methoxyphenylacetic acid (6.6 g, 40 mmol) in boron trifluoride.etherate (25 ml, 0.2 mol) was heated, under a nitrogen atmosphere, at 90° C. for ~90 mins. to give a pale red solution. The solution was allowed to cool and poured into aqueous sodium acetate (200 ml, 10%) and the mixture stirred to give a pale yellow precipitate. The solids were removed by filtration and washed with water (200 ml). Solids were taken up in ethyl acetate (250 ml) and washed with water (200 ml). Solution was dried over anhydrous magnesium sulphate and concentrated, to a yellow semi-solid. Trituration with diethyl ether (100 ml) gave the 1-(2,4-dihydroxy-phenyl)-2-(4-methoxy-phenyl)-ethanone as a pale orange solid, dried in vacuo, (2.2 g)

LC retention time 2.39 minutes [M+H]$^+$ 259.2 (Run time 3.75 mins)

N.M.R (DMSO-d$_6$) 7.95 (d J 8.9 Hz ArH) 7.2 (d J 8.7 Hz 2ArH) 6.9 (d J 8.7 Hz 2ArH) 6.4 (d J 9.9ArH) 6.25 (s ArH) 4.2 (s 2CH$_2$) 3.75 (s 3OCH$_3$)

Step 2

7-Hydroxy-3-(4-methoxy-phenyl)-2-methyl-chromen-4-one

Acetic anhydride (3 ml, 30 mmol) was added to a suspension of potassium carbonate (4.0 g, 29 mmol) and 1-(2,4-dihydroxy-phenyl)-2-(4-methoxy-phenyl)-ethanone (1.95 g, 7.5 mmol) in DMF (10 ml), and the resulting suspension heated at 115° C. for ~90 mins. The mixture was allowed to cool and poured into water (200 ml), to give an off-white precipitate. The solids were removed by filtration and washed with water (100 ml) and diethyl ether (2×40 ml), to give 7-hydroxy-3-(4-methoxy-phenyl)-2-methyl-chromen-4-one as an off-white powder, dried in vacuo, (1.65 g)

LC retention time 2.26 minutes [M+H]$^+$ 283.2 (Run time 3.75 mins)

N.M.R (DMSO-$d_6$) 7.8 (d J 8.7 Hz ArH) 7.2 (d J 8.8 Hz 2ArH) 7.0 (d J 8.8 Hz 2ArH) 6.9 (d J 8.7ArH) 6.8 (s ArH) 3.8 (s 3OCH$_3$) 2.2 (s 3CH$_3$)

Step 3

4-[4-(4-Methoxy-phenyl)-3-methyl-isoxazol-5-yl]-benzene-1,3-diol

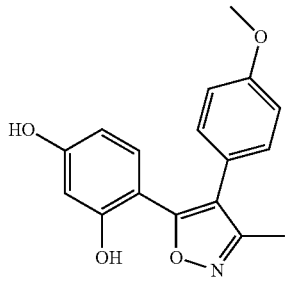 [SMILES: COc1ccc(-c2c(C)noc2-c2ccc(O)cc2O)cc1]

Hydroxylamine hydrochloride (0.35 g, 5 mmol) was added to a suspension of 7-hydroxy-3-(4-methoxy-phenyl)-2-methyl-chromen-4-one (0.14 g, 0.5 mmol) in pyridine (3 ml) and the mixture heated under reflux for ~4 hrs. The solution was allowed to cool and poured into water (50 ml) and extracted with diethyl ether (50 ml). The extracts were washed with water (3×50 ml) and saturated aqueous sodium chloride solution (30 ml). The solution was dried over anhydrous magnesium sulphate and concentrated to give a pale brown gum.

Crude product was purified by column chromatography, on silica, eluting with ethyl acetate/hexane (1:2), to give a colourless gum. Trituration with hexane gave 4-[4-(4-methoxy-phenyl)-3-methyl-isoxazol-5-yl]-benzene-1,3-diol as a white powder, dried in vacuo, (0.087 g)

LC retention time 2.20 minutes [M+H]$^+$ 298.2 (Run time 3.75 mins)

N.M.R (DMSO-$d_6$) 7.1 (d J 8.8 Hz 2ArH) 6.85 (d J 8.6 Hz ArH) 6.8 (d J 8.8 Hz 2ArH) 6.25 (s ArH) 6.15 (d J 8.6 Hz ArH) 3.65 (s 3OCH$_3$) 2.15 (s 3CH$_3$)

Example 2

4-Bromo-6-[4-(4-methoxy-phenyl)-3-methyl-isoxazol-5-yl]-benzene-1,3-diol

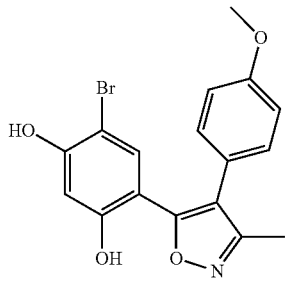 [SMILES: COc1ccc(-c2c(C)noc2-c2cc(Br)c(O)cc2O)cc1]

Benzyltrimethylammonium tribromide (3.95 g, 10 mmol) was added portion-wise to an ice cooled suspension of 4-[4-(4-methoxy-phenyl)-3-methyl-isoxazol-5-yl]-benzene-1,3-diol (Example 1) (2.95 g, 10 mmol) in dichloromethane (50 ml) and the mixture stirred for ~60 mins, at room temperature. Ethyl acetate (300 ml) was added and the mixture washed with water (3×200 ml) and saturated aqueous sodium chloride solution (50 ml). The solution was dried over anhydrous magnesium sulphate and concentrated to give a pale brown solid. Crude product was purified by column chromatography, on silica, eluting with ethyl acetate/hexane (1:2), to give 4-bromo-6-[4-(4-methoxy-phenyl)-3-methyl-isoxazol-5-yl]-benzene-1,3-diol as a white solid, dried in vacuo, (3.42 g)

LC retention time 2.38 minutes [M+H]$^+$ 378.2 (Run time 3.75 mins)

N.M.R (Acetone-$d_6$) 7.35 (s ArH) 7.2 (d J 8.8 Hz 2ArH) 6.9 (d J 8.8 Hz 2ArH) 6.65 (s ArH) 3.8 (s 3OCH$_3$) 2.25 (s 3CH$_3$)

Example 3

5-[4-(4-Methoxy-phenyl)-3-methyl-isoxazol-5-yl]-biphenyl-2,4-diol

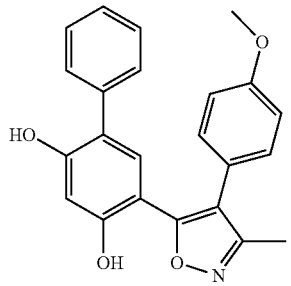 [SMILES: COc1ccc(-c2c(C)noc2-c2cc(-c3ccccc3)c(O)cc2O)cc1]

Step 1

5-(2,4-Bis-benzyloxy-5-bromo-phenyl)-4-(4-methoxy-phenyl)-3-methyl-isoxazole

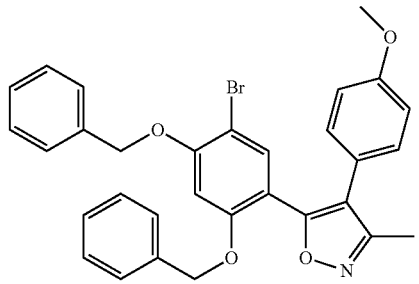 [SMILES: COc1ccc(-c2c(C)noc2-c2cc(Br)c(OCc3ccccc3)cc2OCc2ccccc2)cc1]

Benzyl bromide (0.36 ml, 3 mmol) was added suspension of 4-bromo-6-[4-(4-methoxy-phenyl)-3-methyl-isoxazol-5-yl]-benzene-1,3-diol (Example 2) (0.55 g, 1.5 mmol) and cesium carbonate (0.85 g, 2.6 mmol) in DMF (5 ml) and the mixture stirred for ~18 hrs, at room temperature. Water (100 ml) was added and the mixture extracted with diethyl ether (2×30 ml). The combined extracts were washed with water (4×75 ml) and saturated aqueous sodium chloride solution (50 ml). The solution was dried over anhydrous magnesium sulphate and concentrated to give a pale brown gum. Trituration with hexane gave 5-(2,4-bis-benzyloxy-5-bromo-phenyl)-4-(4-methoxy-phenyl)-3-methyl-isoxazole as an off-white solid, dried in vacuo, (0.5 g).

LC retention time 3.08 minutes [M+H]+ 558.4 (Run time 3.75 mins)

N.M.R (Chloroform-d) 7.55 (s ArH) 7.35-7.25 (m 5ArH) 7.2 (m 3ArH) 6.95 (d J 8.8 Hz 2ArH) 6.85 (m 2ArH) 6.7 (d J 8.8 Hz 2ArH) 6.35 (s ArH) 4.95 (s 2CH$_2$) 4.6 (s 2CH$_2$) 3.75 (s 3OCH$_3$) 2.25 (s 3CH$_3$)

Step 2

5-(4,6-Bis-benzyloxy-biphenyl-3-yl)-4-(4-methoxy-phenyl)-3-methyl-isoxazole

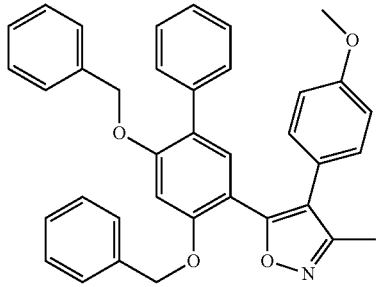 [SMILES: COc1ccc(-c2c(C)noc2-c2cc(-c3ccccc3)c(OCc3ccccc3)cc2OCc2ccccc2)cc1]

Potassium phosphate (0.1 g, 0.5 mmol) was added to a solution of 5-(2,4-bis-benzyloxy-5-bromo-phenyl)-4-(4-methoxy-phenyl)-3-methyl-isoxazole (0.14 g, 0.25 mmol) and phenyl boronic acid (0.095 g, 0.75 mmol) in 1,4 dioxan (4 ml) under a nitrogen atmosphere. Tetrakis(triphenylphosphine)palladium(0) (cat.) was added and the suspension heated, 80° C. for ~18 hrs. The suspension was allowed to cool and ethyl acetate (25 ml) added. The mixture was washed with water (3×25 ml) and saturated aqueous sodium chloride solution (25 ml). The solution was dried over anhydrous magnesium sulphate and concentrated to give a pale brown gum. Trituration with hexane gave 5-(4,6-bis-benzyloxy-biphenyl-3-yl)-4-(4-methoxy-phenyl)-3-methyl-isoxazole as an off-white solid, dried in vacuo.

LC retention time 3.08 minutes [M+H]+ 554.4 (Run time 3.75 mins)

N.M.R (Chloroform-d) 7.4 (m 2ArH) 7.35 (s ArH) 7.3-7.1 (m 11ArH) 6.95 (d J 8.8 Hz 2ArH) 6.9 (m 2ArH) 6.7 (d J 8.8 Hz 2ArH) 6.45 (s ArH) 4.9 (s 2CH$_2$) 4.7 (s 2CH$_2$) 3.75 (s 3OCH$_3$) 2.25 (s 3CH$_3$)

Step 3

7-Hydroxy-3-(4-methoxy-phenyl)-2-methyl-6-phenyl-chromen-4-one

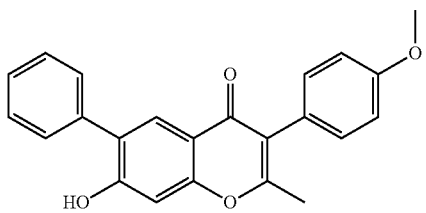 [SMILES: COc1ccc(-c2c(C)oc3cc(O)c(-c4ccccc4)cc3c2=O)cc1]

Ammonium formate (3.2 g, 50 mmol) was added to a solution of 5-(4,6-bis-benzyloxy-biphenyl-3-yl)-4-(4-methoxy-phenyl)-3-methyl-isoxazole (1.4 g, 2.5 mmol) in methanol (20 ml)/ethyl acetate (10 ml) under a nitrogen atmosphere. Palladium on carbon (10%) (cat.) was added and the suspension heated, at 60° C. for ~18 hrs. The suspension was allowed to cool and ethyl acetate (150 ml) added, and the suspension filtered. The filtrate was washed with water (3×100 ml) and saturated aqueous sodium chloride solution (50 ml). The solution was dried over anhydrous magnesium sulphate and concentrated to give a pale brown gum. Trituration with methanol gave 7-hydroxy-3-(4-methoxy-phenyl)-2-methyl-6-phenyl-chromen-4-one as an off-white solid, dried in vacuo.

LC retention time 2.58 minutes [M+H]+ 359.2 (Run time 3.75 mins)

N.M.R (DMSO-d$_6$) 7.9 (s ArH) 7.5-7.3 (m 5ArH) 7.25 (d J 8.8 Hz 2ArH) 7.1 (s ArH) 7.05 (d J 8.8 Hz 2ArH) 3.85 (s 3OCH$_3$) 2.2 (s 3CH$_3$)

Step 4

5-[4-(4-Methoxy-phenyl)-3-methyl-isoxazol-5-yl]-biphenyl-2,4-diol

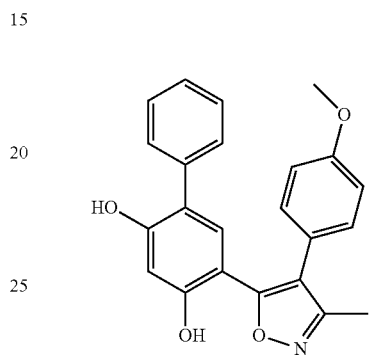

Hydroxylamine hydrochloride (75 mg, 1.08 mmol) was added to a suspension of 7-hydroxy-3-(4-methoxy-phenyl)-2-methyl-6-phenyl-chromen-4-one (105 mg, 0.29 mmol) in pyridine (2 ml) and the mixture heated under reflux for ~6 hrs., to give a pale yellow solution. The solution was allowed to cool and water (20 ml) added. The mixture was extracted with diethyl ether (2×10 ml). The combined extracts were washed with water (2×20 ml) and saturated aqueous sodium chloride solution (10 ml). The solution was dried over anhydrous magnesium sulphate and concentrated. The crude products were purified by column chromatography, silica, eluting with ethyl acetate/hexane (1:1), to give the title compound as an off-white powder (80 mg)

LC retention time 2.56 minutes [M+H]+ 374.3 (Run time 3.75 mins)

N.M.R (Acetone-d$_6$) 7.5-7.3 (m 5ArH) 7.2 (d J 8.8 Hz 2ArH) 7.0 (d J 8.8 Hz 2ArH) 6.9 (d J 8.6 Hz ArH) 6.35 (s ArH) 6.1 (d J 8.7 Hz ArH) 3.85 (s 3OCH$_3$) 2.25 (s 3CH$_3$)

Example 4

4-Chloro-6-[4-(4-methoxy-phenyl)-3-methyl-isoxazol-5-yl]-benzene-1,3-diol

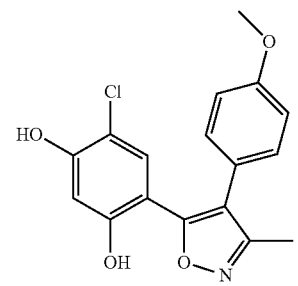 [SMILES: COc1ccc(-c2c(C)noc2-c2cc(Cl)c(O)cc2O)cc1]

Hydroxylamine hydrochloride (0.7 g, 10 mmol) was added to a suspension of 6-chloro-7-hydroxy-3-(4-methoxyphenyl)-2-methyl-chromen-4-one [prepared analogously to Example 1, Step 2] (0.32 g, 1.0 mmol) in pyridine (4 ml) and the mixture heated under reflux for ~6 hrs., to give a pale yellow solution. The solution was allowed to cool and water (20 ml) added. The mixture was extracted with diethyl ether (2×10 ml). The combined extracts were washed with water (2×20 ml) and saturated aqueous sodium chloride solution (10 ml). The solution was dried over anhydrous magnesium sulphate and concentrated. The crude products were purified by column chromatography, silica, eluting with ethyl acetate/hexane (1:1), to give 4-chloro-6-[4-(4-methoxy-phenyl)-3-methyl-isoxazol-5-yl]-benzene-1,3-diol as an off-white powder (0.103 g)

LC retention time 2.37 minutes [M+H]$^+$ 332.2 (Run time 3.75 mins)

N.M.R (Acetone-$d_6$) 7.2 (d J 8.8 Hz 2ArH) 7.15 (s ArH) 6.9 (d J 8.8 Hz 2ArH) 6.6 (s ArH) 3.85 (s 3OCH$_3$) 2.25 (s 3CH$_3$)

The compounds of Examples 1-4 had an HSP90 IC50 in the range A when tested in the Malachite Green ATPase assay described below. In the following tables, the final column gives the result on the same basis for the compound in question, except in the case of Example 12b, where the activity quoted is as measured in the fluorescence polarisation assay described below.

Examples 5-16 were prepared using the reaction described for Examples 1-4. Other details of the preparation Examples 6 and 7 are analagous to those of Examples 86 and 87.

| Example | Structure | MH+ | Hsp90 IC50 |
|---|---|---|---|
| 5* | | 326 | B |
| 6 | | 330 | B |
| 7 | | 296 | B |
| 8 | 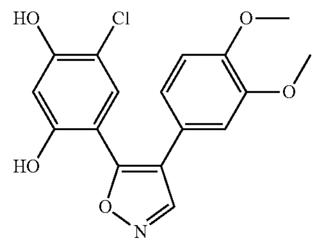 [SMILES: COc1ccc(-c2cnoc2-c2cc(Cl)c(O)cc2O)cc1OC] | 349 | B |
| 9 | 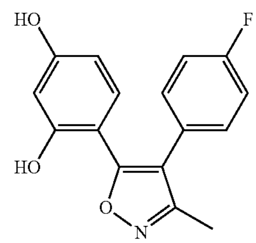 [SMILES: Cc1noc(-c2ccc(O)cc2O)c1-c1ccc(F)cc1] | 286 | A |
| 10 | 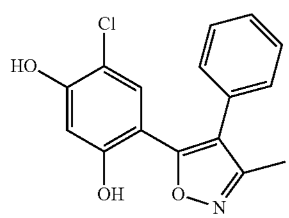 [SMILES: Cc1noc(-c2cc(Cl)c(O)cc2O)c1-c1ccccc1] | 303 | A |
| 11 | 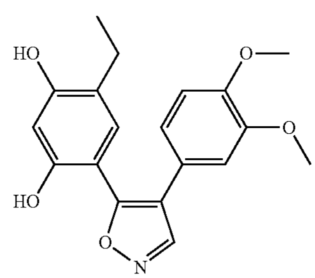 [SMILES: CCc1cc(-c2oncc2-c2ccc(OC)c(OC)c2)c(O)cc1O] | 342 | A |
| 12 | 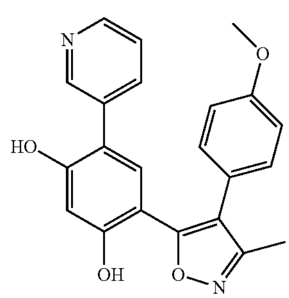 [SMILES: COc1ccc(-c2c(C)noc2-c2cc(-c3cccnc3)c(O)cc2O)cc1] | 375 | B |

-continued

| Example | Structure | MH+ | Hsp90 IC50 |
|---|---|---|---|
| 12a | 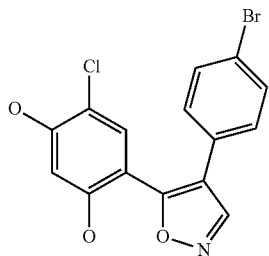 [SMILES: Oc1cc(O)c(-c2oncc2-c2ccc(Br)cc2)cc1Cl] | 367 | A |
| 12b | 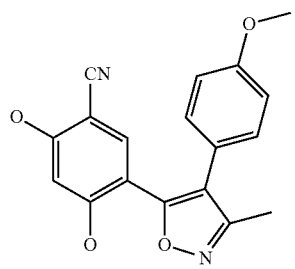 [SMILES: COc1ccc(-c2c(C)noc2-c2cc(C#N)c(O)cc2O)cc1] | 323 | A* |
| 12c§ | 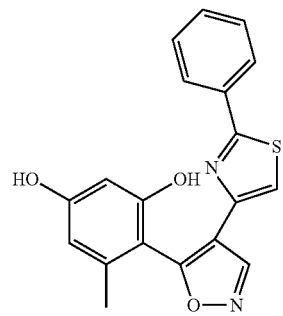 [SMILES: Cc1cc(O)cc(O)c1-c1oncc1-c1csc(-c2ccccc2)n1] | 351 | A |
| 12d§ | 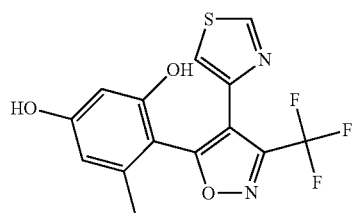 [SMILES: Cc1cc(O)cc(O)c1-c1onc(C(F)(F)F)c1-c1cscn1] | 343 | A |

*Also available commercially from Interbioscreen
§available commercially from Enamine
**prepared from protected bromo resorcinol intermediate with copper (I) cyanide in dimethylformamide at 150° C.
***Fluorescence Polarisation Assay: 'A' = <10 uM; 'B' = >10 uM

Example 14

4-[4-(4-Methoxy-phenyl)-3-methyl-isoxazol-5-yl]-6-phenethyl-benzene-1,3-diol was prepared from styryl boronic acid coupling of the bromo isoxazole compound of Example 2 Step 1, as described above, followed by reduction and treatment with hydroxylamine, analogously to Example 3.

LC retention time 2.56 minutes [M+H]+ 402 (Run time 3.75 mins)

Example 15

4-[4-(4-Methoxy-phenyl)-3-methyl-isoxazol-5-yl]-2,6-bis-(4-methyl-piperazin-1-ylmethyl)-benzene-1,3-diol Scheme 2: Mannich reaction

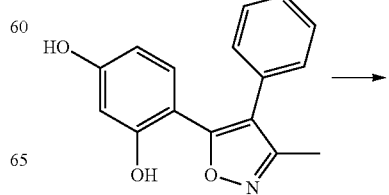

-continued

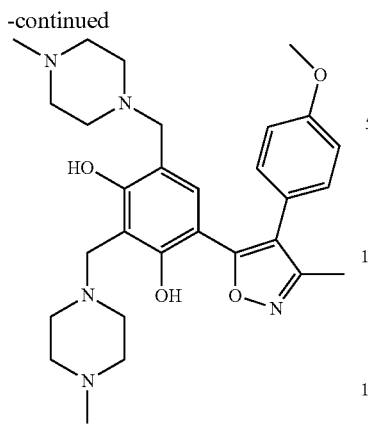

Scheme 3: formation of ester

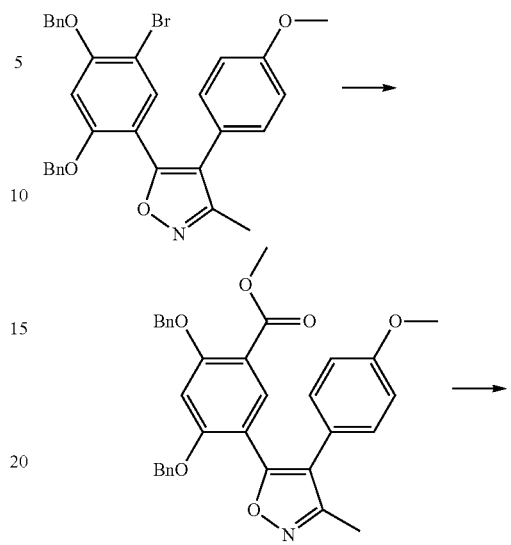

N-methylpiperazine (0.125 ml, 1.1 mmol) was added to a suspension of 4-[4-(4-methoxy-phenyl)-3-methyl-isoxazol-5-yl]-benzene-1,3-diol (0.15 g, 0.5 mmol) and paraformaldehyde (0.040 g) in 1,4-dioxan (4 ml) and the mixture heated under reflux for ~18 hrs., to give a brown yellow solution. The solution was allowed to cool and ethyl acetate (25 ml) added. The mixture was washed with water (3×25 ml) and saturated aqueous sodium chloride solution (25 ml). The solution was dried over anhydrous magnesium sulphate and concentrated to a pale brown gum. Trituration with hexane, gave 4-[4-(4-methoxy-phenyl)-3-methyl-isoxazol-5-yl]-2,6-bis-(4-methyl-piperazin-1-ylmethyl)-benzene-1,3-diol (0.121 g) as a pale brown powder.

LC retention time 1.61 minutes [M+H]$^+$ 522.6 (Run time 3.75 mins)

N.M.R (Acetone-d$_6$) 7.2 (d J 8.8 Hz 2ArH) 6.95 (s ArH) 6.8 (d J 8.8 Hz 2ArH) 3.85 (s 3OCH$_3$) 3.75 (s 2CH$_2$) 3.65 (s 2CH$_2$) 2.9-2.0 (br s 16CH$_2$) 2.3 (s 3CH$_3$) 2.25 (s 3CH$_3$) 2.2 (s 3CH$_3$)

Example 16

2,4-Dihydroxy-5-[4-(4-methoxy-phenyl)-3-methyl-isoxazol-5-yl]benzoic acid methyl ester

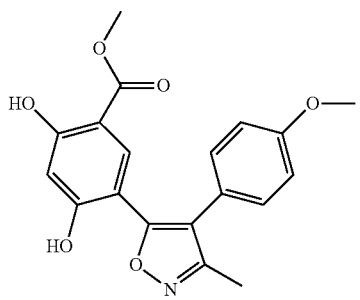 [SMILES: COC(=O)c1cc(-c2onc(C)c2-c2ccc(OC)cc2)c(O)cc1O]

Step 1 n-Butyl lithium (100 µl) was added to a solution of 5-(2,4-bis-benzyloxy-5-bromo-phenyl)-4-(4-methoxy-phenyl)-3-methyl-isoxazole (154 mg, 0.28 mmol) in tetrahydrofuran (2.5 ml) under a nitrogen atmosphere at −78° C. Solution stirred at −70° C. for 30 minutes to give an orange solution. The ion was quenched with methyl chloroformate (100 µl, 3 eq) and allowed to warm to room temperature for 30 minutes. The solution was quenched with saturated aqueous ammonium chloride (5 ml). The mixture was extracted with ethyl acetate (3×5 ml). The combined extracts were washed with water (2×5 ml) and saturated aqueous sodium chloride solution (5 ml). The solution was dried over anhydrous magnesium sulphate and concentrated. The crude products were purified by column chromatography, silica, eluting with ethyl acetate in hexane (gradient 20% to 60% ethyl acetate) to give 2,4-Bis-benzyloxy-5-[4-(4-methoxy-phenyl)-3-methyl-isoxazol-5-yl]-benzoic acid methyl ester (72 mg).

LC retention time 4.95 minutes [M+H]$^+$ 536.4 (Run time 7.5 mins)

N.M.R (DMSO-d$_6$) 7.8 (s ArH) 7.55 (d J 7.1 Hz 2ArH) 7.4 (t J 6.2 Hz 2ArH) 7.35 (d J 6.1 Hz ArH) 7.3 (m 3ArH) 7.1 (m 4ArH) 7.0 (s ArH) 6.9 (d 8.8 Hz 2ArH) 5.3 (s 2CH$_2$) 5.1 (s 2CH$_2$) 3.78 (s OCH$_3$) 3.76 (s OCH$_3$) 2.28 (s CH$_3$)

Step 2

Ammonium formate (172 mg, 20 eq) was added to a solution of 2,4-Bis-benzyloxy-5-[4-(4-methoxy-phenyl)-3-methyl-isoxazol-5-yl]-benzoic acid methyl ester (72 mg, 0.13 mmol) in methanol (2 ml)/ethyl acetate (1 ml) under a nitrogen atmosphere. 10% Palladium on carbon (cat.) was added and the suspension heated at 60° C. overnight. The solution was allowed to cool. Ethyl acetate (5 ml) added, solution washed with water (2×5 ml) and saturated aqueous sodium chloride solution (5 ml). The solution was dried over anhydrous magnesium sulphate and concentrated. The crude products were purified by column chromatography, silica, eluting with ethyl acetate in hexane (gradient 25% to 45% ethyl acetate) to give 2,4-dihydroxy-5-[4-(4-methoxy-phenyl)-3-methyl-isoxazol-5-yl]-benzoic acid methyl ester (7.0 mg).

LC retention time 2.49 minutes [M+H]$^+$ 356.3 (Run time 3.75 mins)

N.M.R(CDCl$_3$) δ=10.85 (s ArOH) 7.52 (s ArOH) 7.12 (d J8 Hz 2ArH) 6.98 (s ArH) 6.91 (d J8 Hz 2ArH) 6.45 (s ArH) 3.78 (s 3 OCH$_3$) 3.71 (s 3 OCH$_3$) 2.21 (s 3 CH$_3$).

The compounds of Examples 14-16 had an HSP90 IC50 in the ranges 'A', 'B' and 'B', respectively when tested in the Malachite Green ATPase assay described below.

Similarly, Examples 17-20 were prepared quenching with N-formyl piperidine, phenyl thioisocyanate, 2-methoxy phenyl isocyanate and benzaldehyde, respectively. The final deprotection reaction was carried out with boron trichloride as described for example 23 (last reaction on Scheme 5). Example 21 was a by-product from Step 1, Example 16. Quoted activities are those obtained in the Malachite Green Assay described below.

| Example | Structure | MH+ | Hsp90 IC50 |
|---|---|---|---|
| 17 | | 326 | B |
| 18 | | 433 | B |
| 19 | 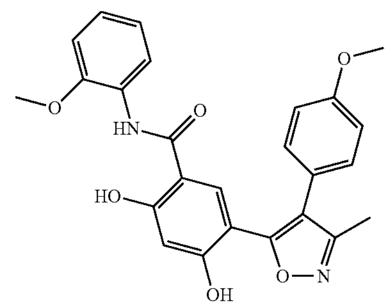 | 447 | A |
| 20 | 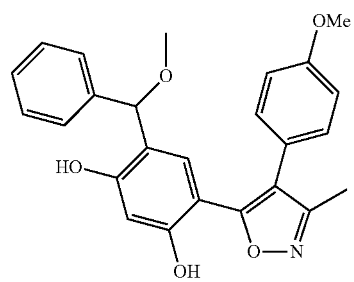 [SMILES: COc1ccc(-c2c(C)noc2-c2cc(C(OC)c3ccccc3)c(O)cc2O)cc1] | 418 | A |
| 21 | 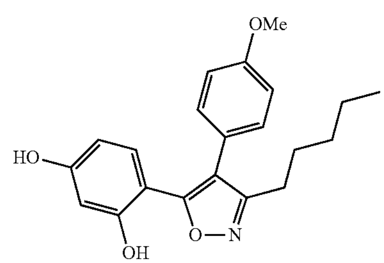 [SMILES: CCCCCc1noc(-c2ccc(O)cc2O)c1-c1ccc(OC)cc1] | 354 | A |

Example 22

4-Benzyl-6-[4-(4-methoxy-phenyl)-3-methyl-isoxazol-5-yl]-benzene-1,3-diol

Scheme 4: Synthesis of benzyl resorcinol

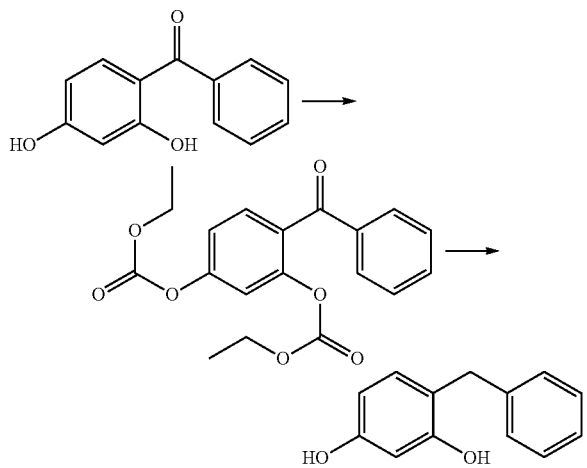

Carbonic acid 2-benzoyl-5-ethoxycarbonyloxy-phenyl ester ethyl ester

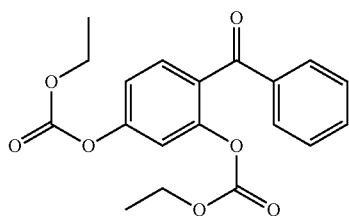 [SMILES: CCOC(=O)Oc1ccc(C(=O)c2ccccc2)c(OC(=O)OCC)c1]

Triethyl amine (10 ml, 72.2 mmol) was added to a solution of 2,4-dihydroxybenzophenone (1) (5.4 g, 23.3 mmol) in THF (50 ml) and the solution cooled to 0° C. Ethyl chloroformate (6.9 ml, 72.2 mmol) was added slowly and the suspension stirred for ~30 mins at 0° C., and for ~3 hrs at room temperature. Water (150 ml) was added and the mixture extracted with diethyl ether (150 ml). The extracts were washed with water (2×150 ml) and saturated aqueous sodium chloride solution (100 ml). The solution was dried over anhydrous magnesium sulphate and concentrated to give 4-benzyl-benzene-1,3-diol as a pale green gum, solidified on standing, (8.2 g).

LC retention time 2.73 minutes [M+H]+ 359.2 (Run time 3.75 mins) 6 (Chloroform-d) 7.7 (m 2ArH) 7.5 (m 2ArH) 7.35 (m 2ArH) 7.15 (m 2ArH) 4.25 (q J 7.1 Hz 2CH$_2$) 4.05 (q J 7.1 Hz 2CH$_2$) 1.35 (t J 7.1 Hz 3CH$_3$) 1.15 (t J 7.1 Hz 3 CH$_3$)

4-benzyl-benzene-1,3-diol

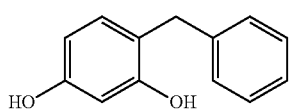

A solution of sodium borohydride (1.85 g, 49 mmol) in water (30 ml) was added to an ice cooled solution of carbonic acid 2-benzoyl-5-ethoxycarbonyloxy-phenyl ester ethyl ester (3.6 g, 10 mmol) in THF (30 ml). The mixture was stirred for ~60 mins. at 0° C., and for ~60 hrs. at room temperature, to give a pale red suspension. Water (150 ml) was added and the mixture extracted with diethyl ether (150 ml). The extracts were washed with water (2×100 ml) and saturated aqueous sodium chloride solution (50 ml). The solution was dried over anhydrous magnesium sulphate and concentrated to give a pale yellow gum. The gum was taken up in aqueous sodium hydroxide (20 ml, 10%), and the solution heated under reflux for ~60 mins. The solution was allowed to cool and acidified with hydrochloric acid (5 ml, 37%). The mixture was extracted with diethyl ether (50 ml). The extracts were washed with water (3×40 ml) and saturated aqueous sodium chloride solution (30 ml). The solution was dried over anhydrous magnesium sulphate and concentrated to give 4-benzyl-benzene-1,3-diol as a dark red gum, (2.1 g).

LC retention time 2.28 minutes [M+H]+ no ion (Run time 3.75 mins)

δ (Chloroform-d) 7.2 (m 3ArH) 7.1 (m 2ArH) 6.85 (d J 8.1 Hz ArH) 6.3 (d J 8.1 Hz ArH) 6.2 (s ArH) 3.85 (s 2CH$_2$)

The 4-benzyl-benzene-1,3-diol was used as the starting material in a Scheme 1 synthesis to provide Example 23.

Example 23

3-{2,4-Dihydroxy-5-[4-(4-methoxy-phenyl)-3-methyl-isoxazol-5-yl]-phenyl}-acrylic acid

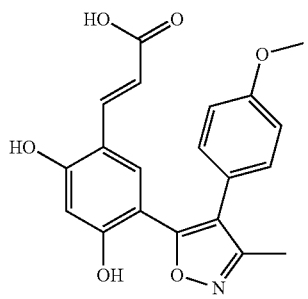 [SMILES: COc1ccc(-c2c(C)noc2-c2cc(/C=C/C(=O)O)c(O)cc2O)cc1]

Scheme 5: Heck reaction and boron trichloride deprotection

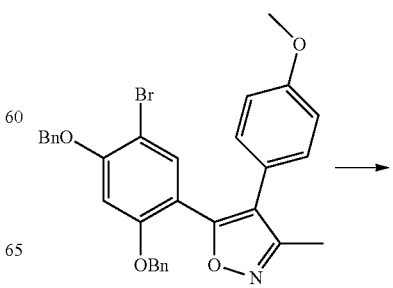

-continued

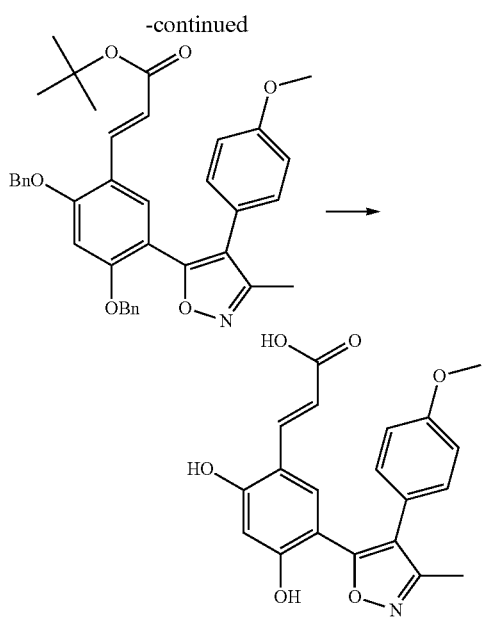

Step 1

3-{2,4-Bis-benzyloxy-5-[4-(4-methoxy-phenyl)-3-methyl-isoxazol-5-yl]-phenyl}-acrylic acid tert-butyl ester

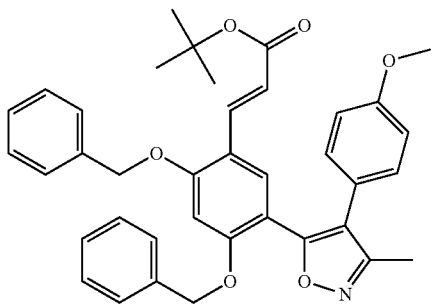 [SMILES: COc1ccc(-c2c(C)noc2-c2cc(/C=C/C(=O)OC(C)(C)C)c(OCc3ccccc3)cc2OCc2ccccc2)cc1]

Diisopropylethyl amine (1 ml, 5.7 mmol) was added to a suspension of 5-(2,4-Bis-benzyloxy-5-bromo-phenyl)-4-(4-methoxy-phenyl)-3-methyl-isoxazole (0.56 g, 1.0 mmol) in tert-butyl acrylate (1 ml, 6.8 mmol) and 1-butanol (8 ml) under a nitrogen atmosphere. Dichlorobis(tri-o-tolylphosphine)palladium (II) (cat.) was added and the suspension heated, 140° C. for ~18 hrs., to give a yellow/green solution. The solution was allowed to cool and concentrated to a yellow/green gum. The crude product was purified by column chromatography, silica, eluting with ethyl acetate/hexane (1:9), to give 3-{2,4-Bis-benzyloxy-5-[4-(4-methoxy-phenyl)-3-methyl-isoxazol-5-yl]-phenyl}-acrylic acid tert-butyl ester as a yellow/green gum (315 mg). Starting material (170 mg) was recovered.

LC retention time 3.23 minutes [M+H]$^+$ 604.6 (Run time 3.75 mins)

N.M.R (Chloroform-d) 7.85 (d J 16.1 Hz CH) 7.6 (s ArH) 7.4-7.25 (m 8ArH) 7.05 (d J 8.8 Hz 2ArH) 6.9 (m 2ArH) 6.8 (d J 8.8 Hz 2ArH) 6.5 (s ArH) 6.35 (d J 16.1 Hz CH) 5.05 (s 2CH$_2$) 4.75 (s 2CH$_2$) 3.75 (s 3OCH$_3$) 2.25 (s 3CH$_3$) 1.5 (s 9CCH$_3$)

Step 2

3-{2,4-Dihydroxy-5-[4-(4-methoxy-phenyl)-3-methyl-isoxazol-5-yl]-phenyl}-acrylic acid

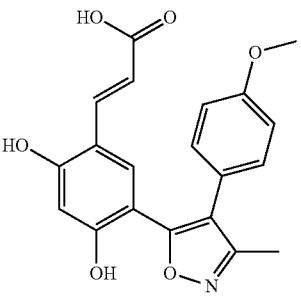 [SMILES: COc1ccc(-c2c(C)noc2-c2cc(/C=C/C(=O)O)c(O)cc2O)cc1]

Boron trichloride solution (2 ml, 1.0M in dichloromethane) was added slowly to a solution of 3-{2,4-Bis-benzyloxy-5-[4-(4-methoxy-phenyl)-3-methyl-isoxazol-5-yl]-phenyl}-acrylic acid tert-butyl ester (50 mg, 0.09 mmol) in dichloromethane (1 ml), at −78° C. (dry ice/acetone) under a nitrogen atmosphere. The resulting solution was stirred for ~1 hr at −78° C., and for ~90 mins. at room temperature. The solution was cooled to −78° C. and water (2 ml) added and the mixture was stirred for ~30 mins at room temperature. Ethyl acetate (30 ml) was added and the solution washed with water (2×5 ml) and saturated aqueous sodium chloride solution (10 ml). The solution was dried over anhydrous magnesium sulphate and concentrated to a pale yellow gum. Trituration with hexane gave a yellow solid, solids were removed by filtration and washed with hexane, dried in vacuo, to give 3-{2,4-dihydroxy-5-[4-(4-methoxy-phenyl)-3-methyl-isoxazol-5-yl]-phenyl}-acrylic acid (10 mg) as yellow powder.

LC retention time 2.08 minutes [M+H]$^+$ 368.3 (Run time 3.75 mins)

N.M.R (Acetone-d$_6$) 7.85 (d J 16.1 Hz CH) 7.5 (s ArH) 7.25 (d J 8.8 Hz 2ArH) 6.95 (d J 8.8 Hz 2ArH) 6.6 (s ArH) 6.35 (d J 16.1 Hz CH) 3.8 (s 3OCH$_3$) 2.25 (s 3CH$_3$)

Similarly, 4-[4-(4-methoxy-phenyl)-3-methyl-isoxazol-5-yl]-6-styryl-benzene-1,3-diol (Example 24) was prepared by boron trichloride deprotection of 5-(2,4-Bis-benzyloxy-5-styryl-phenyl)-4-(4-methoxy-phenyl)-3-methyl-isoxazole (prepared from styryl boronic acid coupling of bromo isoxazole intermediate, Example 3))

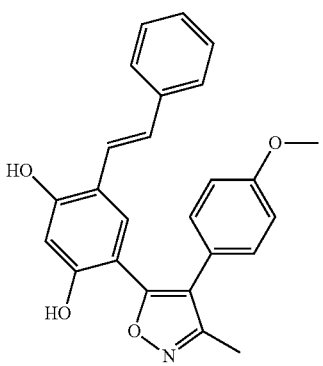 [SMILES: COc1ccc(-c2c(C)noc2-c2cc(/C=C/c3ccccc3)c(O)cc2O)cc1]

LC retention time 2.08 minutes [M+H]$^+$ 368.3 (Run time 3.75 mins)

The compounds of Examples 22-24 had an HSP90 IC50 in the ranges 'A', 'B' and 'C' respectively when tested in the Malachite Green ATPase assay described below.

Scheme 6:
Synthesis of 5-carboxamido isoxazoles

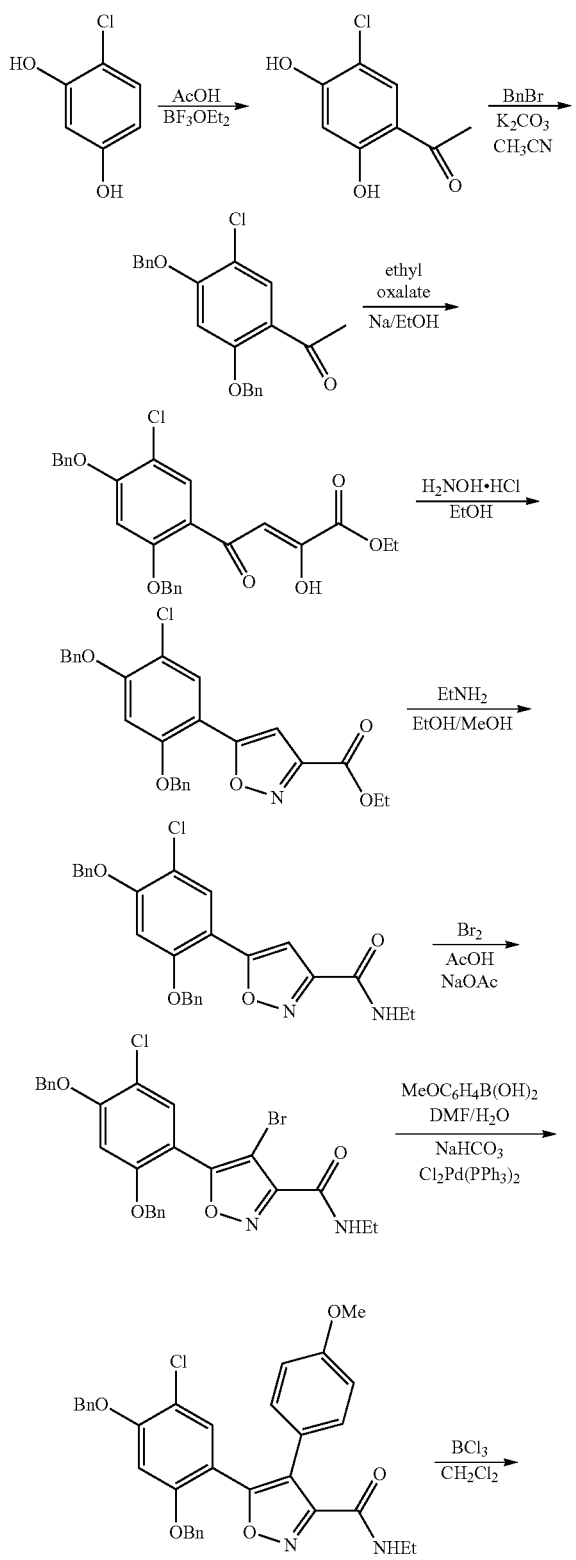

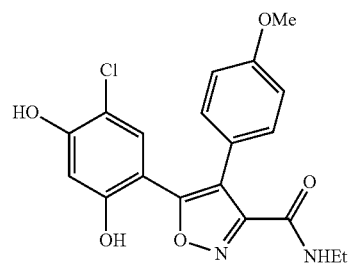

Example 25

5-(5-chloro-2,4-dihydroxyphenyl)-4-(4-methoxyphenyl)-isoxazole-3-carboxylic acid ethylamide

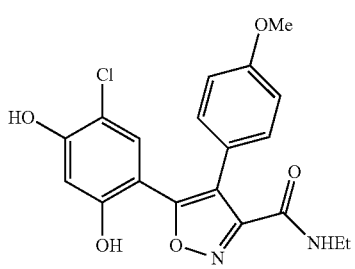

Step 1

1-(5-Chloro-2,4-dihydroxy-phenyl)-ethanone

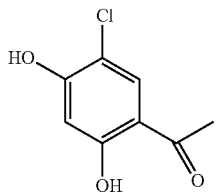

Acetic acid (17.5 mL) was added dropwise to a suspension of 4-chlororesorcinol (42.5 g, 0.293 mmol) in boron trifluoride etherate (200 mL) under a nitrogen atmosphere. The reaction mixture was heated at 90° C. for 3.5 hours and then allowed to cool to room temperature. A solid had formed after around 1 hour of cooling. The mixture was poured into 700 mL of a 10% w/v aqueous sodium acetate solution. This mixture was stirred vigorously for 2.5 hours. A light brown solid had formed which was filtered, washed with water and air-dried overnight to afford 1-(5-chloro-2, 4-dihydroxy-phenyl)-ethanone (31.6 g, 58%). LCMS: [M−H]+ 185.

Step 2

1-(2,4-Bis-benzyloxy-5-chloro-phenyl)-ethanone

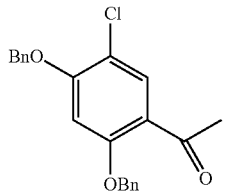

Benzyl bromide (30 mL) was added to a mixture of 1-(5-chloro-2,4-dihydroxy-phenyl)-ethanone (20 g, 0.107 moles) and potassium carbonate (37 g, 2.5 equiv) in acetonitrile (350 mL). The mixture was heated at reflux for 6 hours then allowed to cool and stirred overnight. The mixture was filtered and the solids were washed with dichloromethane (3×100 mL). The combined organic extracts were evaporated in vacuo to leave a pale yellow solid which was triturated with a mixture of hexane (350 mL)/ethyl acetate (15 mL) and filtered to give an off-white solid, 1-(2,4-bis-benzyloxy-5-chloro-phenyl)-ethanone (35.4 g, 90%). 1H NMR (400 MHz) consistent with structure.

Step 3

4-(2,4-bis-benzyloxy-5-chlorophenyl)-2-hydroxy-4-oxo-but-2-enoic acid ethyl ester

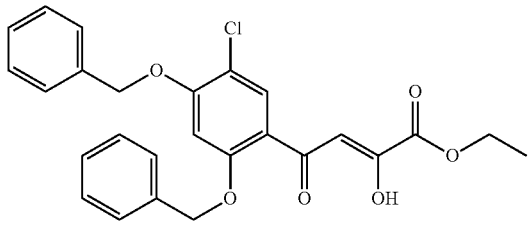 [SMILES: CCOC(=O)/C(O)=C/C(=O)c1cc(Cl)c(OCc2ccccc2)cc1OCc1ccccc1]

Sodium metal (1.35 g, 0.058 mol) was added in small pieces over a period of 20 minutes to stirred anhydrous ethanol under a nitrogen atmosphere. The reaction mixture was then stirred for a further 10 minutes until all the sodium had reacted to give a homogeneous solution. 1-(2,4-bis-benzyloxy-5-chloro-phenyl)-ethanone (10.0 g, 0.027 mol) was added in portions over 2-3 minutes and the resulting suspension was stirred for 5 minutes prior to addition of diethyl oxalate (6 ml, 0.043 mol) which afforded a thicker, yellow precipitate. The reaction mixture was heated to reflux (giving homogeneous brown solution) for 4 hours, then allowed to cool to room temperature and acetic acid (6 ml) was added. The resulting which solid forms was triturated, filtered, washed with ethanol and dried to give a yellow solid (12.0 g, 95%). $^1$H NMR (400 MHz, CDCl$_3$) δ 1.2 (t, 3H), 4.19 (q, 2H), 5.05 (s, 2H), 5.10 (s, 2H), 6.50 (s, 1H), 7.22-7.41 (m, 10H), 7.97 (s, 1H).

Step 4

5-(2,4-Bis-benzyloxy-5-chlorophenyl)-isoxazole-3-carboxylic acid ethyl ester

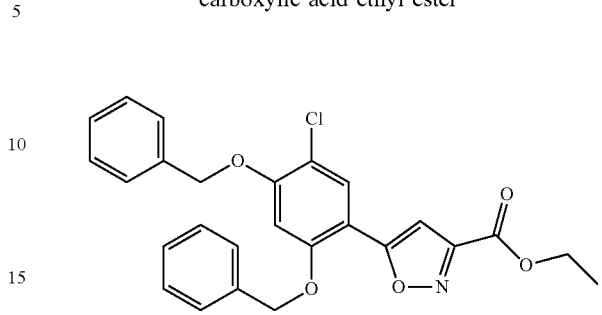

Hydroxylamine hydrochloride (0.89 g; 12.8 mmol) was added to a suspension of 4-(2,4-bis-benzyloxy-5-chlorophenyl)-2-hydroxy-4-oxo-but-2-enoic acid ethyl ester (5.00 g; 10.7 mmol) in absolute ethanol (100 ml). The reaction mixture was heated at reflux for four hours then allowed to cool to ambient temperature (during this time the mixture remains heterogeneous but becomes lighter yellow in colour). The mixture was filtered and the filtered solid was washed with water (2×20 ml), ethanol (2×20 ml) and dried in vacuo at 45° C. This affords 5-(2,4-bis-benzyloxy-5-chlorophenyl)-isoxazole-3-carboxylic acid ethyl ester as a fluffy yellow solid, 4.49 g (91%) LCMS: [M+H]$^+$ 466, 464 ($^{37}$Cl; $^{35}$Cl).). $^1$H NMR (400 MHz, CDCl$_3$) δ 1.42 (t, 3H), 4.42 (q, 2H), 5.13 (s, 2H), 5.14 (s, 2H), 6.62 (s, 1H), 7.01 (s, 1H), 7.35-7.43 (m, 10H), 8.00 (s, 1H).

Step 5

5-(2,4-Bis-benzyloxy-5-chlorophenyl)-isoxazole-3-carboxylic acid ethylamide

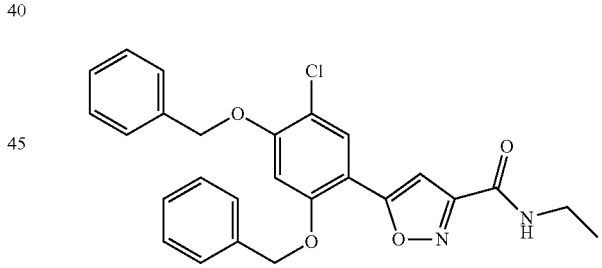

A solution of ethylamine in methanol solution (2.0M; 40 mL; 80 mmol) was added to a stirred suspension of 5-(2,4-bis-benzyloxy-5-chlorophenyl)-isoxazole-3-carboxylic acid ethyl ester (4.40 g; 9.51 mmol) in absolute ethanol (50 ml). The reaction mixture was heated to 80° C. (oil-bath temperature) for five hours. The reaction mixture was allowed to cool to ambient temperature and left to stand overnight. A colourless solid product formed and the reaction mixture was further cooled in an ice-water bath, filtered and washed with cold ethanol (2×20 ml). The colourless product was dried in vacuo to afford 5-(2,4-bis-benzyloxy-5-chlorophenyl)-isoxazole-3-carboxylic acid ethylamide 3.42 g (78%) LCMS: [M+H]$^+$ 465, 463 ($^{37}$Cl; $^{35}$Cl). $^1$H NMR (400 MHz, CDCl$_3$) δ 1.25 (t, 3H), 3.48 (m, 2H), 5.10 (s, 2H), 5.2 (s, 2H), 6.59 (s, 1H), 6.83 (brt, 1H), 7.08 (s, 1H), 7.30-7.41 (m, 10H), 7.97 (s, 1H).

Step 6

5-(2,4-Bis-benzyloxy-5-chlorophenyl)-4-bromo-isoxazole-3-carboxylic acid ethylamide

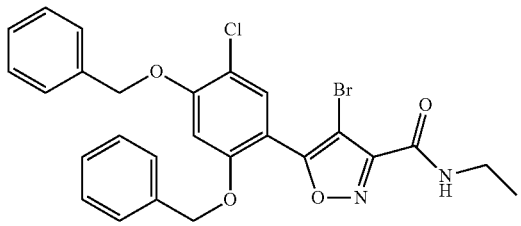 [SMILES: CCNC(=O)c1noc(-c2cc(Cl)c(OCc3ccccc3)cc2OCc2ccccc2)c1Br]

A solution of bromine in acetic acid (0.6M; 7.2 mL; 4.32 mmol) was added to a stirred suspension of 5-(2,4-Bis-benzyloxy-5-chlorophenyl)-4-bromo-isoxazole-3-carboxylic acid ethylamide (2.00 g; 4.32 mmol) and sodium acetate (0.708 g, 8.64 mmol) in acetic acid (30 ml) at ambient temperature. The mixture was heated to 80° C. and becomes homogeneous within 5-10 minutes, to afford a dark red solution. After heating for 2.5 hours the solution was yellow in colour. TLC analysis showed starting material and product present. A further 2.0 ml (1.2 mmol) of the bromine in acetic acid solution was added over the next two hours. The reaction mixture was allowed to cool to ambient temperature and acetic acid was removed in vacuo to afford a solid residue, which was partitioned between ether (200 ml) and water (200 ml). The phases were separated and the organic phase was washed with water (3×100 ml), saturated aqueous sodium bicarbonate solution (2×100 ml) and saturated sodium chloride solution (1×200 ml). The organic phase was dried over sodium sulphate, filtered and the filtrate solvents were removed in vacuo to afford a yellow oil which was purified by flash chromatography on silica gel, eluting with 1-20% ethyl acetate in hexane. This affords product as colourless solid, 1.2 g (52%) LCMS: [M+H]$^+$ 543, 541 ($^{81}$Br; $^{79}$Br). $^1$H NMR (400 MHz, CDCl$_3$) δ 1.26 (t, 1H), 3.50 (m, 2H), 5.01 (s, 2H), 5.12 (s, 2H), 6.62 (s, 1H), 6.74 (br t, 1H), 2.28-7.41 (m, 10H), 7.53 (s, 1H).

Step 7

5-(2,4-Bis-benzyloxy-5-chlorophenyl)-4-(4-methoxy-phenyl)-isoxazole-3-carboxylic acid ethylamide

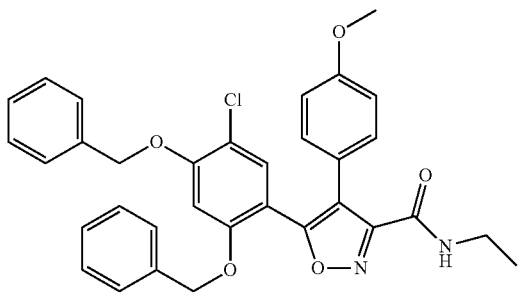 [SMILES: CCNC(=O)c1noc(-c2cc(Cl)c(OCc3ccccc3)cc2OCc2ccccc2)c1-c1ccc(OC)cc1]

To a mixture of 4-methoxyphenylboronic acid (0.178 g, 1.17 mmol) and 5-(2,4-Bis-benzyloxy-5-chlorophenyl)-4-bromo-isoxazole-3-carboxylic acid ethylamide (0.507 g, 0.94 mmol) was added sodium hydrogen carbonate (237 mg, 2.82 mmol) followed by DMF (5 mL) and water (1.0 mL). The mixture was degassed by evacuation and flushing with nitrogen (three times), followed by bubbling nitrogen gas through mixture for five minutes. Dichlorobis(triphenylphosphine)palladium (II) (66 mg, 0.094 mmol) was added and reaction mixture was heated under a nitrogen atmosphere at 90° C. for two hours (reaction mixture becomes dark brown in colour). Another 10 mg of dichlorobis(triphenylphosphine)palladium (II) was added and reaction mixture was heated at 90° C. for 15 hours then allowed to cool to ambient temperature. The majority of solvents were removed in vacuo and the residue was partitioned between ethyl acetate (50 mL) and water (50 mL). This mixture was filtered through a pad of celite to remove palladium residues and then the phases were separated and the organic phase was washed with water (2×30 mL), saturated aqueous sodium chloride solution (50 mL) then dried over sodium sulphate. The mixture was filtered and the filtrate solvents were removed in vacuo to afford a yellow oil (598 mg). The crude reaction product was purified by adsorption onto silica gel then flash chromatography on silica gel (20 g IST) eluting with a solvent gradient of 1 to 20% ethyl acetate in hexane. This affords 5-(2,4-Bis-benzyloxy-5-chlorophenyl)-4-(4-methoxy-phenyl)-isoxazole-3-carboxylic acid ethylamide as a colourless solid (0.223 g, 40%). LCMS: [M+H]$^+$ 571, 569 ($^{37}$Cl; $^{35}$Cl). $^1$H NMR (400 MHz, CDCl$_3$) δ 1.21 (t, 3H), 3.44 (m, 2H), 3.79 (s, 3H), 4.73 (s, 2H), 6.45 (s, 1H), 6.65 (t, 1H), 6.80 (d, 2H), 7.14 to 7.44 (m, 8H), 6.95 (m 2H).

Step 8

5-(5-chloro-2,4-dihydroxyphenyl)-4-(4-methoxy-phenyl)-isoxazole-3-carboxylic acid ethylamide

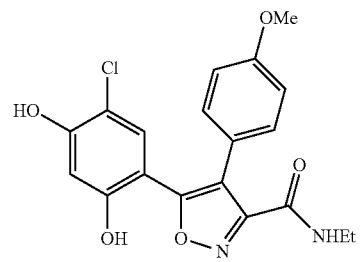

To an ice-bath cooled solution of 5-(2,4-Bis-benzyloxy-5-chlorophenyl)-4-(4-methoxy-phenyl)-isoxazole-3-carboxylic acid ethylamide (0.213 mg, 0.374 mmol) in dichloromethane (5 mL) under a nitrogen atmosphere was added a 1.0M solution of Boron trichloride in dichloromethane (1.12 mL; 1.12 mmol). The reaction mixture was stirred at 0° C. for 15 minutes then at ambient temperature for 35 minutes. The reaction mixture was re-cooled to 0° C. and quenched by the addition of saturated aqueous sodium hydrogen carbonate solution (5 mL). After stirring for 5 minutes the dichloromethane was removed in vacuo and the residue was partitioned between ethyl acetate (30 mL) and water (30 mL). The phases were separated and the organic phase was washed with water (30 mL), saturated sodium chloride solution (30 mL) then dried over sodium sulphate. The mixture was filtered and the filtrate solvents were removed in vacuo to afford a foam-like colourless solid which was purified by adsorption onto silica gel then flash chromatography on silica gel (10 g IST) eluting with 50% ethyl acetate in hexane. This affords 5-(5-chloro-2,4-dihydroxyphenyl)-4-(4-methoxy-phenyl)-isoxazole-3-carboxylic acid ethylamide as a colourless solid (0.097 g; 67%). LCMS: [M+H]+ 391, 389 ($^{37}$Cl; $^{35}$Cl). $^1$H NMR (400 MHz, d$_6$-DMSO) ☐ 1.08 (t, 3H), 3.22 (m, 2H), 3.73 (s, 3H), 6.59 (s 1H), 6.87 (d, 1H), 7.13-7.17 (m, 3H), 8.88 (br t, 1H), 10.09 (s, 1H), 10.62 (s, 1H).

Example 25 had activity 'A' in the Fluorescence Polarisation Assay, as described below.

Similarly, Example 26 was prepared by coupling the Boc protected 4-piperazinophenyl boronate ester as above. This boronate ester was made from 1-(4-bromophenyl)piperazine by boc protection followed by boronate ester formation by Pd-catalysed coupling with bis(tetramethylpinacolato) diboron. Example 27 was made similarly. Example 27a was made by deprotection of 5-(2,4-Bis-benzyloxy-5-chlorophenyl)-4-bromo-isoxazole-3-carboxylic acid ethylamide:

| Example | Structure | MH+ | Hsp90 IC50* |
|---|---|---|---|
| 26 | | 443 | A |
| 27 | 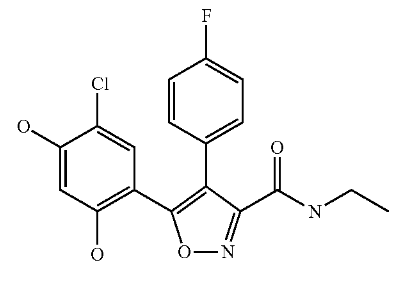 [SMILES: CCNC(=O)c1noc(-c2cc(Cl)c(O)cc2O)c1-c1ccc(F)cc1] | 377 | A |
| 27a | 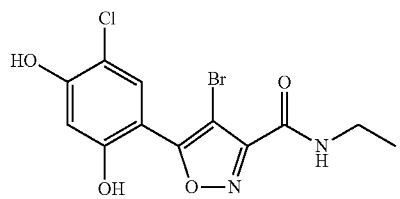 [SMILES: CCNC(=O)c1noc(-c2cc(Cl)c(O)cc2O)c1Br] | 362 | A |

*Fluorescence Polarisation Assay

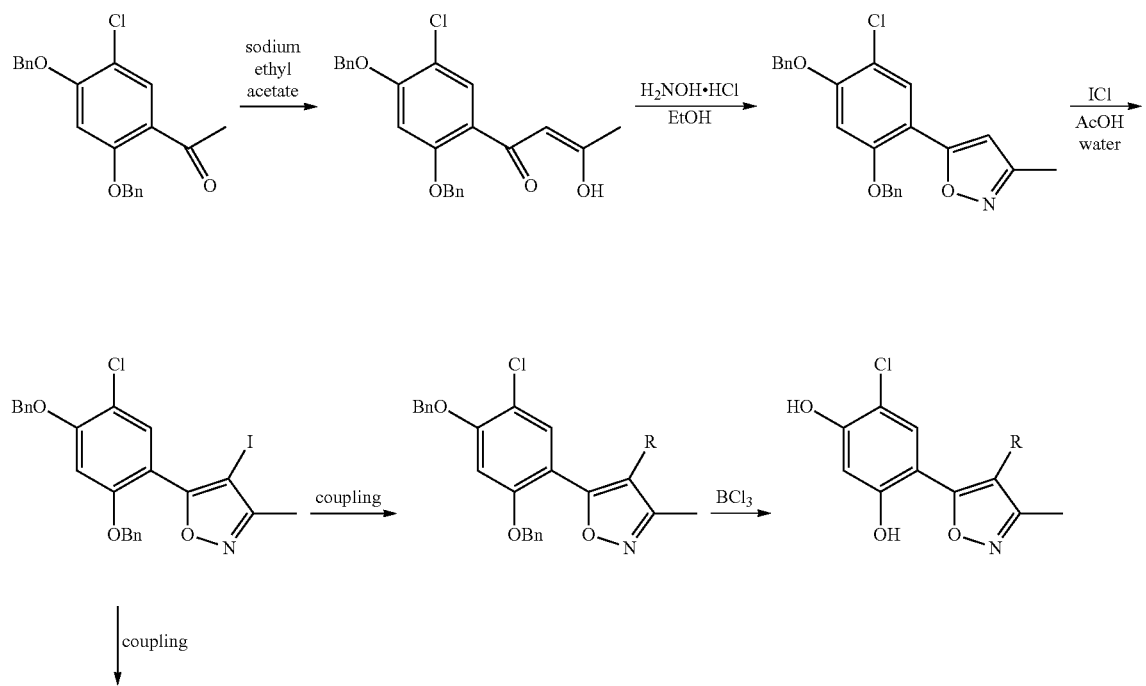

Scheme 7: Peparation of 5-(2,4-bis-benzyloxy-5-chloro-phenyl)-4-iodo-3-methyl-isoxazole intermediate

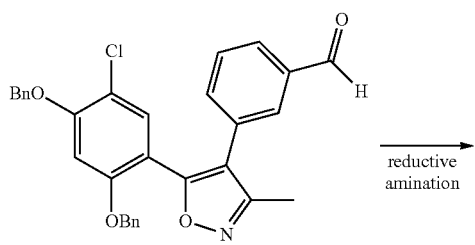 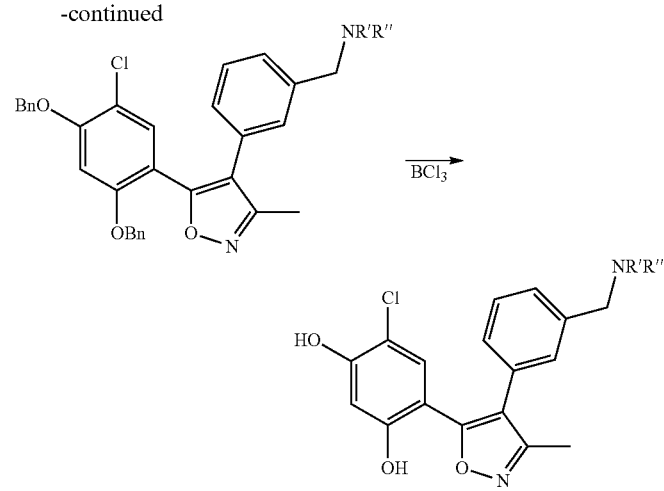

Example 28

4-Chloro-6-[3-methyl-4-(3-morpholin-4-ylmethyl-phenyl)-isoxazol-5-yl]-benzene-1,3-diol

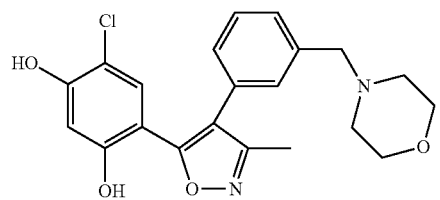 [SMILES: Cc1noc(-c2cc(Cl)c(O)cc2O)c1-c1cccc(CN2CCOCC2)c1]

Step 1

1-(2,4-Bis-benzyloxy-5-chloro-phenyl)-3-hydroxy-but-2-en-1-one

To a solution of ketone (15 g) in EtOAc (200 ml) was added sodium metal (3.0 g) in small pieces. The suspension was stirred at room temperature for 15 mins, then heated to reflux overnight. The reaction was quenched with acetic acid, and the yellow precipitate filtered. This was triturated in hexanes to give bright yellow crystals. NMR indicated this was the required product—mostly in enol form—small trace of keto form.

Step 2

5-(2,4-Bis-benzyloxy-5-chloro-phenyl)-3-methyl-isoxazole

The diketone (4.0 g) was suspended in 80% aq EtOH. Hydroxylamine hydrochloride (3.4 g) and sodium acetate (4.0 g) was added and the pH adjusted to 8/9 with 2M NaOH. The solution was refluxed for 24 hrs (difficult to monitor by TLC due to very similar $R_f$ values). After this time the solution was acidified to pH 5 with 1M HCl and poured into water. The white precipitate was filtered, washed with water, and triturated with hexane to give a white solid. Notes; Compound can also be washed with ether if necessary to remove trace impurities but not usually required. NMR indicated this to be the required product.

Step 3

5-(2,4-Bis-benzyloxy-5-chloro-phenyl)-4-iodo-3-methyl-isoxazole

Isoxazole (2 g) was placed in a mixture of acetic acid (24 ml) and water (30 ml). Iodinemonochloride (2 g excess) was added and the solution heated at 80° C. for 2-3 hrs. After cooling to room temperature 10% $Na_2SO_3$ (Sodium sulphite) in water was added (50 ml). A viscous orange solid/oil was separated from the mixture and was washed with water. It was then dissolved in acetone and filtered. Removal of the acetone under vacuum gave a sticky orange oil which solidified to a orange solid overnight. NMR and LCMS indicated this was the required product.

Step 4

3-[5-(2,4-Bis-benzyloxy-5-chloro-phenyl)-3-methyl-isoxazol-4-yl]-benzaldehyde

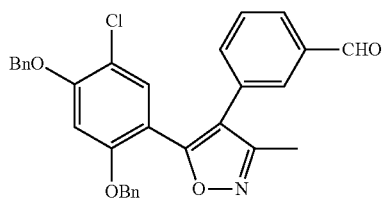 [SMILES: Cc1noc(-c2cc(Cl)c(OCc3ccccc3)cc2OCc2ccccc2)c1-c1cccc(C=O)c1]

5-(2,4-Bis-benzyloxy-5-chloro-phenyl)-4-iodo-3-methyl-isoxazole (200 mg, 0.38 mmol), and 3-formylbenzene boronic acid (85 mg, 1.5 equiv.) were dissolved in DMF (12 ml) before 1M Sodium hydrogen carbonate solution (1.1 ml, 3.0 equiv) and $Pd(Ph_3P)_2Cl_2$ (21 mg, 0.08 equiv.) were added with stirring. The reaction mixture was transferred to three microwave tubes which were sealed and the mixtures within degassed before being irradiated by an initial power of 200 W to a temperature of 150° C. for 15 minutes in a CEM microwave apparatus. Upon cooling the reaction mixtures were combined and partitioned between ethyl acetate (10 ml) and water (10 ml). The aqueous layer was separated and extracted again with ethyl acetate (10 ml). The organics were then combined washed with water (2×20 ml), brine (20 ml), dried over $Na_2SO_4$ before being condensed in vaccuo and purified by flash chromatography on silica gel, eluting with 25% ethyl acetate in hexane.

LCMS $t_R$=9.06, MS m/z 510.4 [M+H]$^+$

Step 5

4-{3-[5-(2,4-Bis-benzyloxy-5-chloro-phenyl)-3-methyl-isoxazol-4-yl]-benzyl}-morpholine

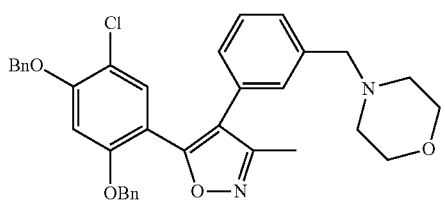 [SMILES: Cc1noc(-c2cc(Cl)c(OCc3ccccc3)cc2OCc2ccccc2)c1-c1cccc(CN2CCOCC2)c1]

3-[5-(2,4-Bis-benzyloxy-5-chloro-phenyl)-3-methyl-isoxazol-4-yl]-benzaldehyde (25 mg, 0.05 mmol) and morpholine (0.3 ml) were mixed with DCE (0.5 ml) in an microwave tube. Sodium triacetoxyborohydride (15 mg, 1.4 equiv) was added, the tube sealed, and nitrogen atmosphere introduced. After 1 hr more sodium triacetoxyborohydride (15 mg) was added and the reaction left stirring overnight. TLC analysis showed that the reaction had not gone to completion so a drop of acetic acid was added and the reaction again left stirring overnight after which the reaction was quenched with 1M NaHCO$_3$ solution (7 ml) and extracted into EtOAc (5 ml). This was dried over MgSO$_4$ and the solvent removed in vaccuo to provide 13 mg of the crude product as an off white powder which was taken over to the deprotection step.

Step 6

4-Chloro-6-[3-methyl-4-(3-morpholin-4-ylmethyl-phenyl)-isoxazol-5-yl]-benzene-1,3-diol

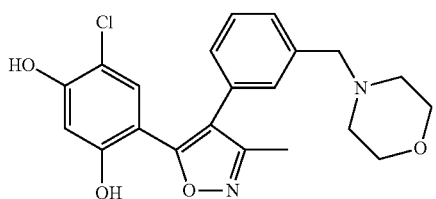 [SMILES: Cc1noc(-c2cc(Cl)c(O)cc2O)c1-c1cccc(CN2CCOCC2)c1]

4-{3-[5-(2,4-Bis-benzyloxy-5-chloro-phenyl)-3-methyl-isoxazol-4-yl]-benzyl}-morpholine was deprotected as previously shown and the crude purified by preparative TLC eluting with 10% Ethanol in dichloromethane to provide 0.6 mg (7% yield) of the product as a white powder.

LCMS $t_R$=5.46, MS m/z 399.3 [M−H]$^−$

Example 28 had activity 'A' in the Fluorescence Polarisation Assay, as described below.

Example 29

1-{3-[5-(2,4-Bis-benzyloxy-5-chloro-phenyl)-3-methyl-isoxazol-4-yl]-benzyl}-piperidine-4-carboxylic acid amide

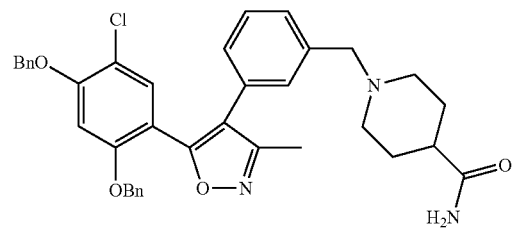 [SMILES: Cc1noc(-c2cc(Cl)c(OCc3ccccc3)cc2OCc2ccccc2)c1-c1cccc(CN2CCC(C(N)=O)CC2)c1]

Prepared in using a similar procedure to 4-chloro-6-[3-methyl-4-(3-morpholin-4-ylmethyl-phenyl)-isoxazol-5-yl]-benzene-1,3-diol except that isonipecotamide replaced the morpholine and the sodium triacetoxyborohydride (3 equiv.) and acetic acid (1 drop) were added initially. The reaction was complete after 18 hrs and the crude obtained after work up was taken over to the deprotection step.

1-{3-[5-(5-Chloro-2,4-dihydroxy-phenyl)-3-methyl-isoxazol-4-yl]-benzyl}-piperidine-4-carboxylic acid amide

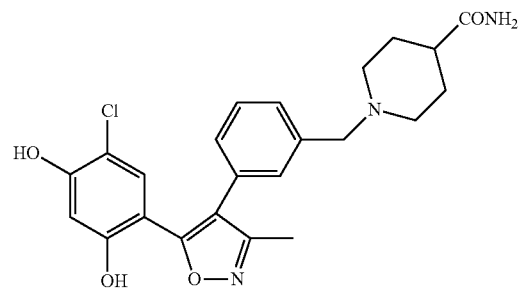 [SMILES: Cc1noc(-c2cc(Cl)c(O)cc2O)c1-c1cccc(CN2CCC(C(N)=O)CC2)c1]

1-{3-[5-(2,4-Bis-benzyloxy-5-chloro-phenyl)-3-methyl-isoxazol-4-yl]-benzyl}-piperidine-4-carboxylic acid amide was deprotected as previously shown and the crude purified by preparative TLC eluting with 10% Ethanol in dichloromethane to provide 0.7 mg (3% yield) of the product as a white powder.

LCMS $t_R$=5.36, MS m/z 442.3 [M+H]$^+$

Example 29 had activity 'A' in the Fluorescence Polarisation Assay, as described below.

In a similar way, example 30 was prepared:

| Example | Structure | MH+ | Hsp90 IC50 |
|---------|-----------|-----|------------|
| 30 | ![structure] | 359 | A* |

*Fluorescence Polarisation Assay

Example 31

Scheme 8:

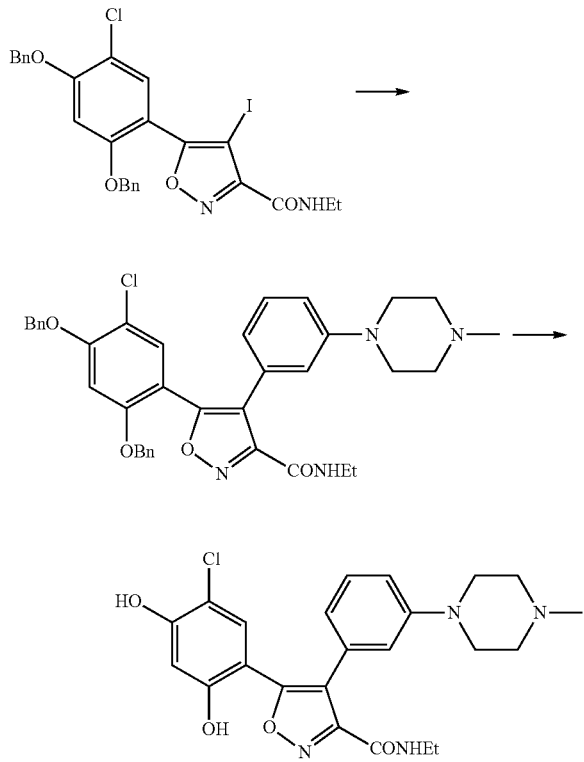

Step 1

5-(2,4-Bis-benzyloxy-5-chloro-phenyl)-4-iodo-isoxazole-3-carboxylic acid ethylamide

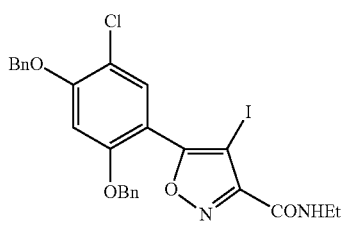

5-(2,4-Bis-benzyloxy-5-chloro-phenyl)-isoxazole-3-carboxylic acid ethylamide (0.90 g, 1.94 mmol), N-Iodosuccinimide (0.44 g, 1 equiv.) and Ammonium cerium (IV) nitrate (0.53 g, 0.5 equiv) were suspended in Acetonitrile (55 ml) before heating to reflux (oil bath 100° C.) where upon the mixture became homogeneous. After 18 hrs the solution was cooled and the solvent removed in vaccuo to give a thick orange oil. This was partitioned between DCM (25 ml) and water (10 ml), the organic layer was kept and washed with brine (2×25 ml) before drying over Na2SO4. The DCM was removed in vaccuo to provide 0.88 g (77% yield) of the product as a orange/tan coloured powder.

LCMS $t_R$=8.75, MS m/z 589.1 [M+H]$^+$

Step 2

1-(3-Bromo-phenyl)-4-methyl-piperazine

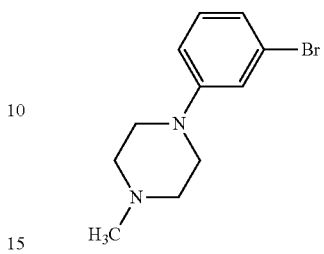

1,3-Dibromobenzene (0.90 ml, 7.49 mmol), N-methylpiperazine (0.28 ml, 2.50 mmol) and anhydrous toluene (7 ml) were added by syringe to a dry, argon filled flask. The solution was thoroughly mixed before BINAP (47 mg) and Pd$_2$ dba$_3$ (23 mg) were delivered and the flask refilled with Argon and DBU (0.93 g, 2.5 equiv.) added via syringe. The reaction mixture was warmed to 60° C. before freshly ground sodium tertbutoxide was added in one portion to start the reaction. The reaction was left stirring at 60° C. overnight and the TLC analysis appeared to show that some piperazine was still present so the reaction was heated to 100° C. and stirred for another 24 hrs after which it was partitioned between EtOAc (20 ml) and water (20 ml). The aqueous layer was extracted again with EtOAc and the combined organics were washed with 1.6M HCl solution (2×10 ml). The acidic solution containing the product was then basified first with a similar volume of 1M NaOH solution to acid solution and then carefully solid sodium bicarbonate was added to make the pH=8.5 before extraction back into EtOAc (2×15 ml), which was washed with brine, dried over MgSO$_4$ and evaporated to dryness to provide 0.50 g (78% yield) of the pure product as a yellow oil.

LCMS $t_R$=4.55, MS m/z 255.4/257.3 [M+H]$^+$

Step 3

1-Methyl-4-[3-(4,4,5,5-tetramethyl-[1,3,2]dioxaborolan-2-yl)-phenyl]-piperazine

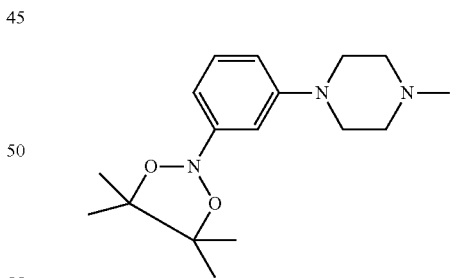

To a solution of PdCl$_2$ (dppf).DCM (10 mg, 0.012 mmol) in anhydrous toluene (4 ml) in an argon filled sealed microwave tube was added the 1-(3-Bromo-phenyl)-4-methyl-piperazine (100 mg, 0.39 mmol), Et$_3$N (0.11 ml, 2 equiv.), and 4,4,5,5-tetramethyl-1,3,2-dioxaborolane (0.09 ml, 1.5 equiv). The microwave tube was evacuated and backfilled with Argon before being irradiated in a CEM Microwave reactor at 100° C. for 1 hr using an initial power of 200 W. The reaction mixture was partitioned between more toluene (6 ml) and water (10 ml), the organic layer separated, washed with water (1×10 ml), dried over MgSO$_4$ and then evaporated in vacuo to leave a purple/brown residue which was used for suzuki coupling without further purification.

LCMS $t_R$=0.97, MS m/z 303.5 [M+H]$^+$

Step 4

5-(2,4-Bis-benzyloxy-5-chloro-phenyl)-4-[3-(4-methyl-piperazin-1-yl)-phenyl]-isoxazole-3-carboxylic acid ethylamide

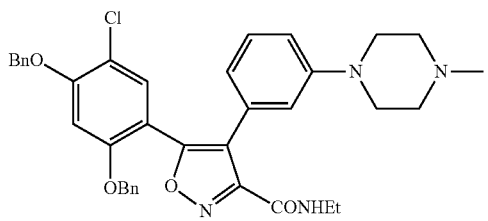

5-(2,4-Bis-benzyloxy-5-chloro-phenyl)-4-bromo-isoxazole-3-carboxylic acid ethylamide (38 mg, 0.07 mmol) and 1-Methyl-4-[3-(4,4,5,5-tetramethyl-[1,3,2]dioxaborolan-2-yl)-phenyl]-piperazine (31 mg, 2 equiv.) were coupled together using the suzuki method previously described to provide 37 mg (83% yield) of the crude as a brown oil which was taken on to the deprotection step.

Step 5

5-(5-Chloro-2,4-dihydroxy-phenyl)-4-[3-(4-methyl-piperazin-1-yl)-phenyl]-isoxazole-3-carboxylic acid ethylamide

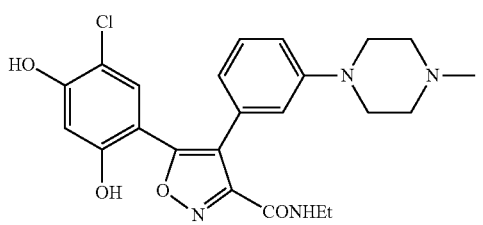

5-(2,4-Bis-benzyloxy-5-chloro-phenyl)-4-[3-(4-methyl-piperazin-1-yl)-phenyl]-isoxazole-3-carboxylic acid ethylamide was deprotected as previously shown. The precipitate formed during the reaction was separated, partitioned between EtOAc and water. The aqueous layer was kept, basified using solid sodium hydrogen carbonate and the product extracted using EtOAc (2×10 ml). The combined organics were washed with brine (10 ml) dried over MgSO$_4$ and evaporated in vaccuo to provide 5.2 mg (20% yield) of product as a tan coloured powder.

LCMS $t_R$=5.58, MS m/z 457.3 [M+H]$^+$ $\delta_H$ (d$^4$-MeOH), 7.17 (1H, m, Ar—H), 7.09 (1H, s, Ar—H), 6.94 (1H, m, Ar—H), 6.80 (1H, m, Ar—H), 6.49 (1H, s, Ar—H), 3.13 (4H, t, NCH$_2$CH$_2$N—CH$_3$), 2.69 (2H, q, CONHCH$_2$CH$_3$), 2.61 (4H, t, NCH$_2$CH$_2$N—CH$_3$), 2.37 (3H, s, NCH$_2$CH$_2$N—CH$_3$), 1.19 (3H, t, CONHCH$_2$CH$_3$).

Example 31 had activity 'A' in the Fluorescence Polarisation Assay, as described below.

Examples 32-38 in the Table below were prepared similarly, but with the following variations:

1. For Example 36, the dioxaborolan intermediate was prepared as follows:

Scheme

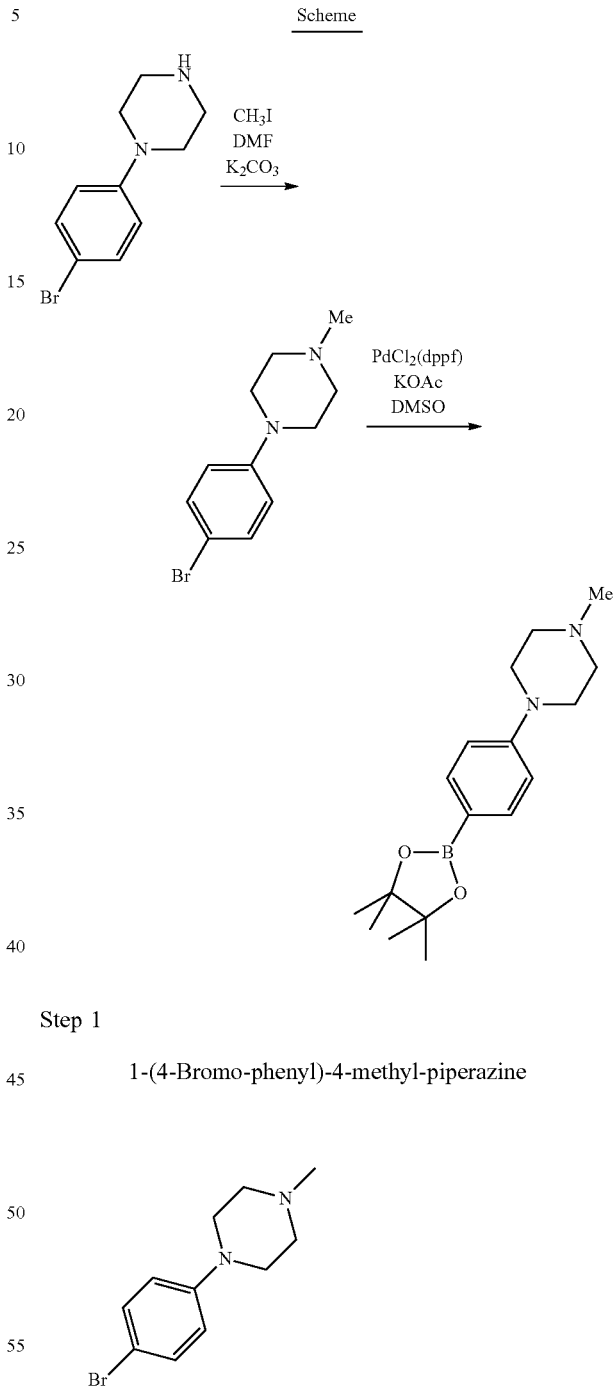

Step 1

1-(4-Bromo-phenyl)-4-methyl-piperazine 1-(4-Bromo-phenyl)-piperazine (1 g, 4.1 mmol) and potassium carbonate (1.8 g, 3 eq) in DMF (15 ml) treated with methyl iodide (250 µl, 1.1 equivalents), solution stirred at room temperature overnight. Reaction quenched with deionised water (10 ml), extracted with ethyl acetate. Organic phase washed with sodium hydrogen carbonate to remove any dimethylated impurity, dried and solvent removed to give 1-(4-Bromo-phenyl)-4-methyl-piperazine in 73% yield.

LC retention time 2.21 minutes [M+H]+ 256 (Run time 3.75 mins).

Step 2

1-Methyl-4-[4-(4,4,5,5-tetramethyl-[1,3,2]dioxaborolan-2-yl)-phenyl]-piperazine

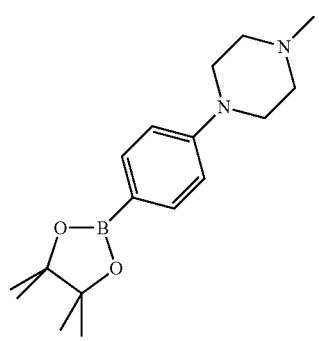

1-(4-Bromo-phenyl)-4-methyl-piperazine (750 mg, 3 mmol) in DMSO (15 ml) with bis(pinacolato)diboran (1.1 g, 1.5 equivalents) and potassium acetate (900 mg, 3 equivalents). Suspension degassed before treatment with PdCl$_2$(dppf) (cat.), stirred at 80 C. Additional bis(pinacolato)diboran (1 eq) added after 3 hours, stirred for a further 2 hours. Suspension partitioned between ethyl acetate and water. Purification by column chromatography 0-8% methanol gradient in dichloromethane to give 1-Methyl-4-[4-(4,4,5,5-tetramethyl-[1,3,2]dioxaborolan-2-yl)-phenyl]-piperazine in 62% yield.

LC retention time 1.83 minutes [M+H]+ 303 (Run time 3.75 mins).

2. For examples 37 and 38, a boronic acid intermediate was used instead of a diaoxaborolan, the former being prepared as follows:

4-[(2-Methylsulfonyl)-ethylaminomethyl]-phenyl boronic acid (intermediate for Example 37)

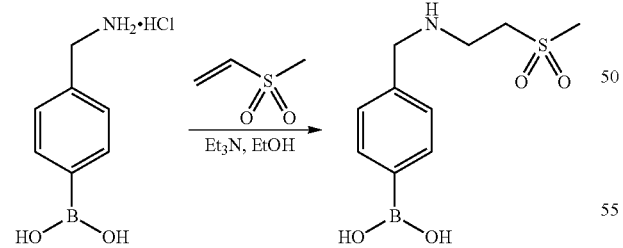

4-Aminomethyl phenyl boronic acid hydrochloride (560 mg, 3 mmol) in ethanol (5 ml) was treated with methyl vinyl sulfone (260 μl, 1 equivalent) and triethyl amine (1.2 ml, 3 equivalents). The solution was stirred at 100° C. for 2 hrs. Ethanol removed under vacuum, partitioned in water and butanol to give 4-[(2-methylsulfonyl)-ethylaminomethyl]-phenyl boronic acid in 94% yield.

LC retention time 0.39 minutes [M+H]+ 258 (Run time 3.75 mins).

4-[N-methy S,S-dioxo-thiomorpholino]-phenyl boronic acid (Intermediate for Example 38)

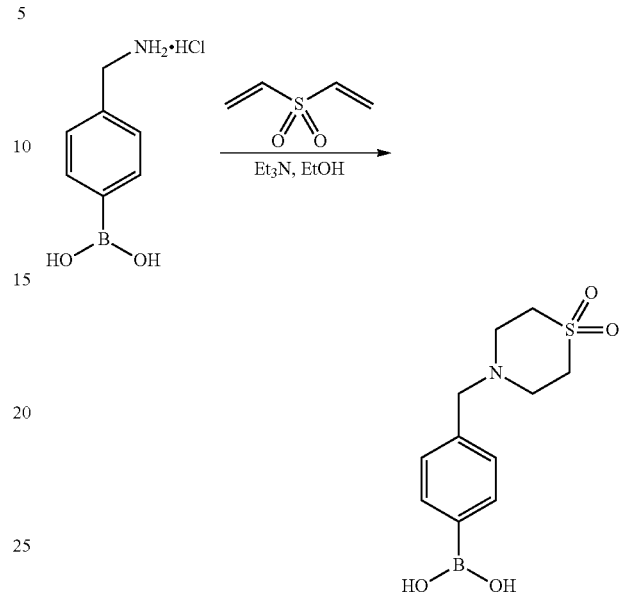

4-Aminomethyl phenyl boronic acid hydrochloride (456 mg, 2.4 mmol) in ethanol (8 ml) treated with vinyl sulfone (244 μl, 1 equivalent) and triethylamine (2 equivalents), solution stirred at 10° C. for 3 hrs. Ethanol removed under vacuum, partitioned in water and butanol to give the product in 88% yield.

LC retention time 1.65 minutes [M+H]+ 270 (Run time 8 mins).

| Example | Structure | MH+ | Hsp90 IC50* |
|---|---|---|---|
| 32 | 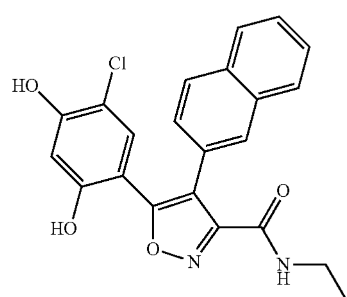 | 409 411 | A |
| 33 | 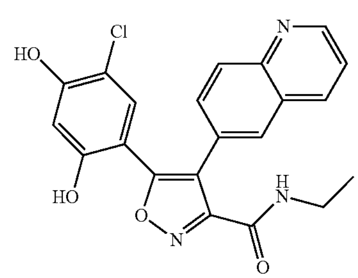 [SMILES: CCNC(=O)c1noc(-c2cc(Cl)c(O)cc2O)c1-c1ccc2ncccc2c1] | 410 412 | A |

51
-continued

| Example | Structure | MH+ | Hsp90 IC50* |
|---|---|---|---|
| 34 | 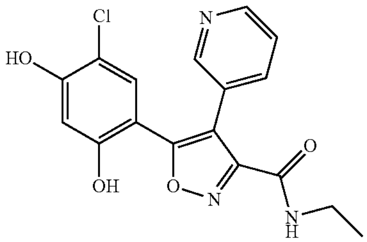 [SMILES: CCNC(=O)c1noc(-c2cc(Cl)c(O)cc2O)c1-c1cccnc1] | 360, 362 | A |
| 35 | 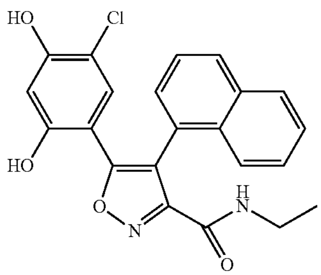 [SMILES: CCNC(=O)c1noc(-c2cc(Cl)c(O)cc2O)c1-c1cccc2ccccc12] | 409, 411 | A |
| 36 | 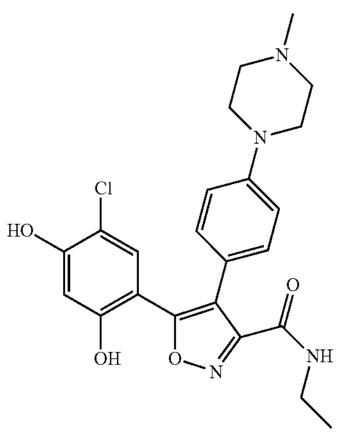 [SMILES: CCNC(=O)c1noc(-c2cc(Cl)c(O)cc2O)c1-c1ccc(N2CCN(C)CC2)cc1] | 457, 459 | A |
| 37 | 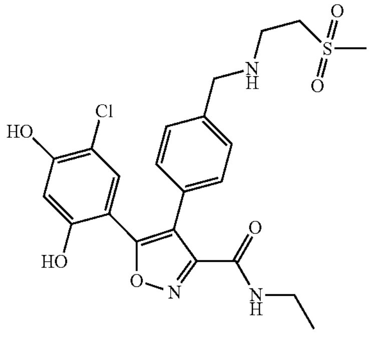 [SMILES: CCNC(=O)c1noc(-c2cc(Cl)c(O)cc2O)c1-c1ccc(CNCCS(C)(=O)=O)cc1] | 494, 496 | A |

52
-continued

| Example | Structure | MH+ | Hsp90 IC50* |
|---|---|---|---|
| 38 | 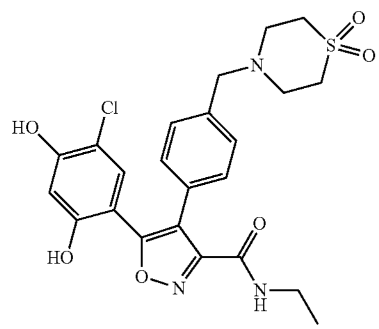 [SMILES: CCNC(=O)c1noc(-c2cc(Cl)c(O)cc2O)c1-c1ccc(CN2CCS(=O)(=O)CC2)cc1] | 506, 508 | A |

Example 39

Scheme 9:

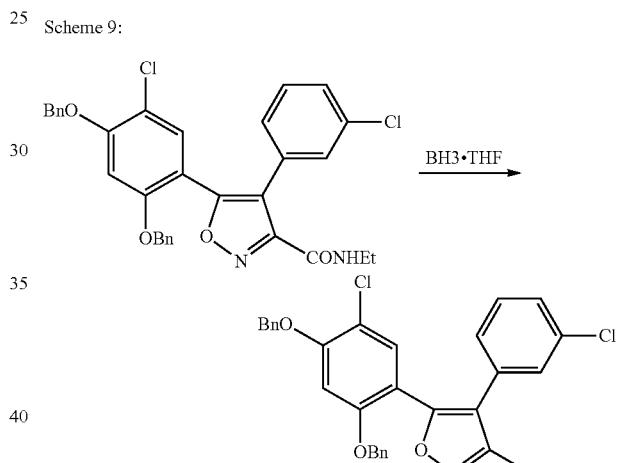

Step 1

5-(2,4-Bis-benzyloxy-5-chloro-phenyl)-4-(3-chloro-phenyl)-isoxazole-3-carboxylic acid ethylamide 5-(2,4-Bis-benzyloxy-5-chloro-phenyl)-4-bromo-isoxazole-3-carboxylic acid ethylamide (60 mg, 0.11 mmol), and 3-chlorobenzene boronic acid (23 mg, 1.3 equiv.) were coupled together using the suzuki method previously described to provide 35 mg (55% yield) of the crude as a brown powder which was taken on to the next step.

Step 2

[5-(2,4-Bis-benzyloxy-5-chloro-phenyl)-4-(3-chloro-phenyl)-isoxazol-3-ylmethyl]-ethyl-amine

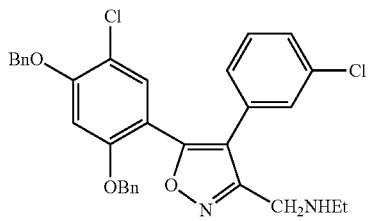

To a solution of 5-(2,4-Bis-benzyloxy-5-chloro-phenyl)-4-(3-chloro-phenyl)-isoxazole-3-carboxylic acid ethylamide (36 mg, 0.06 mmol) in anhydrous THF under argon was added 1M Borane-THF complex (1 ml) and the solution refluxed overnight. After cooling the solution was poured on to a Isolute® SPE Flash SCX-2 5 g column which was quickly eluted with methanol (2×20 ml). The desired product was then recovered by eluting with a mixture of 10% ammonia in methanol (2×10 ml) which was evaporated in vaccuo to provide 23 mg (65% yield) of a light yellow powder.

LCMS (LCT) $t_R$=8.18, MS m/z 558.8 [M+H]$^+$

Example 39 had activity 'A' in the Fluorescence Polarisation Assay, as described below.

Example 40 was similarly prepared:

| Example | Structure | MH+ | Hsp90 IC50* |
|---|---|---|---|
| 40 | 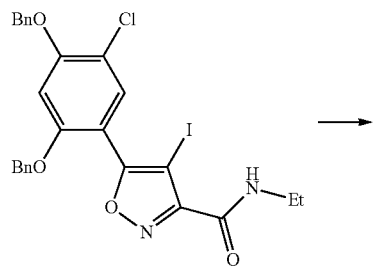 | 375 377 | A |

*Fluorescence Polarisation Assay

Example 41

Scheme 10:

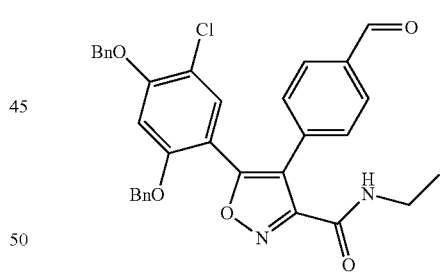

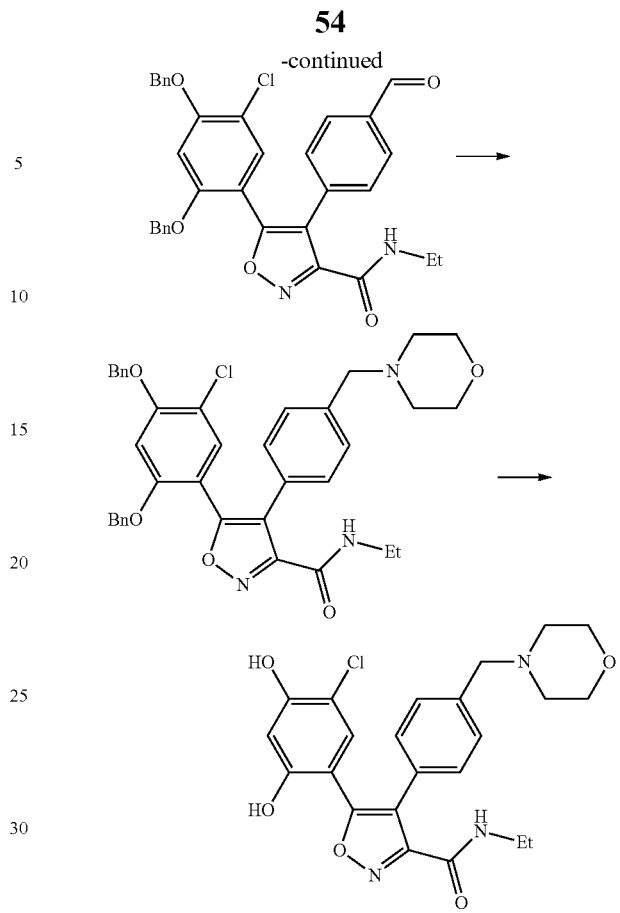

Step 1

5-(2,4-Bis-benzyloxy-5-chloro-phenyl)-4-(4-formyl-phenyl)-isoxazole-3-carboxylic acid ethylamide 5-(2,4-Bis-benzyloxy-5-chloro-phenyl)-4-iodo-isoxazole-3-carboxylic acid ethylamide (prepared as for Example 31) (2 g, 3.4 mmol), 4-formylboronic acid (0.612 g, 4.08 mmol), NaHCO₃ (10.2 ml, 1M aq. solution, 10.2 mmol), PdCl₂(PPh₃)₂ (119 mg, 0.17 mmol) and DMF (50 ml) were combined. The mixture was then degassed by bubbling N₂ through it for 5 minutes before being heated at 80° C. for 1 hour. The mixture was then evaporated in vacuo and partitioned between EtOAc (3×50 ml) and water (50 ml). The combined, dried (Na₂SO₄) organics were evaporated in vacuo to give a crude oil. This was dissolved in EtOAc and passed through a plug of SiO₂, washing through with EtOAc. The filtrate was evaporated in vacuo and the resulting oil triturated with Et₂O to afford 5-(2,4-Bis-benzyloxy-5-chloro-phenyl)-4-(4-formyl-phenyl)-isoxazole-3-carboxylic acid ethylamide (1.577 g, 82%) as a pale coloured solid, LC/MS: RT=2.908 min. 567.3 (MH+).

Step 2

5-(2,4-Bis-benzyloxy-5-chloro-phenyl)-4-(4-morpholin-4-ylmethyl-phenyl)-isoxazole-3-carboxylic acid ethylamide

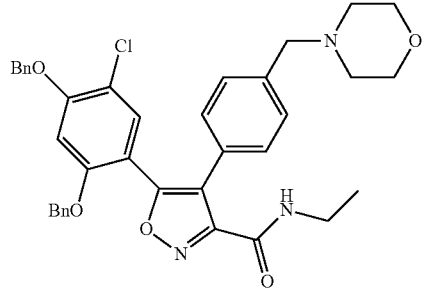 [SMILES: CCNC(=O)c1noc(-c2cc(Cl)c(OCc3ccccc3)cc2OCc2ccccc2)c1-c1ccc(CN2CCOCC2)cc1]

Acetic acid (0.37 ml, 6.44 mmol) was added dropwise to a mixture of 5-(2,4-Bis-benzyloxy-5-chloro-phenyl)-4-(4-formyl-phenyl)-isoxazole-3-carboxylic acid ethylamide (730 mg, 1.29 mmol), morpholine (0.225 ml, 2.58 mmol), 3 A powdered molecular sieves (730 mg) and MeOH (21 ml). This was left to stir overnight under $N_2$. The mixture was then evaporated in vacuo and the resultant crude partitioned between $CH_2Cl_2$ (3×40 ml) and sat. $NaHCO_3$ solution (40 ml). The combined, dried ($Na_2SO_4$) organics were evaporated in vacuo to give crude 5-(2,4-Bis-benzyloxy-5-chloro-phenyl)-4-(4-morpholin-4-ylmethyl-phenyl)-isoxazole-3-carboxylic acid ethylamide (810 mg) as a yellow solid, LC/MS: RT=2.365 min. 638.4 (MH+).

Step 3

5-(5-Chloro-2,4-dihydroxy-phenyl)-4-(4-morpholin-4-ylmethyl-phenyl)-isoxazole-3-carboxylic acid ethylamide

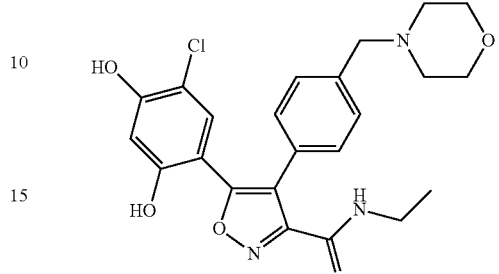

$BCl_3$ (1M sol. in $CH_2Cl_2$, 3.87 ml, 3.87 mmol) was added dropwise to a solution of the crude 5-(2,4-Bis-benzyloxy-5-chloro-phenyl)-4-(4-morpholin-4-ylmethyl-phenyl)-isoxazole-3-carboxylic acid ethylamide (810 mg, ~1.29 mmol) in $CH_2Cl_2$ (30 ml) at 0° C. The reaction was then allowed to reach RT. Saturated aqueous $NaHCO_3$ (40 ml) was then added slowly and the resultant mixture concentrated in vacuo. This was then partitioned between EtOAc (3×50 ml) and water (50 ml). The combined, dried ($Na_2SO_4$) organics were evaporated in vacuo. Flash chromatography eluting with $CH_2Cl_2$-10% MeOH/1% $NH_3/CH_2Cl_2$ afforded 5-(5-Chloro-2,4-dihydroxy-phenyl)-4-(4-morpholin-4-ylmethyl-phenyl)-isoxazole-3-carboxylic acid ethylamide (380 mg, 64% over 2 steps) as a yellow foam, LC/MS: RT=1.751 min. 458.2 (MH+).

Example 41 had activity 'A' in the Fluorescence Polarisation Assay, as described below.

In the following Table, Examples 42-64 were prepared by methods analogous to Example 41, using the appropriate aldehyde or ketone.

| Example | Structure | MH+ | Hsp90 IC50* |
|---|---|---|---|
| 42 | 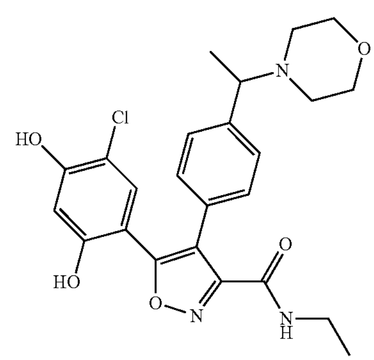 [SMILES: CCNC(=O)c1noc(-c2cc(Cl)c(O)cc2O)c1-c1ccc(C(C)N2CCOCC2)cc1] | 472 474 | A |

-continued

| Example | Structure | MH+ | Hsp90 IC50* |
|---|---|---|---|
| 43 | 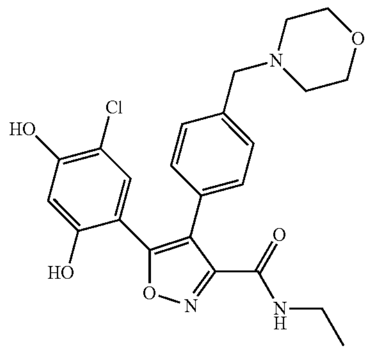 [SMILES: CCNC(=O)c1noc(-c2cc(Cl)c(O)cc2O)c1-c1ccc(CN2CCOCC2)cc1] | 458, 460 | A |
| 44 | 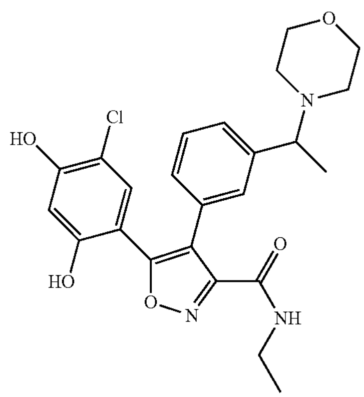 [SMILES: CCNC(=O)c1noc(-c2cc(Cl)c(O)cc2O)c1-c1cccc(C(C)N2CCOCC2)c1] | 472, 474 | A |
| 45 | 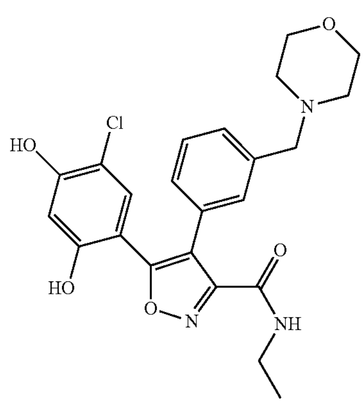 [SMILES: CCNC(=O)c1noc(-c2cc(Cl)c(O)cc2O)c1-c1cccc(CN2CCOCC2)c1] | 458 | A |
| 46 | 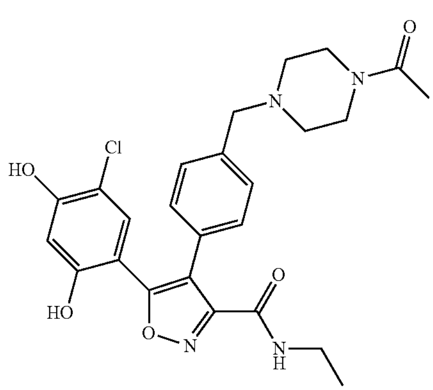 [SMILES: CCNC(=O)c1noc(-c2cc(Cl)c(O)cc2O)c1-c1ccc(CN2CCN(C(C)=O)CC2)cc1] | 499, 501 | A |

-continued
| Example | Structure | MH+ | Hsp90 IC50* |
|---|---|---|---|
| 47 | 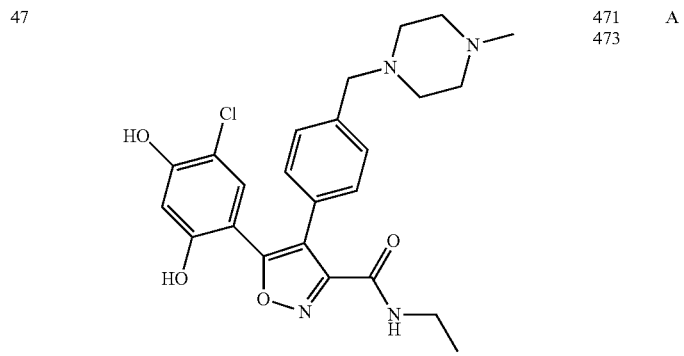 | 471 473 | A |
| 48 | 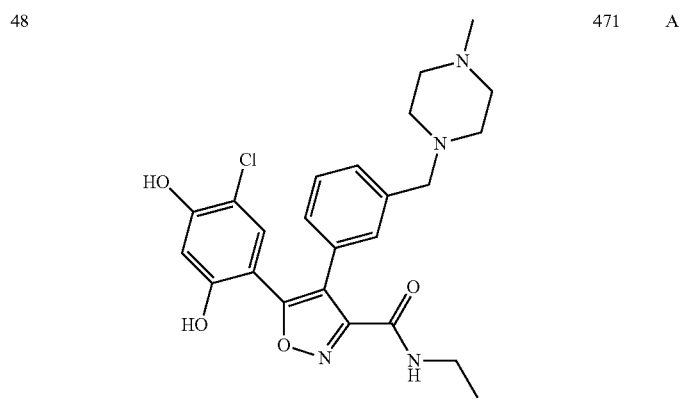 | 471 | A |
| 49 | 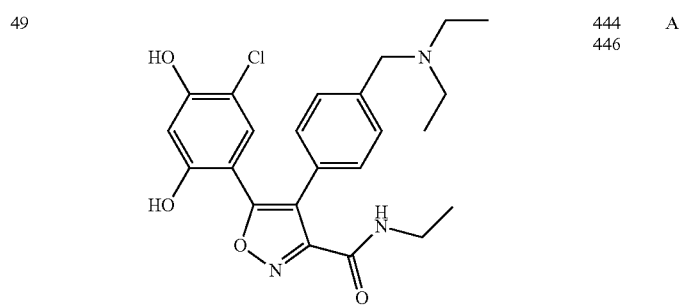 | 444 446 | A |
| 50 | 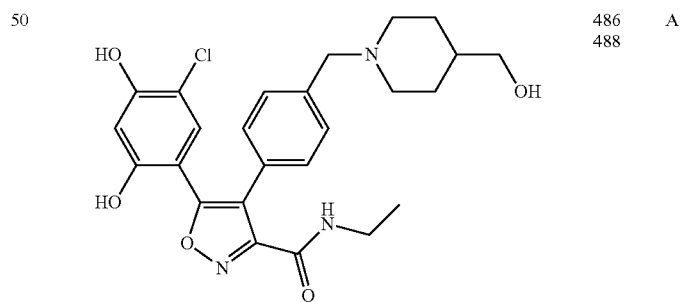 | 486 488 | A |

-continued

| Example | Structure | MH+ | Hsp90 IC50* |
|---|---|---|---|
| 51 | (5-(5-chloro-2,4-dihydroxyphenyl)-4-(4-((4-(2-hydroxyethyl)piperidin-1-yl)methyl)phenyl)-N-ethylisoxazole-3-carboxamide) | 500, 502 | A |
| 52 | (5-(5-chloro-2,4-dihydroxyphenyl)-N-ethyl-4-(4-(piperidin-1-ylmethyl)phenyl)isoxazole-3-carboxamide) | 456, 458 | A |
| 53 | (5-(5-chloro-2,4-dihydroxyphenyl)-N-ethyl-4-(4-((4-hydroxypiperidin-1-yl)methyl)phenyl)isoxazole-3-carboxamide) | 472, 474 | A |
| 54 | (5-(5-chloro-2,4-dihydroxyphenyl)-N-ethyl-4-(4-(pyrrolidin-1-ylmethyl)phenyl)isoxazole-3-carboxamide) | 442 | A |

-continued

| Example | Structure | MH+ | Hsp90 IC50* |
|---|---|---|---|
| 55 | 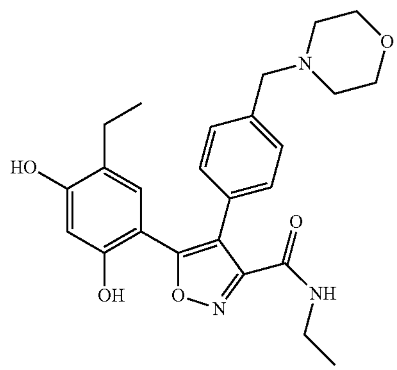 [SMILES: CCNC(=O)c1noc(-c2cc(CC)c(O)cc2O)c1-c1ccc(CN2CCOCC2)cc1] | 452 | A** |
| 56 | 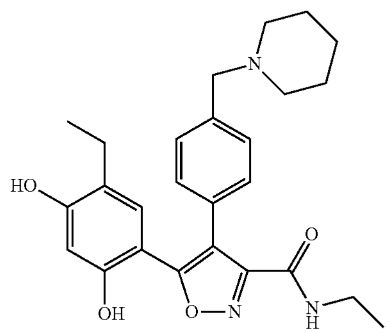 [SMILES: CCNC(=O)c1noc(-c2cc(CC)c(O)cc2O)c1-c1ccc(CN2CCCCC2)cc1] | 450 | A** |
| 57 | 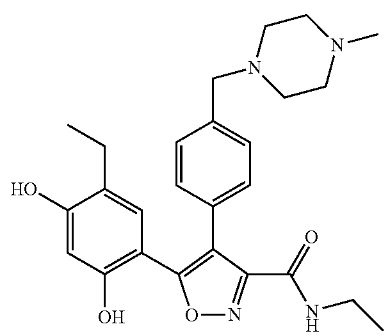 [SMILES: CCNC(=O)c1noc(-c2cc(CC)c(O)cc2O)c1-c1ccc(CN2CCN(C)CC2)cc1] | 465 | A** |
| 58 | 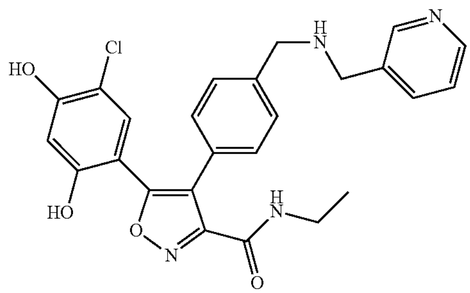 [SMILES: CCNC(=O)c1noc(-c2cc(Cl)c(O)cc2O)c1-c1ccc(CNCc2cccnc2)cc1] | 479, 481 | A |

-continued

| Example | Structure | MH+ | Hsp90 IC50* |
|---|---|---|---|
| 59 | 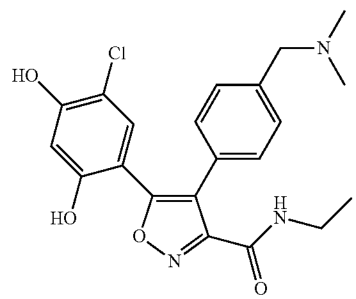 [SMILES: CCNC(=O)c1noc(-c2cc(Cl)c(O)cc2O)c1-c1ccc(CN(C)C)cc1] | 416, 418 | A |
| 60 | 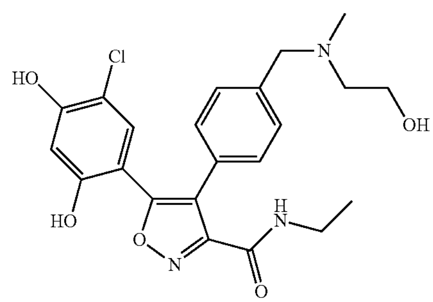 [SMILES: CCNC(=O)c1noc(-c2cc(Cl)c(O)cc2O)c1-c1ccc(CN(C)CCO)cc1] | 446, 448 | A |
| 61 | 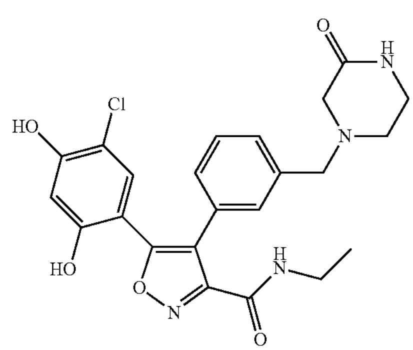 [SMILES: CCNC(=O)c1noc(-c2cc(Cl)c(O)cc2O)c1-c1cccc(CN2CCNC(=O)C2)c1] | 471, 473 | A |
| 62 | 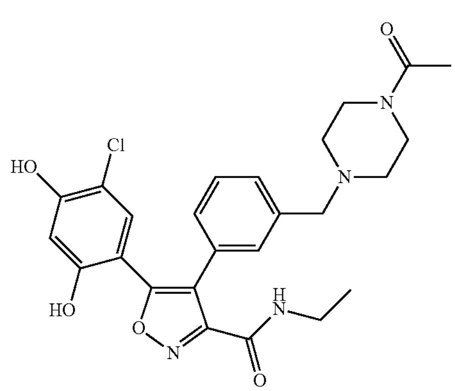 [SMILES: CCNC(=O)c1noc(-c2cc(Cl)c(O)cc2O)c1-c1cccc(CN2CCN(C(C)=O)CC2)c1] | 499, 501 | A |

-continued

| Example | Structure | MH+ | Hsp90 IC50* |
|---------|-----------|-----|-------------|
| 63 | 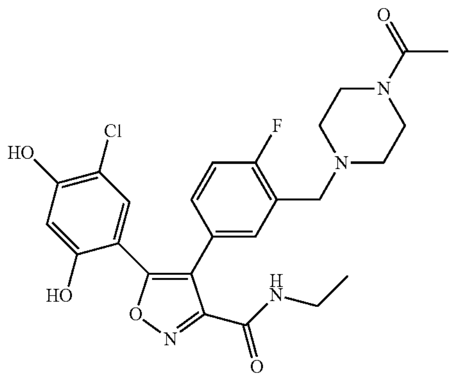 [SMILES: CCNC(=O)c1noc(-c2cc(Cl)c(O)cc2O)c1-c1ccc(F)c(CN2CCN(C(C)=O)CC2)c1] | 517 519 | A |
| 64 | 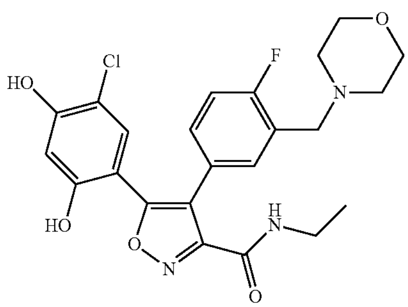 [SMILES: CCNC(=O)c1noc(-c2cc(Cl)c(O)cc2O)c1-c1ccc(F)c(CN2CCOCC2)c1] | 476 478 | A |

*Fluorescence Polarisation Assay
**prepared from ethyl resorcinol starting material Additional compounds 41a-s were prepared by methods analogous to Example 41:

| Example | Structure | MH+ | Hsp90 IC50* |
|---------|-----------|-----|-------------|
| 41a | 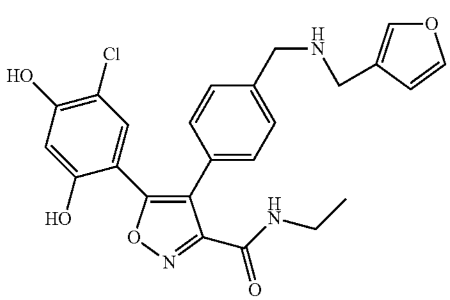 [SMILES: CCNC(=O)c1noc(-c2cc(Cl)c(O)cc2O)c1-c1ccc(CNCc2ccoc2)cc1] | 468 | A |

-continued

| Example | Structure | MH+ | Hsp90 IC50* |
|---------|-----------|-----|-------------|
| 41b | 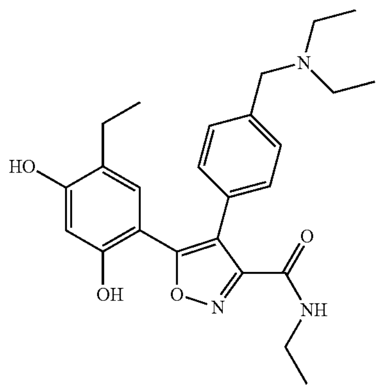 [SMILES: CCNC(=O)c1noc(-c2cc(CC)c(O)cc2O)c1-c1ccc(CN(CC)CC)cc1] | 438 | A** |
| 41c | 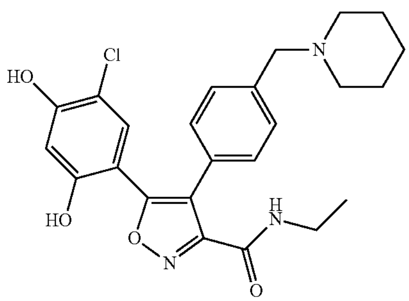 [SMILES: CCNC(=O)c1noc(-c2cc(Cl)c(O)cc2O)c1-c1ccc(CN2CCCCC2)cc1] | 442 | A |
| 41e | 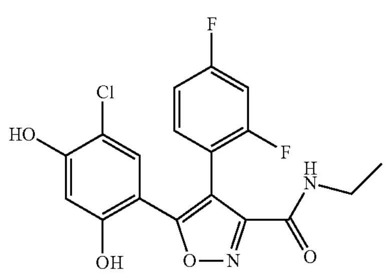 [SMILES: CCNC(=O)c1noc(-c2cc(Cl)c(O)cc2O)c1-c1ccc(F)cc1F] | 395 | A |
| 41f | 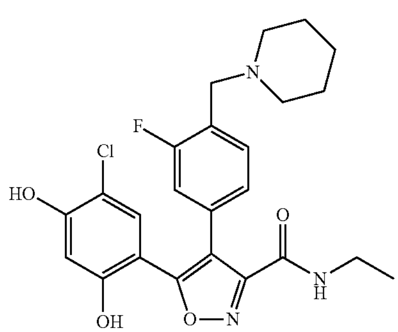 [SMILES: CCNC(=O)c1noc(-c2cc(Cl)c(O)cc2O)c1-c1ccc(CN2CCCCC2)c(F)c1] | 474 | A |

-continued

| Example | Structure | MH+ | Hsp90 IC50* |
|---|---|---|---|
| 41g | 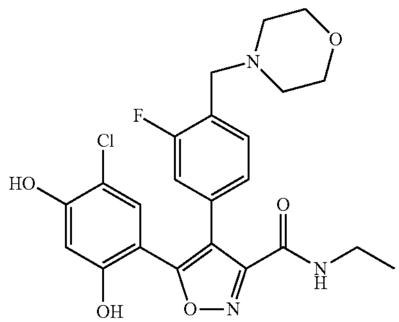 [SMILES: CCNC(=O)c1noc(-c2cc(Cl)c(O)cc2O)c1-c1ccc(CN2CCOCC2)c(F)c1] | 476 | A |
| 41h | 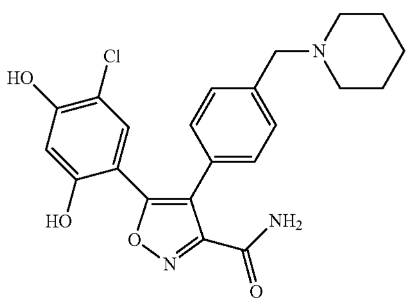 [SMILES: NC(=O)c1noc(-c2cc(Cl)c(O)cc2O)c1-c1ccc(CN2CCCCC2)cc1] | 428 | A |
| 41i | 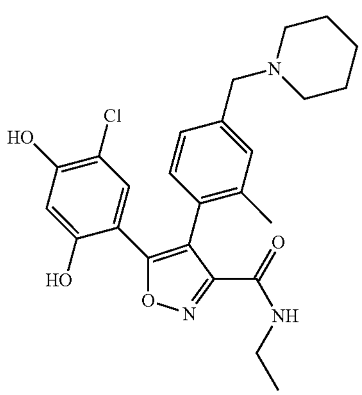 [SMILES: CCNC(=O)c1noc(-c2cc(Cl)c(O)cc2O)c1-c1ccc(CN2CCCCC2)cc1C] | 470 | A |
| 41j | 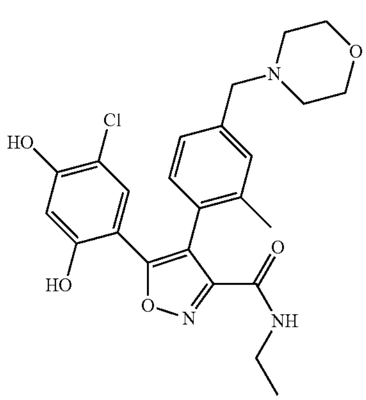 [SMILES: CCNC(=O)c1noc(-c2cc(Cl)c(O)cc2O)c1-c1ccc(CN2CCOCC2)cc1C] | 472 | A |

-continued
| Example | Structure | MH+ | Hsp90 IC50* |
|---|---|---|---|
| 41k | 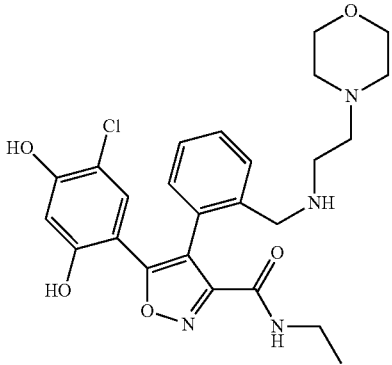 [SMILES: CCNC(=O)c1noc(-c2cc(Cl)c(O)cc2O)c1-c1ccccc1CNCCN1CCOCC1] | 502 | A |
| 41m | 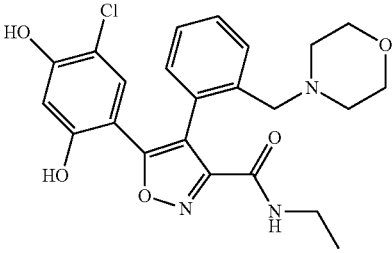 [SMILES: CCNC(=O)c1noc(-c2cc(Cl)c(O)cc2O)c1-c1ccccc1CN1CCOCC1] | 458 | A |
| 41n | 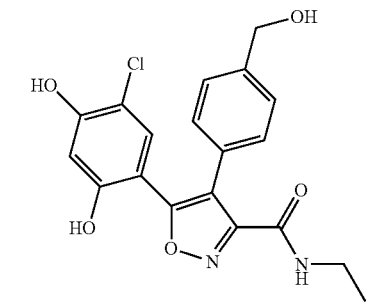 [SMILES: CCNC(=O)c1noc(-c2cc(Cl)c(O)cc2O)c1-c1ccc(CO)cc1] | 389 | A*** |
| 41p | 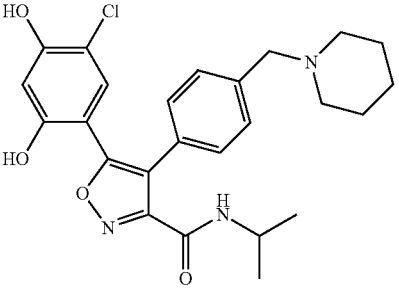 [SMILES: CC(C)NC(=O)c1noc(-c2cc(Cl)c(O)cc2O)c1-c1ccc(CN2CCCCC2)cc1] | 471 | A |

-continued
| Example | Structure | MH+ | Hsp90 IC50* |
|---|---|---|---|
| 41q | 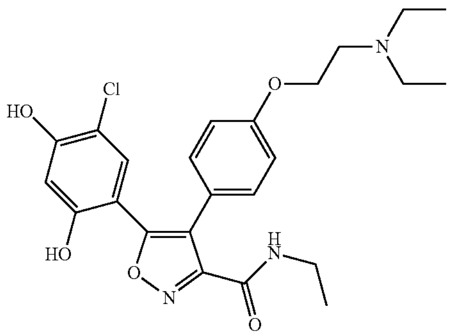 [SMILES: CCNC(=O)c1noc(-c2cc(Cl)c(O)cc2O)c1-c1ccc(OCCN(CC)CC)cc1] | 475 | A**** |
| 41r | 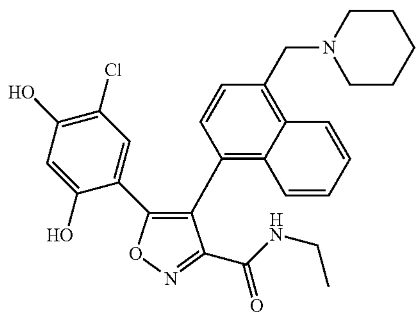 [SMILES: CCNC(=O)c1noc(-c2cc(Cl)c(O)cc2O)c1-c1ccc(CN2CCCCC2)c2ccccc12] | 507 | A***** |
| 41s | 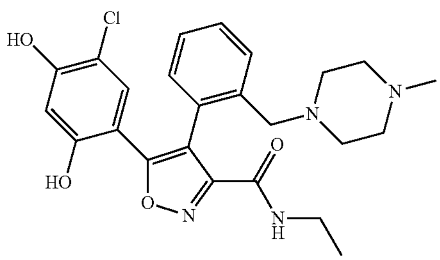 [SMILES: CCNC(=O)c1noc(-c2cc(Cl)c(O)cc2O)c1-c1ccccc1CN1CCN(C)CC1] | 472 | A |
*Fluorescence Polarisation Assay
**prepared from ethyl resorcinol starting material
***prepared by reduction of the aldehyde intermediate
****prepared by alkyation of the intermediate phenol
*****prepared from the naphthyl aldehyde
Example 65
Reaction scheme:
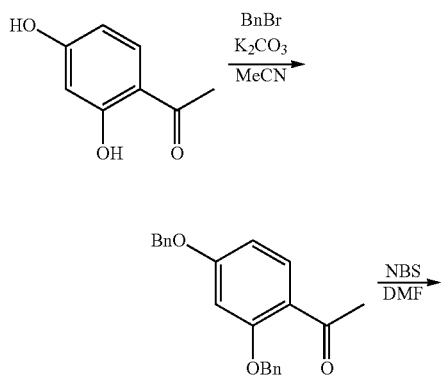
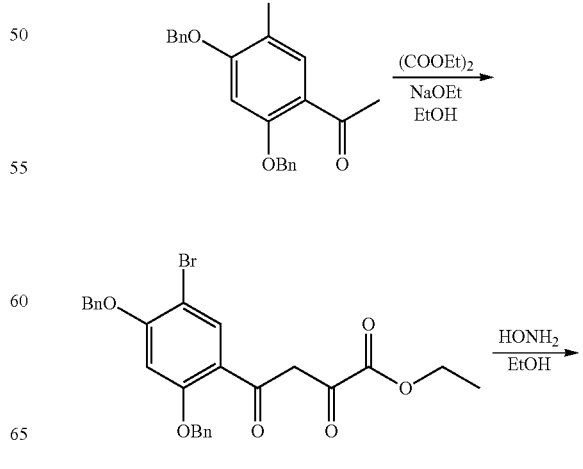

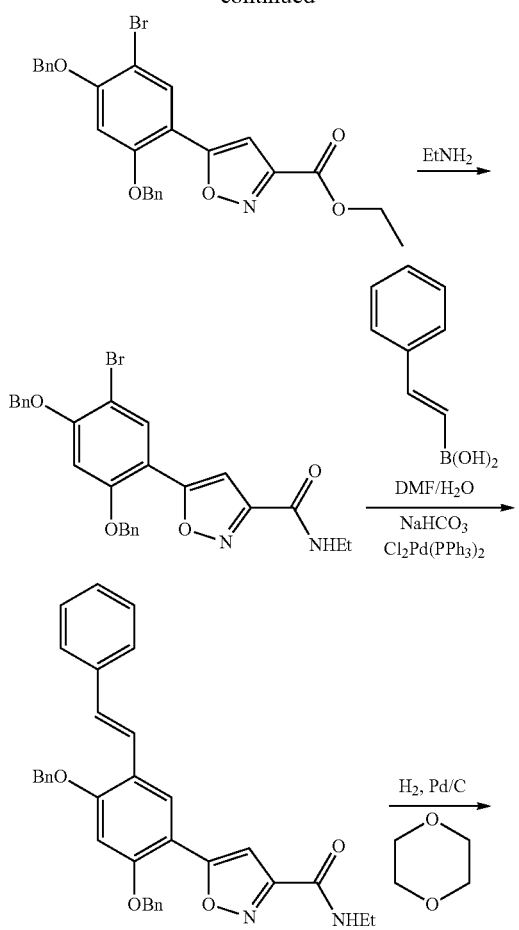

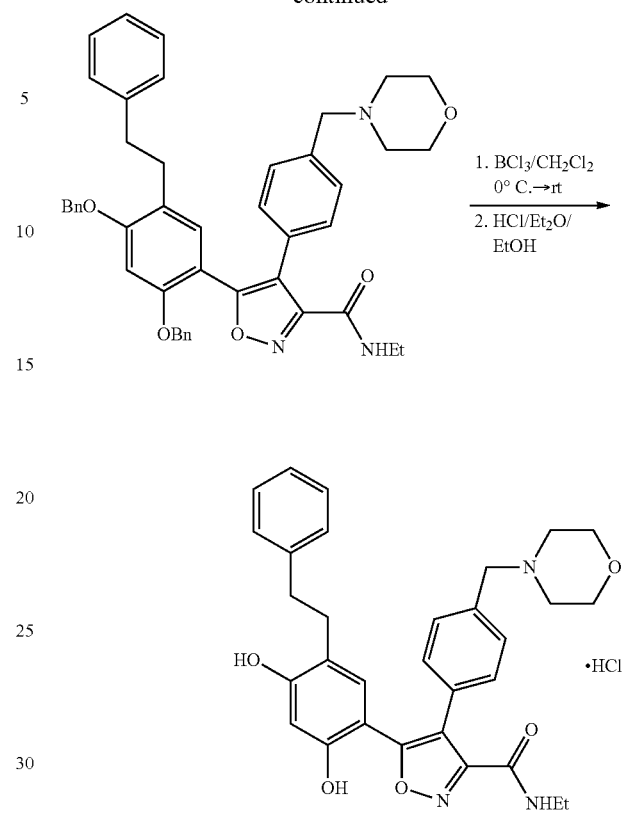

Step 1

1-(2,4-Bis-benzyloxy-phenyl)-ethanone

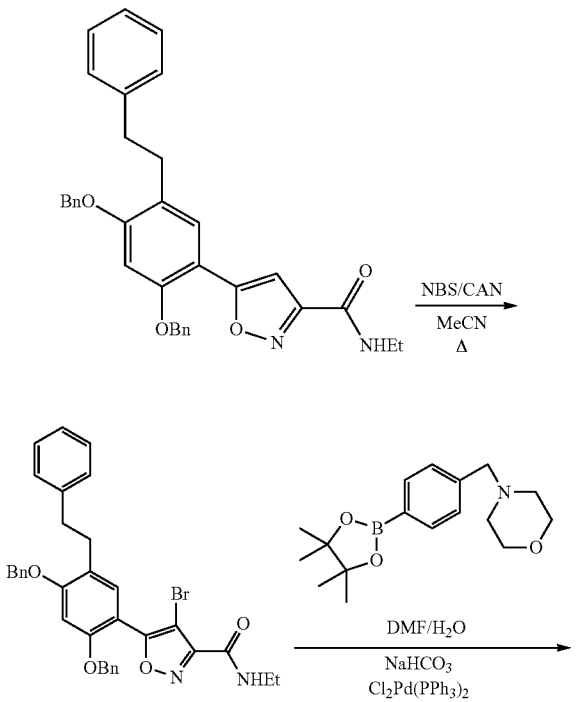

35 g of 2,4-dihydroxyacetophenone (0.230 mol, 1 eq) were dissolved in 500 ml acetonitrile. 79.5 g of potassium carbonate (0.575 mol, 2.5 eq) and 86.6 g benzyl bromide (0.506 mol, 2.2 eq) were added. The mixture was refluxed for 64 hours, cooled down and acetonitrile removed under reduced pressure. The residue was separated between water and ethyl acetate. The residue was mainly mono-benzylated resorcinol.

The crude product (43 g) was then dissolved in 250 ml DMF. Potassium carbonate (29 g, 0.210 mol, 1.2 eq) and 25 ml benzyl bromide (0.210 mol, 1.2 eq) were added and the mixture was stirred over night. The solvent was removed under reduced pressure and the residue was separated between ethyl acetate and water. After removal of the solvent, the residue was triturated with hexane to remove excess benzyl bromide.

LC-MS [M+H]+=333

Yield: 51.2 g (67%)

Step 2

1-(2,4-Bis-benzyloxy-5-bromo-phenyl)-ethanone

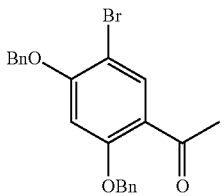

51.2 g of 1-(2,4-Bis-benzyloxy-phenyl)-ethanone (0.154 mol, 1 eq) were dissolved in 250 ml DMF. 27.42 g N-bromosuccinimide (0.154 mol, 1 eq) in 100 ml DMF were added dropwise. The mixture was stirred at room temperature over night. The reaction mixture was poured onto 700 ml of water and the precipitate filtered off. The filter cake was rinsed with water and the colourless solid was recrystallised from 370 ml acetonitrile.

LC-MS [M+H]+=411 & 413
Yield: 58.15 g (92%)

Step 3

4-(2,4-Bis-benzyloxy-5-bromo-phenyl)-2,4-dioxo-butyric acid ethyl ester

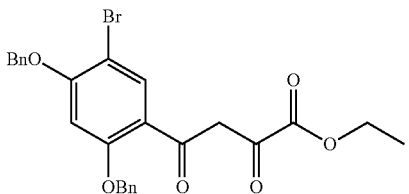 [SMILES: CCOC(=O)C(=O)CC(=O)c1cc(Br)c(OCc2ccccc2)cc1OCc1ccccc1]

9.75 g sodium (0.424 mol, 3 eq) were dissolved in 500 ml absolute ethanol (1.5 hours). 58 g of 1-(2,4-Bis-benzyloxy-5-bromo-phenyl)-ethanone (0.141 mol, 1 eq) and 30.98 g diethyl oxalate (0.212 mol, 1.5 eq) were added and the mixture was refluxed for 2 hours. After cooling down, the mixture was poured onto 220 ml of 2N aqueous HCl and the product was extracted into 700 ml dichloromethane. The solvent was removed under reduced pressure and the yellow residue was triturated with 150 ml diethyl ether.

Yield: 69.24 g (96%)

1H NMR (400 MHz, CDCl$_3$) δ 1.27 (t, 3H), 4.27 (q, 2H), 5.13 (d, 2H), 6.54 (s, 1H), 7.37 (m, 10H), 8.17 (s, 1H).

Step 4

5-(2,4-Bis-benzyloxy-5-bromo-phenyl)-isoxazole-3-carboxylic acid ethyl ester

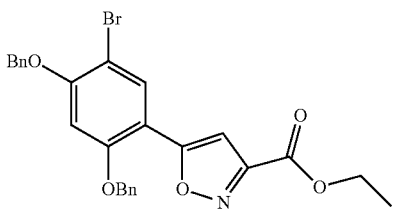 [SMILES: CCOC(=O)c1cc(-c2cc(Br)c(OCc3ccccc3)cc2OCc2ccccc2)on1]

69.3 g of 4-(2,4-Bis-benzyloxy-5-bromo-phenyl)-2,4-dioxo-butyric acid ethyl ester (0.135 mol, 1 eq) were dissolved in 750 ml ethanol. 14.11 g hydroxylamine hydrochloride (0.203 mol, 1.5 eq) were added. The mixture was refluxed for 2.5 hours and cooled down. It was then poured onto 1000 ml water, the precipitate was filtered off. The filter cake was washed with 500 ml of water followed by 75 ml diethyl ether and dried.

Yield: 67.62 g (99%)

1H NMR (400 MHz, CDCl$_3$) δ 1.39 (t, 3H), 4.41 (q, 2H), 5.11 (d, 2H), 5.15 (d, 2H), 6.58 (s, 1H), 6.99 (s, 1H), 7.35 (m, 10H), 8.16 (s, 1H).

Step 5

5-(2,4-Bis-benzyloxy-5-bromo-phenyl)-isoxazole-3-carboxylic acid ethylamide

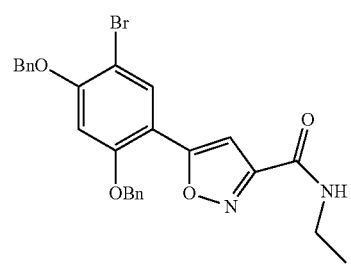 [SMILES: CCNC(=O)c1cc(-c2cc(Br)c(OCc3ccccc3)cc2OCc2ccccc2)on1]

5-(2,4-bis-benzyloxy-5-bromo-phenyl)-isoxazole-3-carboxylic acid ethyl ester was suspended in ethanol and ethylamine (2M in methanol, 3 eq), the resulting yellow suspension was heated to reflux (80° C.) under nitrogen, at which point the reagents went into solution. This was heated for 14 hours, then left to cool to ambient temperature. A white precipitate formed, which was filtered off and washed with further ethanol before being dried in vacuo.

LC-MS retention time 2.868 minutes [M+H]+=507 & 509 (run time 3.75 minutes)

Step 6

5-(2,4-Bis-benzyloxy-5-styrylphenyl)-isoxazole-3-carboxylic acid ethylamide

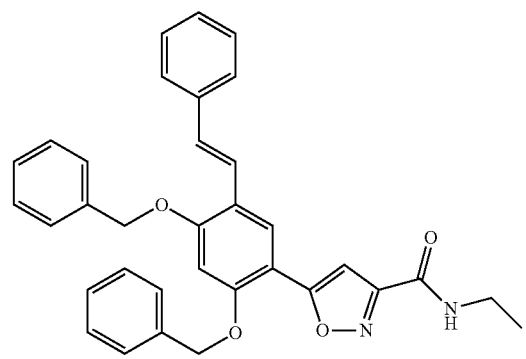 [SMILES: CCNC(=O)c1cc(-c2cc(/C=C/c3ccccc3)c(OCc3ccccc3)cc2OCc2ccccc2)on1]

To a mixture of trans-2-phenylvinylboronic acid (0.472 g, 3.2 mmol) and 5-(2,4-Bis-benzyloxy-5-bromophenyl)-isoxazole-3-carboxylic acid ethylamide (1.079 g, 2.13 mmol) was added sodium hydrogen carbonate (536 mg, 6.39 mmol) followed by DMF (25 mL) and water (5 mL). The mixture was degassed by evacuation and flushing with nitrogen (three times), followed by bubbling nitrogen gas through mixture for five minutes.

Dichlorobis(triphenylphosphine)palladium (II) (149 mg, 0.21 mmol) was added and reaction mixture was heated under a nitrogen atmosphere at 80° C. for seven hours (reaction mixture becomes dark brown in colour after 10 minutes). The reaction mixture was allowed to cool to ambient temperature and the majority of solvents were removed in vacuo. The resulting residue was partitioned between ethyl acetate (100 mL) and water (100 mL) and this mixture was filtered through a pad of celite to remove Palladium residues. The phases were separated and the organic phase was washed with water (2×50 mL), saturated aqueous sodium chloride solution (100 mL) then dried over sodium sulphate. The mixture was filtered and the filtrate solvents were removed in vacuo to afford a brown solid (800 mg). The celite filter cake was washed with dichloromethane then dried over sodium sulphate. The mixture was filtered and the filtrate solvents were removed in vacuo to afford a brown solid (541 mg). The combined product batches were purified by trituration with ethyl acetate-hexane mixture. This affords 5-(2,4-Bis-benzyloxy-5-styrylphenyl)-isoxazole-3-carboxylic acid ethylamide as a light brown solid (808 mg, 71%). LCMS: [M+H]+ 531. 1H NMR (400 MHz, CDCl$_3$) δ 1.12 (t, 3H), 3.37 (m, 2H), 4.95 (s, 2H), 5.07 (s, 2H), 6.46 (s, 1H), 6.70 (brt, 1H). 7.11 (s, 1H), 7.17 (d, 1H), 7.23 (d, 1H), 7.32-7.44 (m, 15H), 8.09 (s, 1H).

Step 7

5-(2,4-Bis-benzyloxy-5-phenethylphenyl)-isoxazole-3-carboxylic acid ethylamide

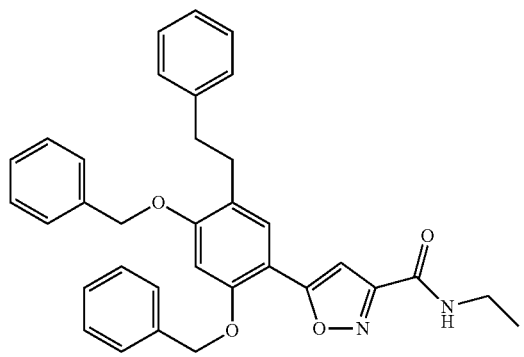 [SMILES: CCNC(=O)c1cc(-c2cc(CCc3ccccc3)c(OCc3ccccc3)cc2OCc2ccccc2)on1]

Palladium on charcoal catalyst (10%; 50 mg) was added to a degassed solution of 5-(2,4-Bis-benzyloxy-5-styrylphenyl)-isoxazole-3-carboxylic acid ethylamide (690 mg, 1.30 mmol) in 1,4-dioxane (50 mL) under a nitrogen atmosphere. The reaction mixture was hydrogenated for a total of 4.75 hrs with further Pd on charcoal catalyst (50 mg) added at 0.75 and 2.5 hrs. The reaction mixture was filtered through a pad of celite, which was washed with 1,4-dioxane (20 mL) and dichloromethane (20 mL). The combined filtrate solvents were removed in vacuo to afford a cream-coloured solid, which was purified by flash chromatography on silica gel (20 g, IST) eluting with 10 to 50% ethyl acetate in hexane. This affords 5-(2,4-Bis-benzyloxy-5-phenethylphenyl)-isoxazole-3-carboxylic acid ethylamide as a pale yellow solid (609 mg, 88%). LCMS: [M+H]+ 533. 1H NMR (400 MHz, CDCl$_3$) δ 1.26 (t, 3H), 2.86-2.96 (m, 4H), 3.49 (m, 2H), 5.03 (s, 2H) 5.18 (s, 2H), 6.56 (s, 1H), 6.81 (t, 1H), 7.07 (s, 1H), 7.15-7.20 (m, 3H), 7.23-7.28 (m, 2H), 7.31-7.42 (m, 10H), 7.73 (s, 1H).

Step 8

5-(2,4-bis-benzyloxy-5-phenethylphenyl)-4-bromo-isoxazole-3-carboxylic acid ethylamide

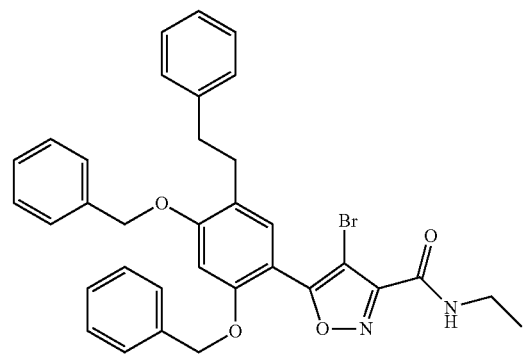 [SMILES: CCNC(=O)c1noc(-c2cc(CCc3ccccc3)c(OCc3ccccc3)cc2OCc2ccccc2)c1Br]

N-Bromosuccinimide (207 mg, 1.16 mmol) was added to a suspension of 5-(2,4-Bis-benzyloxy-5-phenethylphenyl)-isoxazole-3-carboxylic acid ethylamide (564 mg, 1.06 mmol) in acetonitrile (20 mL). Ceric ammonium nitrate (290 mg, 0.53 mmol) was added and the reaction mixture was heated to reflux (affording homogeneous orange solution) and stirred for 30 minutes. The reaction mixture was allowed to cool to ambient temperature and acetonitrile was removed in vacuo. The residue was partitioned between ethyl acetate (50 mL) and water (50 mL) and the phases were separated. The organic phase was washed with saturated aqueous sodium chloride solution (50 mL) and dried over sodium sulphate. The mixture was filtered and the filtrate solvents were removed in vacuo to afford a yellow oil which was purified by flash chromatography on silica gel (20 g, IST) eluting with 10-30% ethyl acetate in hexane. This affords 5-(2,4-Bis-benzyloxy-5-phenethylphenyl)-4-bromo-isoxazole-3-carboxylic acid ethylamide as yellow oil (326 mg, 53%). LCMS: [M+H]+ 613, 611.

Step 9

5-(2,4-bis-benzyloxy-5-phenethyl-phenyl)-4-(4-morpholin-4-ylmethyl-phenyl)-isoxazole-3-carboxylic acid ethylamide

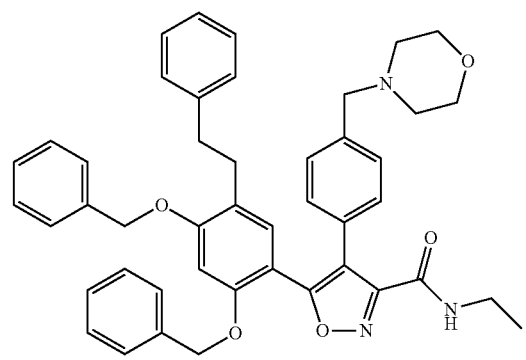 [SMILES: CCNC(=O)c1noc(-c2cc(CCc3ccccc3)c(OCc3ccccc3)cc2OCc2ccccc2)c1-c1ccc(CN2CCOCC2)cc1]

To a mixture of 4-morpholin-4-ylmethyl-phenyl pinnacol borane (0.215 g, 0.71 mmol) and 5-(2,4-Bis-benzyloxy-5-phenethylphenyl)-4-bromo-isoxazole-3-carboxylic acid ethylamide (0.347 g, 0.57 mmol) was added sodium hydrogen carbonate (142 mg, 1.69 mmol) followed by DMF (10 mL) and water (2.0 mL). The mixture was degassed by evacuation and flushing with nitrogen (three times), followed by bubbling nitrogen gas through mixture for five minutes. Dichlorobis(triphenylphosphine)palladium (II) (40 mg, 0.057 mmol) was added and reaction mixture was heated under a nitrogen atmosphere at 80° C. for 5 hours (reaction mixture becomes dark brown in colour). Another 20 mg (0.029 mmol) of dichlorobis(triphenylphosphine)palladium (II) was added and reaction mixture was heated at 80° C. for 15 hours then allowed to cool to ambient temperature. The majority of solvents were removed in vacuo and the residue was partitioned between ethyl acetate (50 mL) and water (50 mL).

This mixture was filtered through a pad of celite to remove Palladium residues and then the phases were separated and the organic phase was washed with water (2×50 mL), saturated aqueous sodium chloride solution (50 mL) then dried over sodium sulphate. The mixture was filtered and the filtrate solvents were removed in vacuo to afford a brown oil. The crude reaction product was purified by flash chromatography on silica gel (20 g, IST) eluting with a solvent gradient of 30 to 70% ethyl acetate in hexane. This affords 5-(2,4-bis-benzyloxy-5-phenethyl-phenyl)-4-(4-morpholin-4-ylmethyl-phenyl)-isoxazole-3-carboxylic acid ethylamide as yellow oil (0.110 g, 27%). LCMS: [M+H]+ 708.

Step 10

5-(2,4-dihydroxy-5-phenethyl-phenyl)-4-(4-morpholin-4-ylmethyl-phenyl)-isoxazole-3-carboxylic acid ethylamide hydrochloride

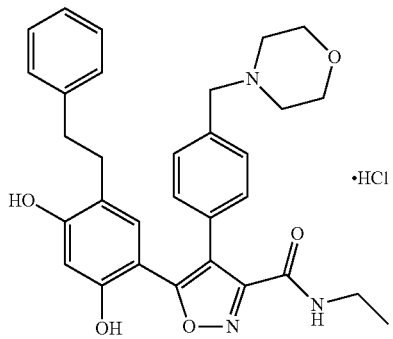 [SMILES: CCNC(=O)c1noc(-c2cc(CCc3ccccc3)c(O)cc2O)c1-c1ccc(CN2CCOCC2)cc1 ; Cl]

To an ice-bath cooled solution of 5-(2,4-bis-benzyloxy-5-phenethyl-phenyl)-4-(4-morpholin-4-ylmethyl-phenyl)-isoxazole-3-carboxylic acid ethylamide (0.109 g, 0.15 mmol) in dichloromethane (4 mL) under a nitrogen atmosphere was added a 1.0M solution of Boron trichloride in dichloromethane (0.45 mL; 0.45 mmol). The reaction mixture was stirred at 0° C. for 20 minutes then at ambient temperature for 3.5 hours. The reaction mixture was re-cooled to 0° C. and quenched by the addition of saturated aqueous sodium hydrogen carbonate solution (5 mL). After stirring for 5 minutes the dichloromethane was removed in vacuo and the residue was partitioned between ethyl acetate (20 mL) and water (20 mL). The phases were separated and the organic phase was washed with water (20 mL), saturated aqueous sodium chloride solution (20 mL) then dried over sodium sulphate. The mixture was filtered and the filtrate solvents were removed in vacuo to afford a light-brown oil which was purified by adsorption onto silica gel then flash chromatography on silica gel (10 g IST) eluting with 0 to 5% methanol in ethyl acetate. This affords a colourless oil which was triturated with 1.0M HCl in diethyl ether solution (5 mL) to afford 5-(2,4-dihydroxy-5-phenethyl-phenyl)-4-(4-morpholin-4-ylmethyl-phenyl)-isoxazole-3-carboxylic acid ethylamide hydrochloride (0.019 g; 24%). LCMS: [M+H]+ 528. 1H NMR (400 MHz, d6-DMSO) ☐ 1.08 (t, 3H), 2.60 (m, 4H), 2.90-3.30 (m, 6H), 3.67 (m, 2H), 3.87 (m, 2H), 4.30 (s, 2H), 6.46 (s, 1H), 6.84 (s, 1H), 7.05-7.49 (m, 5H), 7.40-7.68 (m, 4H), 8.90 (brs, 1H), 9.67 (s, 1H), 9.89 (s, 1H), 10.75 (brs, 1H).

Example 65 had activity 'A' in the Fluorescence Polarisation Assay, as described below.

The examples in the following Table were prepared by methods analogous to Example 64, and had the activities shown in the Fluorescence Polarisation Assay, as described below.

| Example | Structure | MH+ | Hsp90 IC50* |
|---|---|---|---|
| 66 | 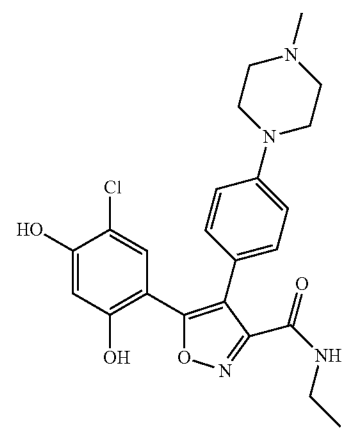 [SMILES: CCNC(=O)c1noc(-c2cc(Cl)c(O)cc2O)c1-c1ccc(N2CCN(C)CC2)cc1] | 457 459 | A |
| 67 | 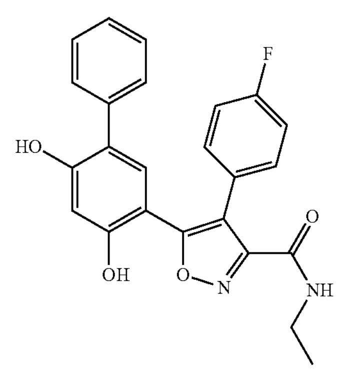 [SMILES: CCNC(=O)c1noc(-c2cc(-c3ccccc3)c(O)cc2O)c1-c1ccc(F)cc1] | 419 | A |

| Example | Structure | MH+ | Hsp90 IC50* |
|---|---|---|---|
| 68 | 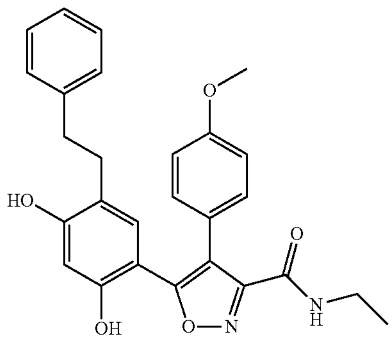 [SMILES: CCNC(=O)c1noc(-c2cc(CCc3ccccc3)c(O)cc2O)c1-c1ccc(OC)cc1] | 459 | A |
| 69 | 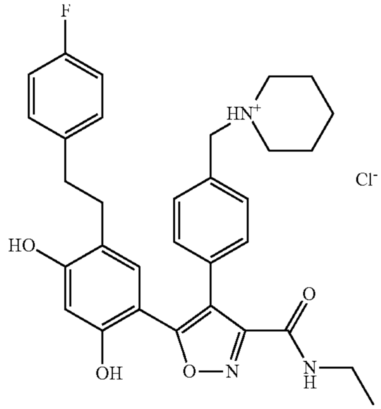 [SMILES: CCNC(=O)c1noc(-c2cc(CCc3ccc(F)cc3)c(O)cc2O)c1-c1ccc(C[NH+]2CCCCC2)cc1 ; [Cl-]] | 544 | A |
| 70 | 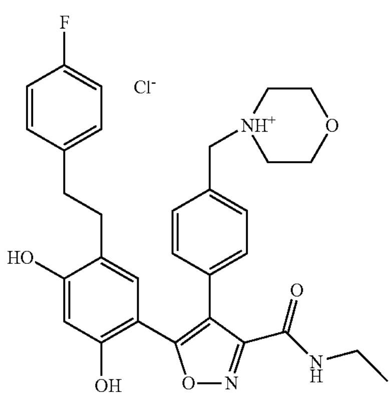 [SMILES: CCNC(=O)c1noc(-c2cc(CCc3ccc(F)cc3)c(O)cc2O)c1-c1ccc(C[NH+]2CCOCC2)cc1 ; [Cl-]] | 546 | A |
| 71 | 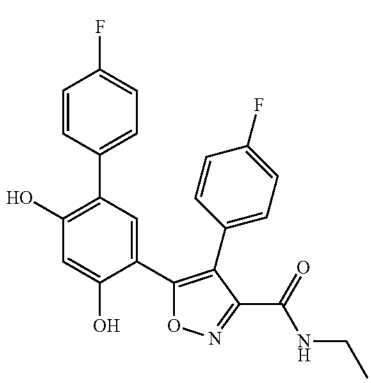 [SMILES: CCNC(=O)c1noc(-c2cc(-c3ccc(F)cc3)c(O)cc2O)c1-c1ccc(F)cc1] | 437 | A |
| 72 | | 516 | A |
| 73 | | 518 | A |
| 74 | | 500 | A |
| 75 | | 546 | A |

The additional examples 75a-v in the following table were also prepared by methods analogues to example 65.

| Example | Structure | MH+ | Hsp90 IC50 |
|---|---|---|---|
| 75a | 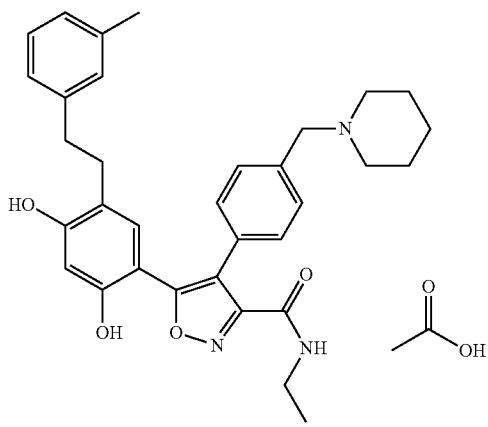 | 540 | A |
| 75b | 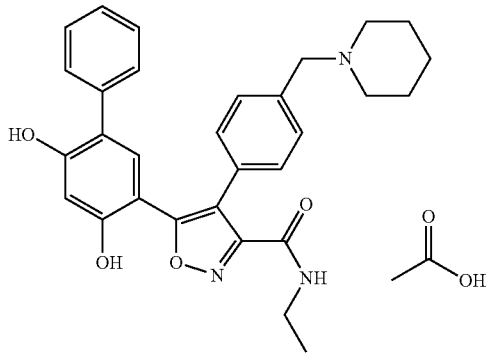 | 498 | A |
| 75c | 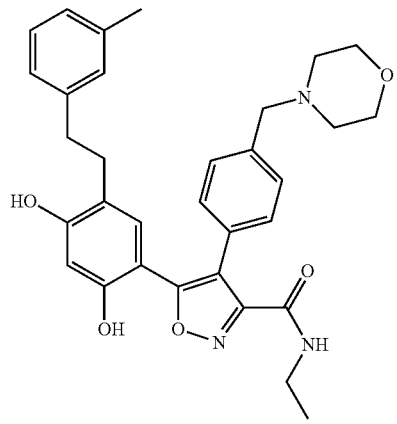 [SMILES: CCNC(=O)c1noc(-c2cc(CCc3cccc(C)c3)c(O)cc2O)c1-c1ccc(CN2CCOCC2)cc1] | 542 | A |
| 75d | 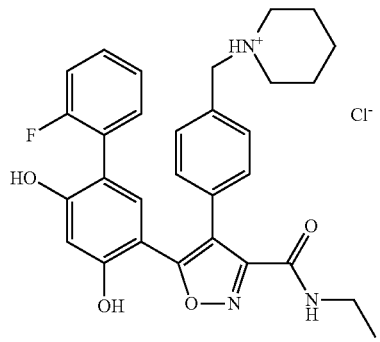 [SMILES: CCNC(=O)c1noc(-c2cc(-c3ccccc3F)c(O)cc2O)c1-c1ccc(C[NH+]2CCCCC2)cc1 ; [Cl-]] | 516 | A |

-continued

| Example | Structure | MH+ | Hsp90 IC50 |
|---|---|---|---|
| 75e | 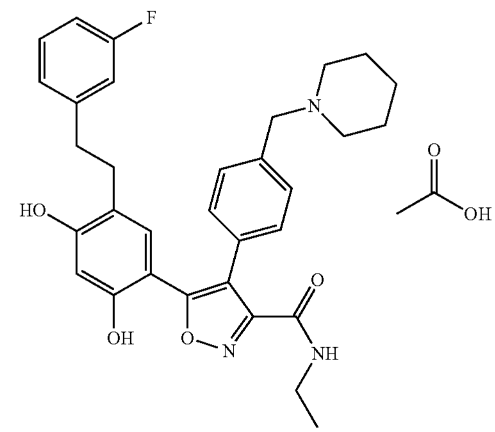 | 544 | A |
| 75f | 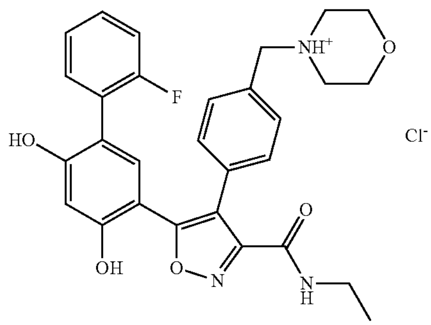 [SMILES: CCNC(=O)c1noc(-c2cc(-c3ccccc3F)c(O)cc2O)c1-c1ccc(C[NH+]2CCOCC2)cc1 ; [Cl-]] | 518 | A |
| 75g | 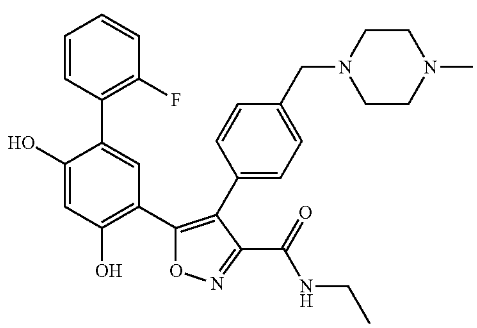 [SMILES: CCNC(=O)c1noc(-c2cc(-c3ccccc3F)c(O)cc2O)c1-c1ccc(CN2CCN(C)CC2)cc1] | 531 | A |
| 75h | 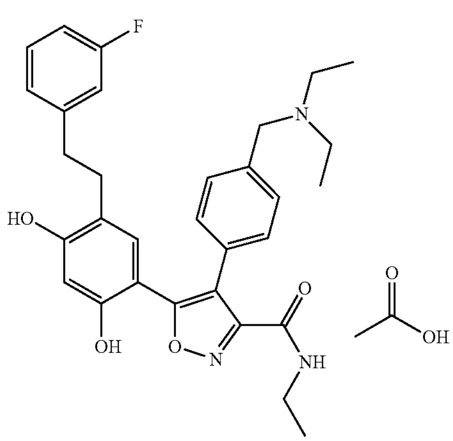 | 532 | A |

-continued

| Example | Structure | MH+ | Hsp90 IC50 |
|---|---|---|---|
| 75i | 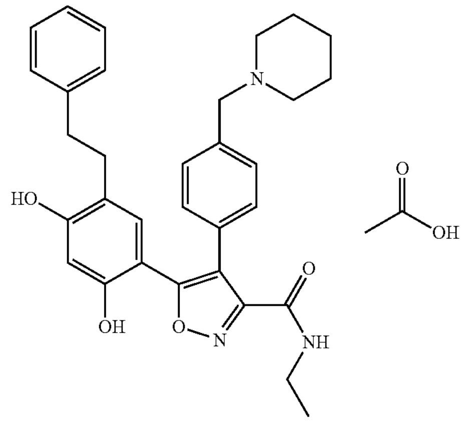 | 526 | A |
| 75k | 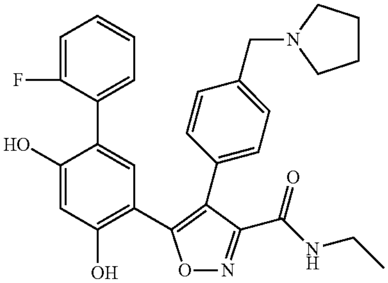 [SMILES: CCNC(=O)c1noc(-c2cc(-c3ccccc3F)c(O)cc2O)c1-c1ccc(CN2CCCC2)cc1] | 502 | A |
| 75m | 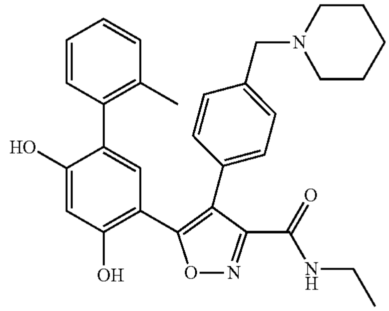 [SMILES: CCNC(=O)c1noc(-c2cc(-c3ccccc3C)c(O)cc2O)c1-c1ccc(CN2CCCCC2)cc1] | 512 | A |
| 75n | 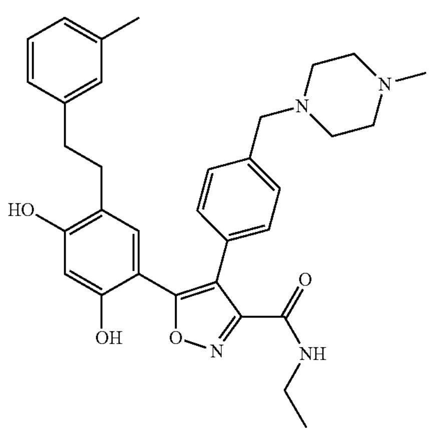 [SMILES: CCNC(=O)c1noc(-c2cc(CCc3cccc(C)c3)c(O)cc2O)c1-c1ccc(CN2CCN(C)CC2)cc1] | 545 | A |

-continued
| Example | Structure | MH+ | Hsp90 IC50 |
|---|---|---|---|
| 75p | 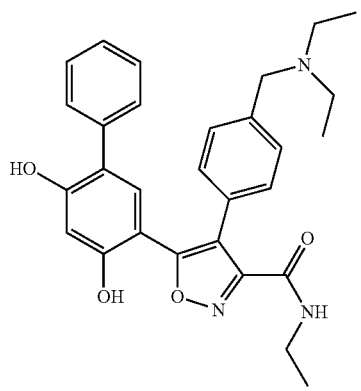 [SMILES: CCNC(=O)c1noc(-c2cc(-c3ccccc3)c(O)cc2O)c1-c1ccc(CN(CC)CC)cc1] | 486 | A |
| 75q | 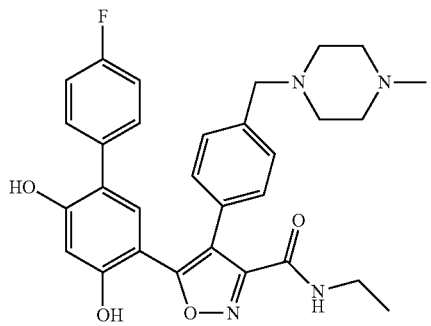 [SMILES: CCNC(=O)c1noc(-c2cc(-c3ccc(F)cc3)c(O)cc2O)c1-c1ccc(CN2CCN(C)CC2)cc1] | 531 | A |
| 75r | 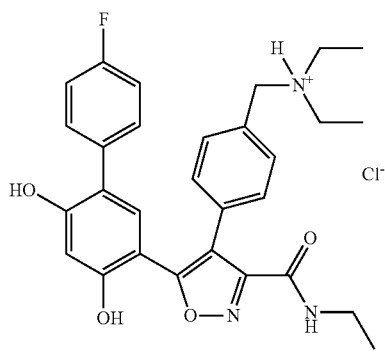 [SMILES: CCNC(=O)c1noc(-c2cc(-c3ccc(F)cc3)c(O)cc2O)c1-c1ccc(C[NH+](CC)CC)cc1 ; [Cl-]] | 504 | A |
| 75s | 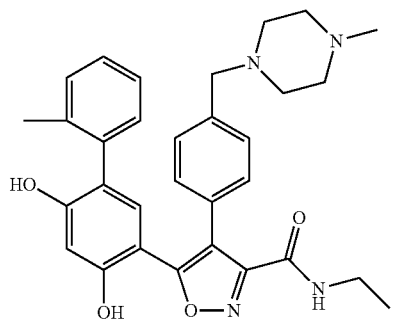 [SMILES: CCNC(=O)c1noc(-c2cc(-c3ccccc3C)c(O)cc2O)c1-c1ccc(CN2CCN(C)CC2)cc1] | 527 | A |

-continued

| Example | Structure | MH+ | Hsp90 IC50 |
|---------|-----------|-----|------------|
| 75t | 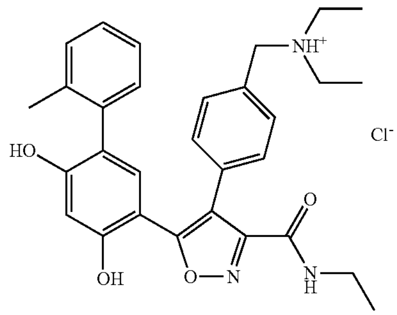 | 500 | A |
| 75u | 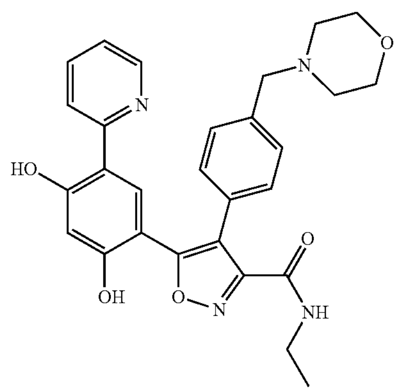 [SMILES: CCNC(=O)c1noc(-c2cc(-c3ccccn3)c(O)cc2O)c1-c1ccc(CN2CCOCC2)cc1] | 501 | B |
| 75v | 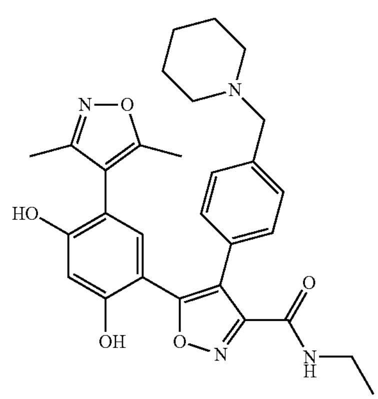 [SMILES: CCNC(=O)c1noc(-c2cc(-c3c(C)noc3C)c(O)cc2O)c1-c1ccc(CN2CCCCC2)cc1] | 517 | A |

Example 76

Reaction Scheme

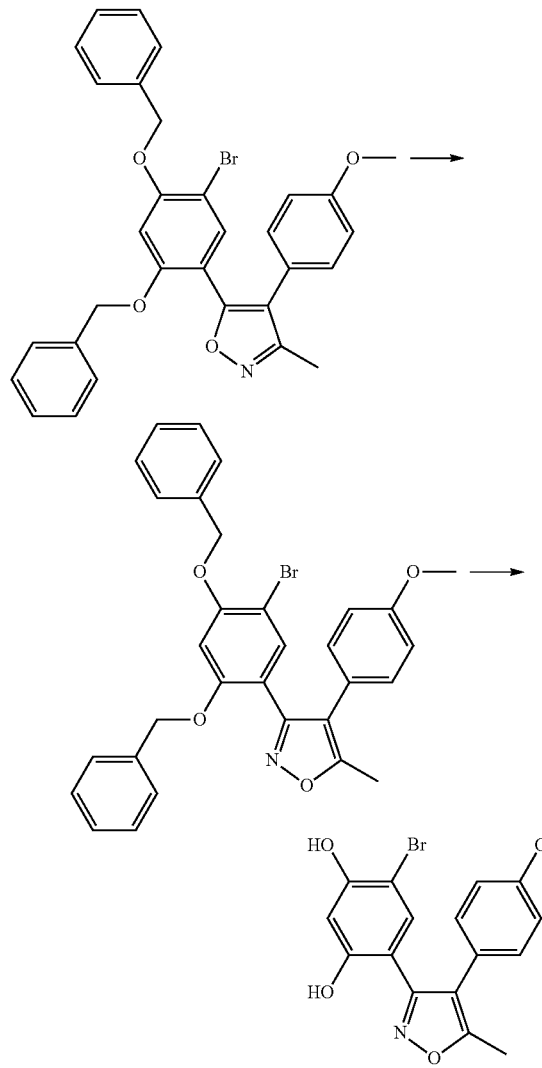

Step 1

3-(2,4-Bis-benzyloxy-5-bromo-phenyl)-4-(4-methoxy-phenyl)-5-methyl-isoxazole

Trimethyloxonium boron trifluoride (Aldrich; 70 mg, 0.47 mmol) was added to a stirred solution of 5-(2,4-Bis-benzyloxy-5-bromo-phenyl)-4-(4-methoxy-phenyl)-3-methyl-isoxazole (Example 3, Step 1) (120 mg, 0.22 mmol) in dichloromethane (3 ml) and stirring was continued for 3 h. The resulting mixture was concentrated in vacuo to leave a white semisolid, which was mixed with hydroxylamine hydrochloride (70 mg, 1.0 mmol), potassium carbonate (120 mg, 0.87 mmol) and methanol (2 ml), and heated at reflux for 18 h. The reaction mixture was partitioned between water (20 ml) and ethyl acetate (2×10 ml) and the combined organic phases were dried over anhydrous magnesium sulphate and evaporated in vacuo to leave an colourless oil. The crude product was purified by column chromatography, silica (10 g), eluting with hexane, followed by diethyl ether/hexane (1:1), to give 3-(2,4-Bis-benzyloxy-5-bromo-phenyl)-4-(4-methoxy-phenyl)-5-methyl-isoxazole as a white solid (44 mg, 37%)

LC retention time 5.55 minutes [M+H]$^+$ 556.0 and 558.0 (Run time 8.00 mins)

N.M.R (Chloroform-d) 7.64 (s ArH) 7.35-6.76 (m 14ArH) 6.34 (sArH) 4.90 (s 2CH$_2$) 4.60 (s 2CH$_2$) 3.79 (s 3CH$_3$) 2.46 (s 3CH$_3$)

Step 2

4-Bromo-6-[4-(4-methoxy-phenyl)-5-methyl-isoxazol-3-yl]-benzene-1,3-diol

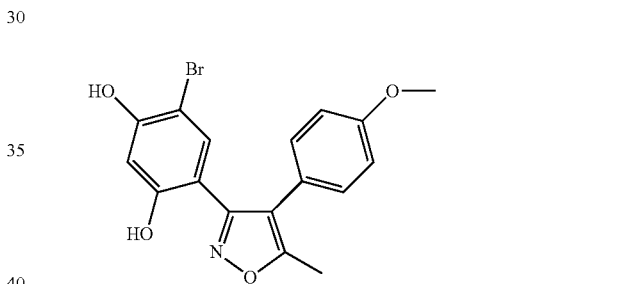

Boron trichloride solution (1M in dichloromethane, 1 ml, 1 mmol) was added to a solution of 3-(2,4-Bis-benzyloxy-5-bromo-phenyl)-4-(4-methoxy-phenyl)-5-methyl-isoxazole (38 mg, 0.068 mmol) in dichloromethane (1 ml), and stirring was continued for 1 h. The reaction mixture was partitioned between water (20 ml) and dichloromethane (2×20 ml) and the combined organic phases were dried over anhydrous magnesium sulphate and concentrated in vacuo to leave a brown oil. The crude product was purified by column chromatography, silica (10 g), eluting with hexane, followed by hexane/diethyl ether (3:1 then 1:1), to give 4-Bromo-6-[4-(4-methoxy-phenyl)-5-methyl-isoxazol-3-yl]-benzene-1,3-diol as a colourless oil (11 mg, 43%).

LC retention time 2.52 minutes [M+H]$^+$ 376.1 and 378.1 (Run time 3.75 mins)

N.M.R (DMSO-d$_6$) 10.40 (s OH) 9.69 (s OH) 7.22 (ArH) 7.10-6.89 (m 4ArH) 6.5 (s ArH) 3.7 (s OCH$_3$) 2.46 (s CH$_3$)

This compound had activity 'A' in the Hsp90 fluorescence polarization assay.

Example 76A

The following compound is commercially available (Interbioscreen) and had activity "B) in the fluorescence polarization assay:

| Example | Structure | MH+ |
|---|---|---|
| 76A | 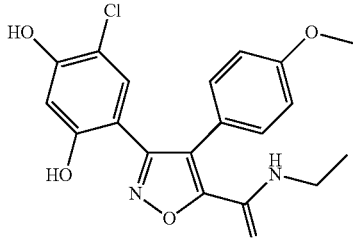 | 343 |
The following compounds were made according to Example 76:
| Example | Structure | MH+ | Hsp90 IC50 |
|---|---|---|---|
| 76B | 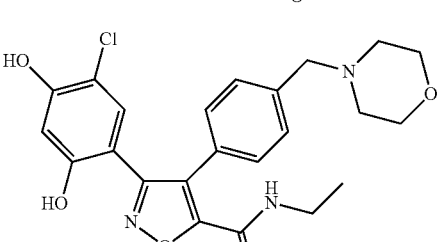 | 389 | A |
| 76C | 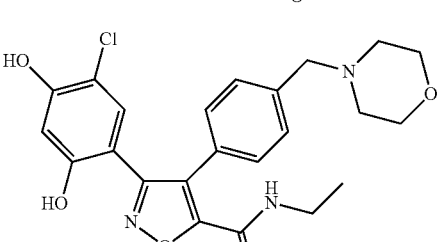 | 458 | A |
Example 77
Preparation of 5-(5-tert-Butyl-2,4-dihydroxy-phenyl)-4-(4-morpholin-4-ylmethyl-phenyl)-isoxazole-3-carboxylic acid ethylamide
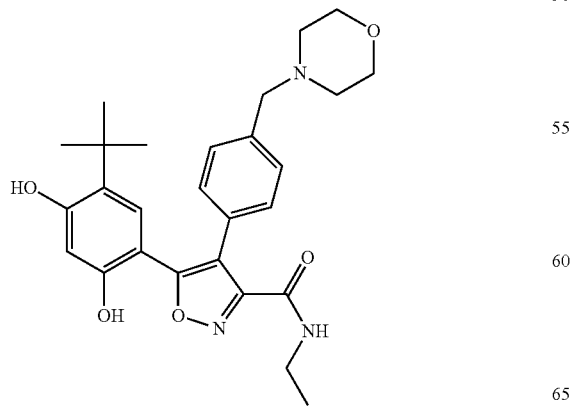
Reaction Scheme:
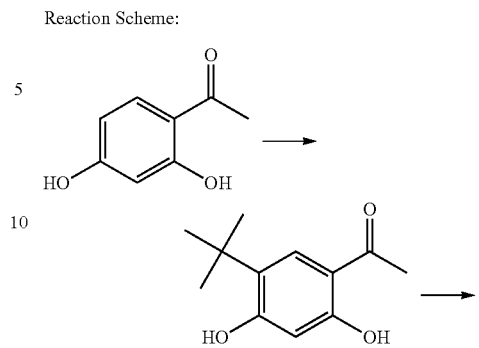
-continued
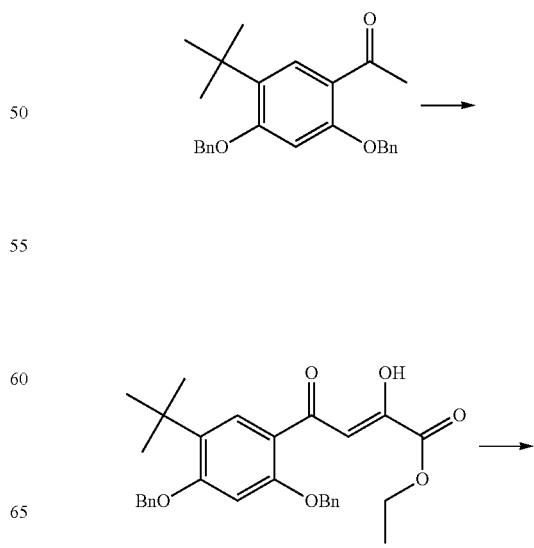

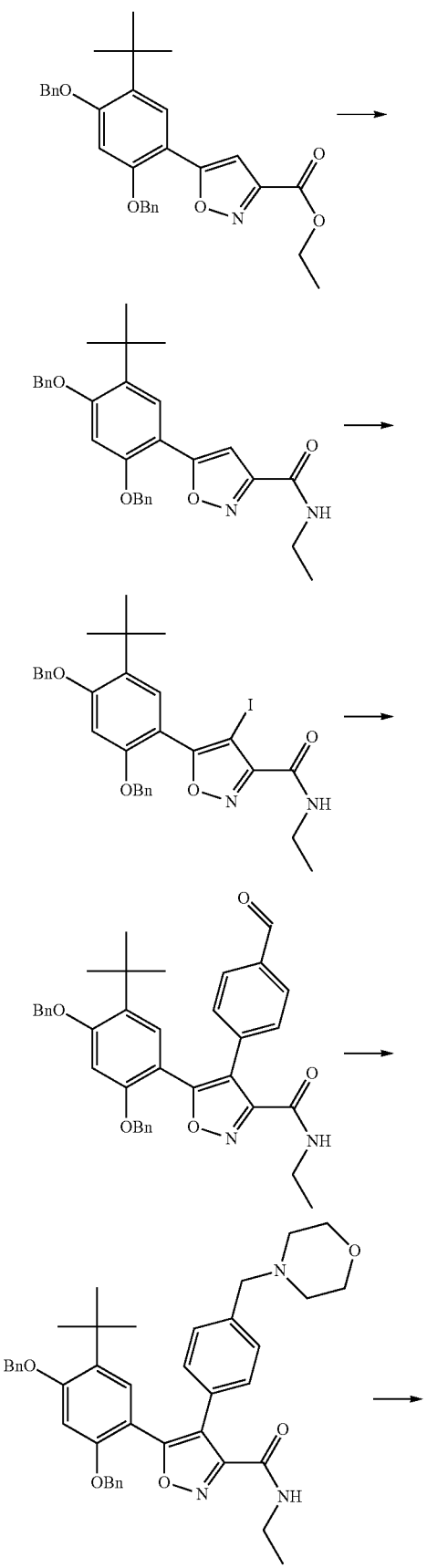

-continued

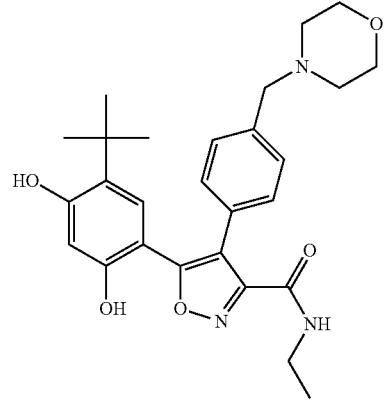

Step 1

1-(5-tert-Butyl-2,4-dihydroxy-phenyl)-ethanone

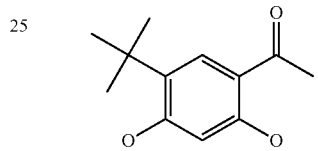

Sulphuric acid (4 ml, 75 mmol) was added to a suspension of 2,4-dihyroxyacetophenone (22.8 g, 150 mmol) in a mixture of 2-methyl-2-propanol (35 g, 470 mmol) and trifluoroacetic acid (80 ml), under a nitrogen atmosphere. The resulting suspension was heated, oil bath temperature 75° C., for ~3 hrs. to give a pale red solution. The resulting solution was allowed to cool and poured into ice/water (350 ml), to give a pale pink precipitate. The solids were removed by filtration and washed with water (600 ml) and hexane (200 ml) to give a pale pink powder. Dried in vacuo (40° C.), to give 1-(5-tert-butyl-2,4-dihydroxy-phenyl)-ethanone as a pale orange powder (28.8 g, 92%).

LC retention time 2.74 minutes [M+H]$^+$ 209.1 (Run time 3.75 mins)

N.M.R (Chloroform-d) 7.35 (s ArH) 6.05 (s ArH) 7.35 (m 2ArH) 2.35 (s 3CH$_3$) 1.15 (s 9CH$_3$)

Step 2

1-(2,4-Bis-benzyloxy-5-tert-butyl-phenyl)-ethanone

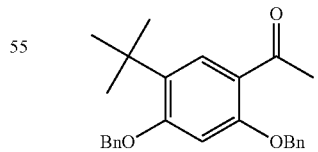

Benzyl bromide (10 ml, 84 mmol) was added to a solution of the acetophenone (13.5 g, 65 mmol) in DMF (50 ml), potassium carbonate (20 g, 145 mmol) was added and the suspension stirred, at room temperature, for ~4 hrs. The resulting suspension was poured into water (200 ml) to give a pale orange precipitate. The solids were removed by filtration and washed with water. The solids were taken up in dichloromethane (150 ml) and the solution was washed with water (2×100 ml) and saturated aqueous sodium chloride solution (100 ml). The solution was dried over anhydrous sodium sulphate and concentrated to a pale red oil.

The oil was taken up in 2-methyl-2-propanol (100 ml) and potassium tert-butoxide (7.5 g, 67 mmol) added, to give a pale yellow precipitate, benzyl bromide (8 ml, 67 mmol) was added and the mixture heated under reflux for ~1 hr. The resulting suspension was allowed to cool and poured into water (250 ml), to give a pale orange precipitate. The solids were removed by filtration and washed with water. The solids were taken up in ethyl acetate (150 ml) and washed with water (2×200 ml) and saturated aqueous sodium chloride solution (100 ml). The solution was dried over anhydrous sodium sulphate and concentrated to a orange semi-solid, trituration with methanol gave a pale pink solid. Solids were removed by filtration and dried in vacuo (40° C.), to give 1-(2,4-bis-benzyloxy-5-tert-butyl-phenyl)-ethanone as a pale pink powder (9.1 g, 36%).

LC retention time 3.03 minutes [M+H]+ 389.3 (Run time 3.75 mins)

N.M.R (Chloroform-d) 7.65 (s ArH) 7.25-7.15 (m 10ArH) 6.35 (s ArH) 4.95 (s 2CH$_2$) 4.9 (s 2CH$_2$) 2.4 (s 3CH$_3$) 1.2 (s 9CH$_3$)

Step 3

4-(2,4-Bis-benzyloxy-5-tert-butyl-phenyl)-2-hydroxy-4-oxo-but-2-enoic acid ethyl ester

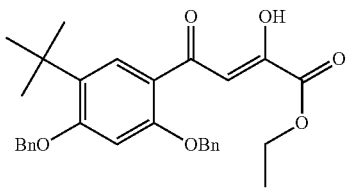 [SMILES: CCOC(=O)/C(O)=C/C(=O)c1cc(C(C)(C)C)c(OCc2ccccc2)cc1OCc1ccccc1]

Sodium ethoxide (2.8 g, 41 mmol) was added to a suspension of the 1-(2,4-bis-benzyloxy-5-tert-butyl-phenyl)-ethanone (7.8 g, 20 mmol) in ethanol (40 ml). Diethyl oxalate (4 ml, 29.5 mmol) was added and the resulting suspension heated under reflux for ~2 hrs. to give a pale red solution. The solution was allowed to cool and poured into water (200 ml), the mixture was acidified with hydrochloric acid (50 ml, 1M) and extracted with dichloromethane (150 ml). The extracts were washed with water (2×200 ml) and saturated aqueous sodium chloride solution (100 ml). The solution was dried over anhydrous sodium sulphate and concentrated to a yellow gum. Trituration with hexane gave a yellow solid. Solids were removed by filtration and washed with hexane and dried in vacuo (40° C.), to give 4-(2,4-Bis-benzyloxy-5-tert-butyl-phenyl)-2-hydroxy-4-oxo-but-2-enoic acid ethyl ester as a yellow powder (9.1 g, 93%).

N.M.R (Chloroform-d) 8.0 (s ArH) 7.5-7.35 (m 11ArH) 6.6 (s ArH) 5.2 (s 2CH$_2$) 5.15 (s 2CH$_2$) 4.3 (q J 7.1 Hz 2CH$_2$) 1.4 (s 9CH$_3$) 1.25 (t J 7.1 Hz 3CH$_3$)

Step 4

5-(2,4-Bis-benzyloxy-5-tert-butyl-phenyl)-isoxazole-3-carboxylic acid ethyl ester

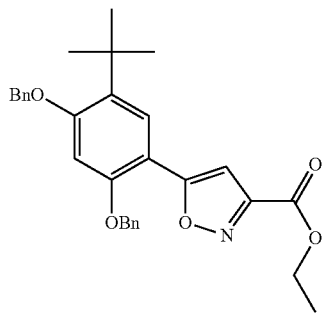 [SMILES: CCOC(=O)c1cc(-c2cc(C(C)(C)C)c(OCc3ccccc3)cc2OCc2ccccc2)on1]

Hydroxylamine hydrochloride (3.6 g, 52 mmol) was added to a solution of 4-(2,4-Bis-benzyloxy-5-tert-butyl-phenyl)-2-hydroxy-4-oxo-but-2-enoic acid ethyl ester (9.0 g, 18.5 mmol) in ethanol (75 ml) and the suspension heated under reflux for ~4 hrs. The resulting solution was allowed to cool and poured into water (200 ml) to give an off-white precipitate. The solids were removed by filtration and taken up in dichloromethane (150 ml). The solution was washed with water (150 ml) and saturated aqueous sodium chloride solution (50 ml). The solution was dried over anhydrous sodium sulphate and concentrated to an off-white solid. Solids were washed with hexane and dried in vacuo (40° C.), to give 5-(2,4-bis-benzyloxy-5-tert-butyl-phenyl)-isoxazole-3-carboxylic acid ethyl ester as a pale brown powder (8.0 g, 89%).

LC retention time 3.13 minutes [M+H]+ 486.5 (Run time 3.75 mins)

N.M.R (Chloroform-d) 7.85 (s ArH) 7.4-7.25 (m 10ArH) 6.9 (s ArH) 6.5 (s ArH) 5.1 (s 2CH$_2$) 5.0 (s 2CH$_2$) 4.35 (q J 7.1 Hz 2CH$_2$) 1.4 (s 9CH$_3$) 1.35 (t J 7.1 Hz 3CH$_3$)

Step 5

5-(2,4-Bis-benzyloxy-5-tert-butyl-phenyl)-isoxazole-3-carboxylic acid ethylamide

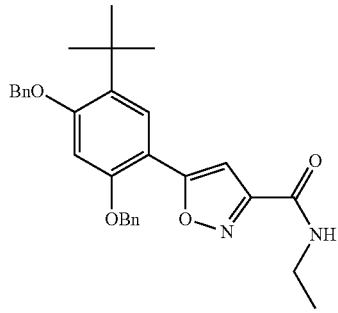 [SMILES: CCNC(=O)c1cc(-c2cc(C(C)(C)C)c(OCc3ccccc3)cc2OCc2ccccc2)on1]

5-(2,4-Bis-benzyloxy-5-tert-butyl-phenyl)-isoxazole-3-carboxylic acid ethyl ester (10.0 g, 20.6 mmol) was added to a solution of ethylamine in methanol (60 ml, 2.0M) and the suspension heated, oil bath temperature 75° C., for ~2 hrs. The resulting solution was allowed to cool and concentrated to a pale brown oil, dichloromethane (150 ml) was added and the solution washed with water (100 ml) and saturated aqueous sodium chloride solution (75 ml). The solution was dried over anhydrous sodium sulphate and concentrated to a brown oil, solidified on standing (9.9 g, ~quant).

LC retention time 3.02 minutes [M+H]+ 485.3 (Run time 3.75 mins)

N.M.R (Chloroform-d) 7.8 (s ArH) 7.4-7.2 (m 10ArH) 7.0 (s ArH) 6.75 (br t J 5.4 Hz NH) 6.5 (s ArH) 5.1 (s 2CH$_2$) 5.0 (s 2CH$_2$) 3.4 (dq J 5.4 Hz, 7.1 Hz 2 CH$_2$) 1.35 (s 9CH$_3$) 1.15 (t J 7.1 Hz 3CH$_3$)

Step 6

5-(2,4-Bis-benzyloxy-5-tert-butyl-phenyl)-4-iodo-isoxazole-3-carboxylic acid ethylamide

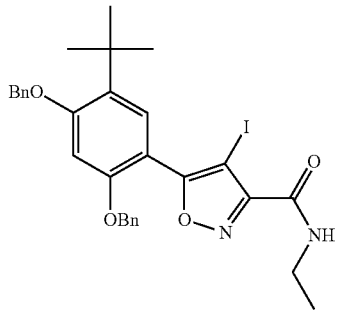

N-iodosuccinimide (9.0 g, 40 mmol) was added to a suspension of 5-(2,4-Bis-benzyloxy-5-tert-butyl-phenyl)-isoxazole-3-carboxylic acid ethylamide (9.9 g, 20.4 mmol) in acetonitrile (60 ml). Ammonium cerium nitrate (0.25 g, 0.46 mmol) was added and the suspension stirred for ~18 hrs. The resulting suspension was concentrated and the residue taken up in dichloromethane (125 ml). The resulting solution was washed aqueous sodium metabisulphite solution (2×100 ml, 5%), water (100 ml) and saturated aqueous sodium chloride solution (100 ml). The solution was dried over anhydrous sodium sulphate and concentrated to a pale red gum. Trituration with ethanol (25 ml) gave an off-white solid, solids were removed by filtration and washed with ethanol. Dried in vacuo (40° C.), to give 5-(2,4-Bis-benzyloxy-5-tert-butyl-phenyl)-4-iodo-isoxazole-3-carboxylic acid ethylamide as an off-white powder (7.75 g, 62%).

LC retention time 3.07 minutes [M+H]+ 611.2 (Run time 3.75 mins)

N.M.R (Chloroform-d) 7.45-7.25 (m 11ArH) 6.8 (br t J 5.4 Hz NH) 6.6 (s ArH) 5.05 (s 4CH$_2$) 3.5 (dq J 5.4 Hz, 7.1 Hz 2CH$_2$) 1.35 (s 9CH$_3$) 1.2 (t J 7.1 Hz 3CH$_3$)

Step 7

5-(2,4-Bis-benzyloxy-5-tert-butyl-phenyl)-4-(4-formyl-phenyl)-isoxazole-3-carboxylic acid ethylamide

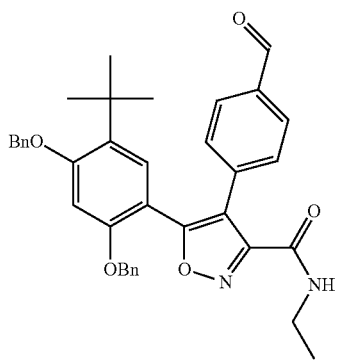 [SMILES: CCNC(=O)c1noc(-c2cc(C(C)(C)C)c(OCc3ccccc3)cc2OCc2ccccc2)c1-c1ccc(C=O)cc1]

Aqueous potassium phosphate (25 ml, 1.2M) solution was added to a solution of 5-(2,4-bis-benzyloxy-5-tert-butyl-phenyl)-4-iodo-isoxazole-3-carboxylic acid ethylamide (6.1 g, 10 mmol) and 4-formylphenyl boronic acid (2.35 g, 15.7 mmol) in 1,4-Dioxan (75 ml), under a nitrogen atmosphere. Dichloro-bis(tri-o-tolyl phosphine)palladium(II) (cat.) was added and the mixture heated, oil bath temperature 100° C. for ~1 hr. The mixture was allowed to cool, and the aqueous layer separated and extracted with ethyl acetate (100 ml). The combined organics were concentrated to give a pale brown gum.

The crude product was purified by column chromatography, silica (600 ml), eluting with ethyl acetate/hexane (1:3), to give 5-(2,4-Bis-benzyloxy-5-tert-butyl-phenyl)-4-(4-formyl-phenyl)-isoxazole-3-carboxylic acid ethylamide as a pale yellow foam (5.18 g, 88%).

LC retention time 3.01 minutes [M+H]+ 589.4 (Run time 3.75 mins)

N.M.R (Chloroform-d) 9.75 (s CHO) 7.5 (d J 6.9 Hz 2ArH) 7.2 (d J 6.9 Hz 2ArH) 7.15-7.0 (m 8ArH) 6.8 (m 2ArH) 6.65 (br t J 5.4 Hz NH) 6.2 (s ArH) 4.8 (s 2CH$_2$) 4.5 (s 2CH$_2$) 3.2 (dq J 5.4 Hz, 7.1 Hz 2CH$_2$) 1.1 (s 9CH$_3$) 1.05 (t J 7. Hz 3CH$_3$)

Step 8

5-(2,4-Bis-benzyloxy-5-tert-butyl-phenyl)-4-(4-morpholin-4-ylmethyl-phenyl)-isoxazole-3-carboxylic acid ethylamide

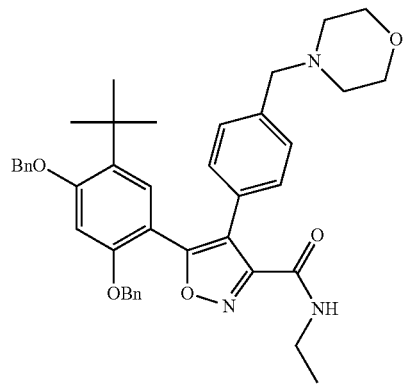 [SMILES: CCNC(=O)c1noc(-c2cc(C(C)(C)C)c(OCc3ccccc3)cc2OCc2ccccc2)c1-c1ccc(CN2CCOCC2)cc1]

Sodium cyanoborohydride (65 mg, 1.03 mmol) was added to a solution of 5-(2,4-Bis-benzyloxy-5-tert-butyl-phenyl)-4-(4-formyl-phenyl)-isoxazole-3-carboxylic acid ethylamide (125 mg, 0.21 mmol), morpholine (50 μl, 57 mmol) and acetic acid (cat.) in methanol (4 ml) and the solution stirred for ~72 hrs. Dichloromethane (50 ml) was added and the solution washed with water (2×50 ml) and saturated aqueous sodium chloride solution (50 ml). The solution was dried over anhydrous sodium sulphate and concentrated to a colourless gum.

The crude product was purified by column chromatography, silica (20 g), eluting with ethyl acetate/hexane (1:1), to give 5-(2,4-Bis-benzyloxy-5-tert-butyl-phenyl)-4-(4-morpholin-4-ylmethyl-phenyl)-isoxazole-3-carboxylic acid ethylamide as a colourless oil (35 mg, 25%).

LC retention time 2.56 minutes [M+H]+ 660.8 (Run time 3.75 mins)

N.M.R (Chloroform-d) 7.35-7.05 (m 15ArH) 6.7 (br t J 5.4 Hz NH) 6.4 (s ArH) 4.9 (s 2CH$_2$) 4.75 (s 2CH$_2$) 3.6 (t J 4.5 Hz 4CH$_2$) 3 (s 2CH$_2$) 3.35 (dq J 5.4 Hz, 7.1 Hz 2CH$_2$) 2.35 (br s 4CH$_2$) 1.15 (t J 7.1 Hz 3CH$_3$) 1.1 (s 9CH$_3$)

Step 9

5-(5-tert-Butyl-2,4-dihydroxy-phenyl)-4-(4-morpholin-4-ylmethyl-phenyl)-isoxazole-3-carboxylic acid ethylamide

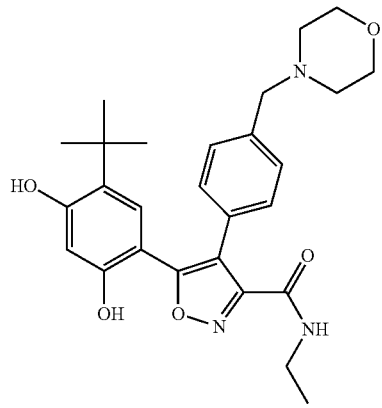 [SMILES: CCNC(=O)c1noc(-c2cc(C(C)(C)C)c(O)cc2O)c1-c1ccc(CN2CCOCC2)cc1]

Boron trichloride (1 ml, 1.0M in dichloromethane) solution was added to a solution of 5-(2,4-Bis-benzyloxy-5-tert-butyl-phenyl)-4-(4-morpholin-4-ylmethyl-phenyl)-isoxazole-3-carboxylic acid ethylamide (35 mg, 0.05 mmol) in dichloromethane (1 ml) at −20° C. (ice/methanol), under a nitrogen atmosphere. The resulting solution was stirred at 0° C. (ice/water) for ~90 mins. Methanol (2 ml) was added and the solution concentrated to a brown gum.

The crude product was purified by preparative HPLC, to give 5-(5-tert-Butyl-2,4-dihydroxy-phenyl)-4-(4-morpholin-4-ylmethyl-phenyl)-isoxazole-3-carboxylic acid ethylamide as a white powder (formate salt) (21 mg, 75%).

LC retention time 1.97 minutes [M+H]$^+$ 480.5 (Run time 3.75 mins)

N.M.R (DMSO-d$_6$) 8.8 (t J 5.6 Hz NH) 7.25 (d J 7.2 Hz 2ArH) 7.15 (d J 7.2 Hz 2ArH) 6.7 (s ArH) 6.45 (s ArH) 3.45 (br s 4CH$_2$) 3.2 (dq J 5.6 Hz, 7.2 Hz 2CH$_2$) 2.3 (br s 4CH$_2$) 1.1 (s 9CH$_3$) 1.05 (t J 7.2 Hz 3CH$_3$)

This compound had activity 'A' in the Hsp900 fluorescence polarization assay.

In a similar manner to the preparation of the compound of example 77, examples 77a-f were prepared.

| Example | Structure | MH+ | Hsp90 IC50 |
|---|---|---|---|
| 77a | 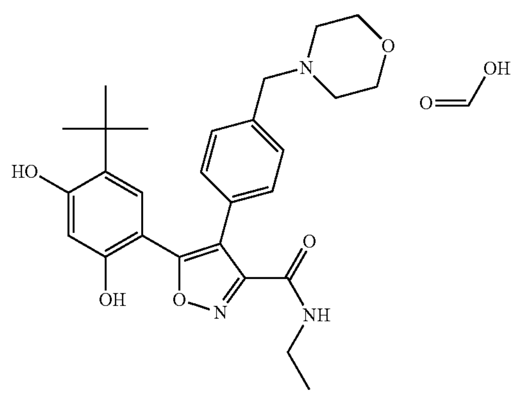 | 480 | A |
| 77b | 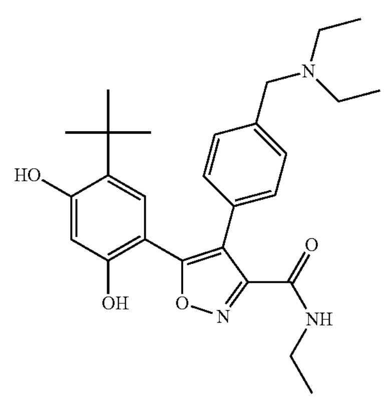 [SMILES: CCNC(=O)c1noc(-c2cc(C(C)(C)C)c(O)cc2O)c1-c1ccc(CN(CC)CC)cc1] | 466 | A |

-continued

| Example | Structure | MH+ | Hsp90 IC50 |
|---|---|---|---|
| 77c | 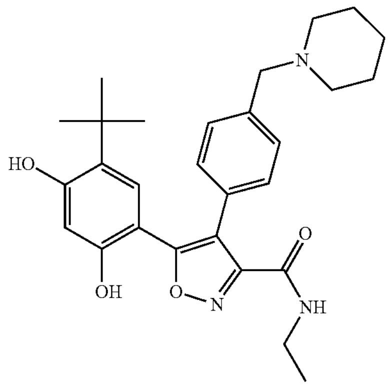 [SMILES: CCNC(=O)c1noc(-c2cc(C(C)(C)C)c(O)cc2O)c1-c1ccc(CN2CCCCC2)cc1] | 478 | A |
| 77d | 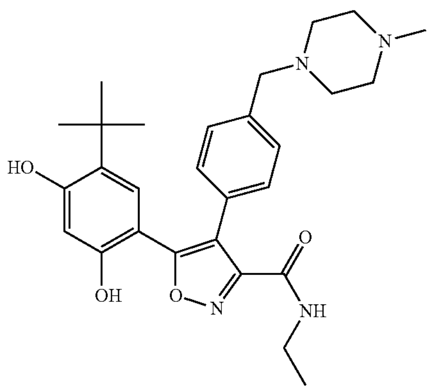 [SMILES: CCNC(=O)c1noc(-c2cc(C(C)(C)C)c(O)cc2O)c1-c1ccc(CN2CCN(C)CC2)cc1] | 493 | A |
| 77e | 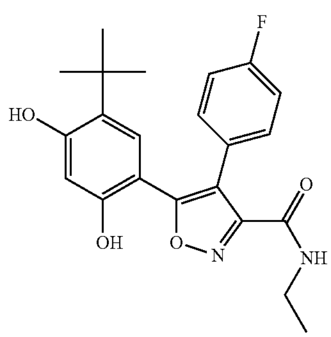 [SMILES: CCNC(=O)c1noc(-c2cc(C(C)(C)C)c(O)cc2O)c1-c1ccc(F)cc1] | 399 | A |
| 77f | 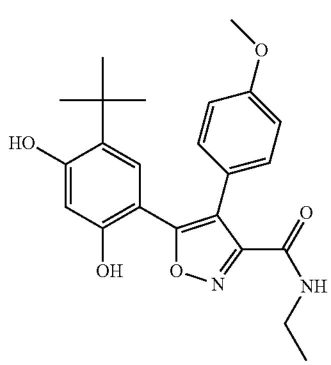 [SMILES: CCNC(=O)c1noc(-c2cc(C(C)(C)C)c(O)cc2O)c1-c1ccc(OC)cc1] | 411 | A |

Example 78
5-(2,4-Dihydroxy-5-isopropyl-phenyl)-4-(4-morpholin-4-ylmethyl-phenyl)-isoxazole-3-carboxylic acid ethylamide
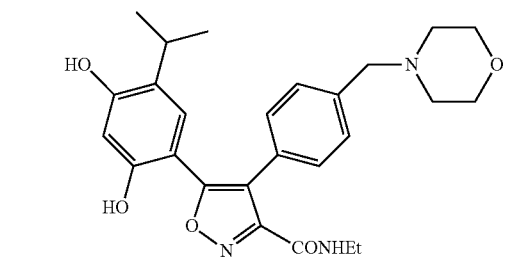
Reaction Scheme
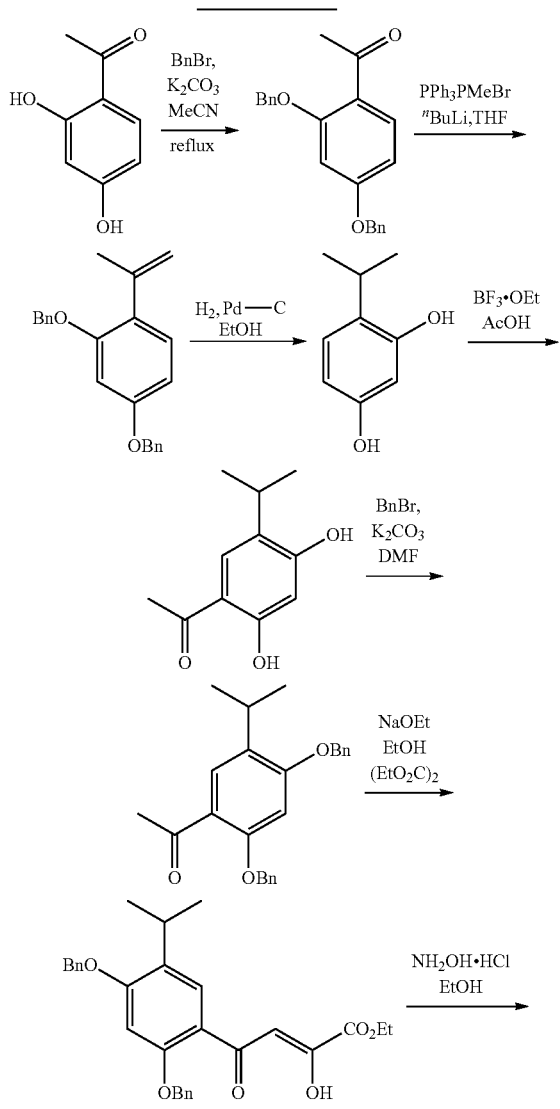
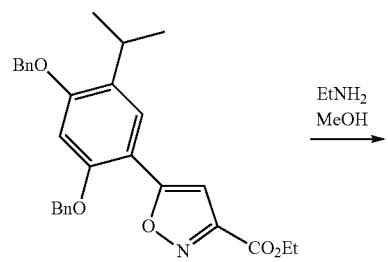
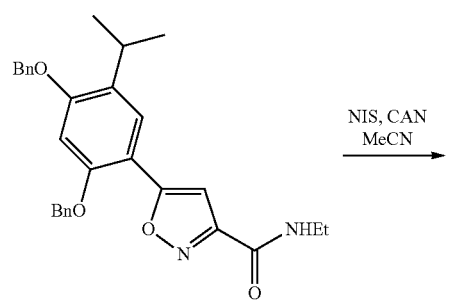
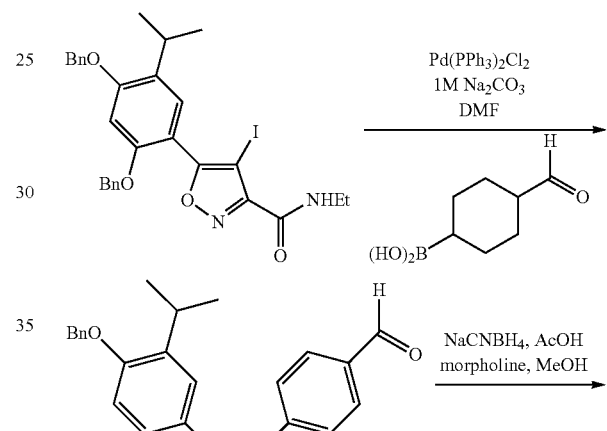
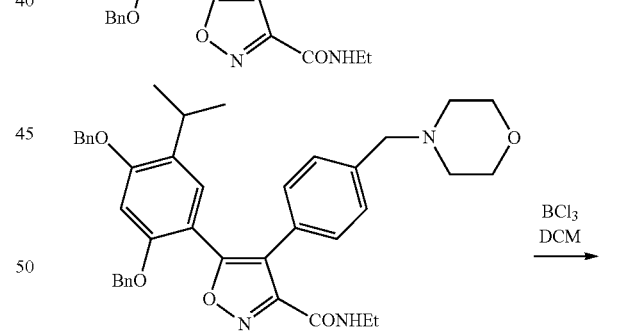
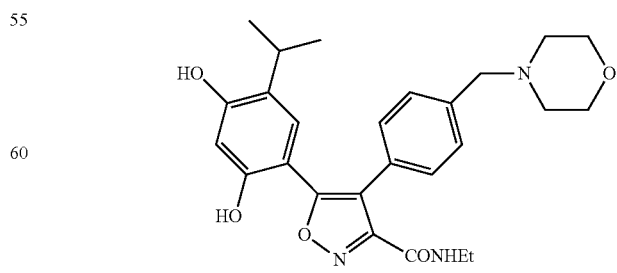

Step 1

1-(2,4-Bis-benzyloxy-phenyl)-ethanone

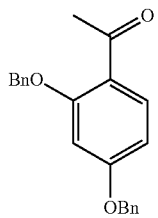

Potassium carbonate (2.5 eq) was added to a solution of 2',4'-dihydroxyacetophenone (1 eq) in acetonitrile (400 mL), and the suspension stirred at room temperature. Benzyl bromide (2.5 eq) was added drop wise over 10 minutes and the mixture heated at reflux for 18 hours. The mixture was cooled and evaporated in vacuo to give slurry. The slurry was partitioned between water and ethyl acetate, and the layers were separated. The aqueous layer was further extracted with dichloromethane and the organic extracts were combined, dried (MgSO$_4$) and evaporated in vacuo. The product was triturated with hexane, filtered and washed with cold hexane and dried in vacuo at 45° C. to give 1-(2,4-Bis-benzyloxy-phenyl)-ethanone as a white powder.

LC retention time 2.704 min [M+H]$^+$ 333.3

Step 2

2,4-Bis-benzyloxy-1-isopropenyl-benzene

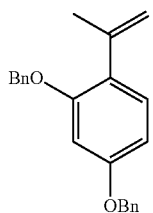

Methyltriphenylphosphonium bromide (1.1 eq) was suspended in an. THF and cooled to 0° C. under nitrogen. 1.6M $^n$Butyllithium in hexanes (1.1 eq) was added drop wise, and stirred for 30 minutes. 1-(2,4-Bis-benzyloxy-phenyl)-ethanone (1 eq) was dissolved in an. THF and added drop wise to the suspension. When addition was completed, the ice bath was removed and the reaction mixture was stirred at room temperature under nitrogen overnight. Methanol was added to the reaction mixture and the resulting solution was evaporated in vacuo. Hexane was added to the resulting oil and heated to reflux for 30 minutes, then filtered through Celite. The liquor was evaporated in vacuo to give an oil which was purified by column chromatography, eluting with 30% EtOAc in hexane, to give 2,4-Bis-benzyloxy-1-isopropenyl-benzene. R$_f$ retention time 0.722, 3:1 Hexane:EtOAc.

Step 3

4-Isopropyl-benzene-1,3-diol

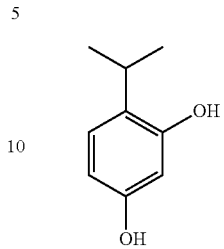

2,4-Bis-benzyloxy-1-isopropenyl-benzene was taken up in solution in ethanol and added to 10% palladium on carbon, which had been pre-wetted with water. Hydrogen was introduced to the flask and the mixture was allowed to shake for 16 hours. The catalyst was filtered from the reaction mixture, by a suitable method, and the liquor was concentrated in vacuo, to give 4-isopropyl-benzene-1,3-diol as a white crystalline solid.

LC retention time 2.088 min [M+H]$^+$ 153.1

Step 4

1-(2,4-Dihydroxy-5-isopropyl-phenyl)-ethanone

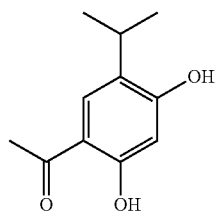

4-Isopropyl-benzene-1,3-diol (1 eq) was taken up in BF$_3$.OEt$_2$ (6 eq) and acetic acid was added (2 eq). The solution was heated for 16 hours at 90° C. than allowed to cool to room temperature. The solution was added drop wise to 10% NaOAc (aq) and allowed to stand for 4 hours, before being extracted in to EtOAc. The organic phases were combined and washed with sat. NaHCO$_3$ (aq), then dried over MgSO$_4$, filtered and concentrated in vacuo. The residual oil was purified by column chromatography, eluting with dichloromethane, to give 1-(2,4-Dihydroxy-5-isopropyl-phenyl)-ethanone as a white solid.

LC retention time 2.633 min [M+H]+ 195.1

Step 5

1-(2,4-Bis-benzyloxy-5-isopropyl-phenyl)-ethanone

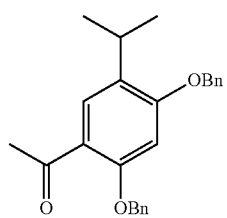 [SMILES: CC(=O)c1cc(C(C)C)c(OCc2ccccc2)cc1OCc1ccccc1]

1-(2,4-Dihydroxy-5-isopropyl-phenyl)-ethanone (1 eq) was dissolved in DMF and potassium carbonate (2.2 eq)

then benzyl bromide (2.2 eq) were added. The suspension was heated, with stirring to 150° C., under nitrogen, for 16 hrs. The solution was cooled to room temperature and the mixture was poured into 1MHCl (aq) then extracted in to ethyl acetate. The organic phases were combined and washed again with 1MHCl (aq) then five times with brine solution. The organic phase was dried over MgSO4, filtered and concentrated in vacuo, to give a solid, which was purified by diethyl ether hexane (1:1) trituration to give 1-(2,4-Bis-benzyloxy-5-isopropyl-phenyl)-ethanone.

LC retention time 3.575 min [M+H]+ 375.2

Step 6

4-(2,4-Bis-benzyloxy-5-isopropyl-phenyl)-2-hydroxy-4-oxo-but-2-enoic acid ethyl ester

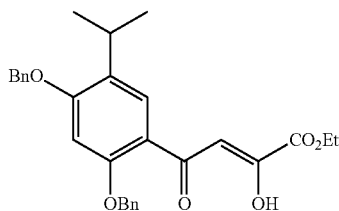 [SMILES: CCOC(=O)/C(O)=C/C(=O)c1cc(C(C)C)c(OCc2ccccc2)cc1OCc1ccccc1]

Sodium (2.8 eq) was added to ethanol under nitrogen at room temperature and stirred for 25 minutes to generate sodium ethoxide. 1-(2,4-Bis-benzyloxy-5-isopropyl-phenyl)-ethanone (1 eq) was dissolved in further ethanol and added to the sodium ethoxide solution. Diethyl oxalate (1.64 eq) was added and the reaction mixture heated to reflux for 4 hours. The mixture was allowed to cool to room temperature and enough 1MHCl (aq) was added to acidify the reaction mixture, which was then concentrated in vacuo. The resulting gum was partitioned between dichloromethane and brine, and the organic phase was dried over MgSO4, filtered and evaporated in vacuo to give 4-(2,4-Bis-benzyloxy-5-isopropyl-phenyl)-2-hydroxy-4-oxo-but-2-enoic acid ethyl ester as a yellow gum.

LC retention time 3.057 min [M+H]+ 475

Step 7

5-(2,4-Bis-benzyloxy-5-isopropyl-phenyl)-isoxazole-3-carboxylic acid ethyl ester

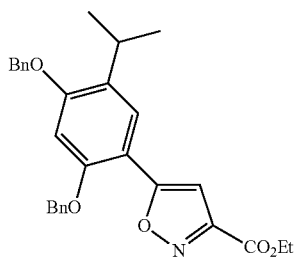 [SMILES: CCOC(=O)c1cc(-c2cc(C(C)C)c(OCc3ccccc3)cc2OCc2ccccc2)on1]

4-(2,4-Bis-benzyloxy-5-isopropyl-phenyl)-2-hydroxy-4-oxo-but-2-enoic acid ethyl ester (1 eq) was dissolved in ethanol with stirring. Hydroxylamine hydrochloride (1.2 eq) was added and the solution was heated to reflux for 4 hours under a nitrogen atmosphere. The reaction mixture was cooled to room temperature and concentrated in vacuo. The residue was partitioned between brine and dichloromethane. The organic phase was dried over MgSO4, filtered and concentrated in vacuo to give 5-(2,4-Bis-benzyloxy-5-isopropyl-phenyl)-isoxazole-3-carboxylic acid ethyl ester as a solid.

LC retention time 3.059 min [M+H]+ 472

Step 8

5-(2,4-Bis-benzyloxy-5-isopropyl-phenyl)-isoxazole-3-carboxylic acid ethylamide

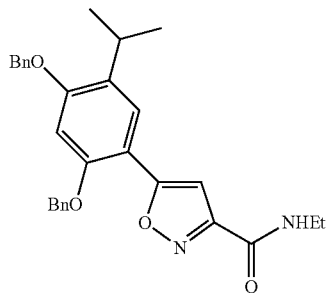

5-(2,4-Bis-benzyloxy-5-isopropyl-phenyl)-isoxazole-3-carboxylic acid ethyl ester was dissolved in excess 2-Methylamine in methanol and heated in the Smith Synthesiser microwave at 120° C. for 600 seconds. The solution was concentrated in vacuo to give a solid which was purified by hexane trituration, to give 5-(2,4-Bis-benzyloxy-5-isopropyl-phenyl)-isoxazole-3-carboxylic acid ethylamide.

LC retention time 2.979 min [M+H]+ 471.3

Step 9

5-(2,4-Bis-benzyloxy-5-isopropyl-phenyl)-4-iodo-isoxazole-3-carboxylic acid ethylamide

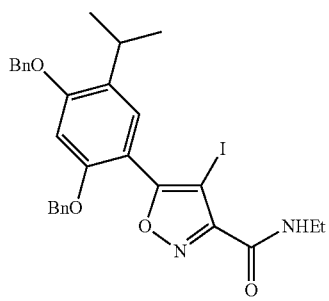

5-(2,4-Bis-benzyloxy-5-isopropyl-phenyl)-isoxazole-3-carboxylic acid ethylamide (1 eq) was dissolved in an. acetonitrile and N-iodosuccinimide (2.0 eq), followed by ceric ammonium nitrate (0.05 eq) were added, and the solution was stirred at room temperature overnight. The reaction mixture was concentrated in vacuo and the resulting gum was partitioned between ethyl acetate and brine. The organic phase was dried over MgSO4, filtered and concentrated in vacuo. The residue was purified by column chromatography, eluting with 9:1 hexane:ethyl acetate, to give 5-(2,4-Bis-benzyloxy-5-isopropyl-phenyl)-4-iodo-isoxazole-3-carboxylic acid ethylamide as an oil.

LC retention time 2.975 min [M+H]+ 597.2

Step 10

5-(2,4-Bis-benzyloxy-5-isopropyl-phenyl)-4-iodo-isoxazole-3-carboxylic acid ethylamide

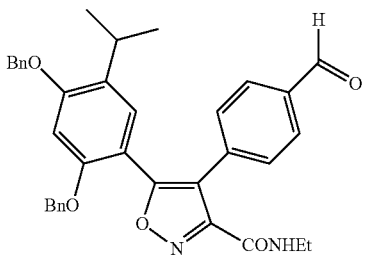

5-(2,4-Bis-benzyloxy-5-isopropyl-phenyl)-4-iodo-isoxazole-3-carboxylic acid ethylamide (1 eq) was dissolved in an. DMF. 1MNa$_2$CO$_3$ (aq) was added, followed by 4-formylphenylboronic acid (2 eq) and then catalytic PdCl2 (PPh3)2. Nitrogen was bubbled through the solution for ten minutes at ambient temperature, after which time, the temperature was elevated to 80° C. under a nitrogen atmosphere, for 15 minutes. The reaction mixture was allowed to cool to room temperature and the reaction mixture was diluted with ethyl acetate. This solution was washed with brine, then dried over MgSO$_4$, filtered and concentrated in vacuo to give an oil. Purified by column chromatography, eluting with 10% EtOAc in hexane, to give 5-(2,4-Bis-benzyloxy-5-isopropyl-phenyl)-4-iodo-isoxazole-3-carboxylic acid ethylamide as a white solid.

LC retention time 2.981 min [M+H]$^+$ 575.3

Step 11

5-(2,4-Bis-benzyloxy-5-isopropyl-phenyl)-4-(4-morpholin-4-ylmethyl-phenyl)-isoxazole-3-carboxylic acid ethylamide

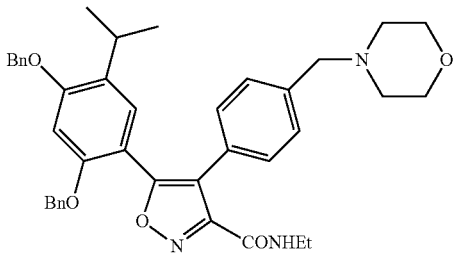

5-(2,4-Bis-benzyloxy-5-isopropyl-phenyl)-4-iodo-isoxazole-3-carboxylic acid ethylamide (1 eq) was dissolved in methanol and powdered 3A sieves were added. Morpholine (2 eq) was added, followed by sodium cyanoborohydride (2 eq). Acetic acid (5 eq) was added drop wise and the suspension was stirred under nitrogen at ambient temperature for 16 hours. The reaction mixture was diluted with DCM and washed with sat. NaHCO$_3$(aq). The organic phase was dried over MgSO$_4$, filtered and concentrated in vacuo. The resulting gum was purified by flash chromatography, eluting with 1% MeOH in DCM to give 5-(2,4-Bis-benzyloxy-5-isopropyl-phenyl)-4-(4-morpholin-4-ylmethyl-phenyl)-isoxazole-3-carboxylic acid ethylamide as a colourless oil.

LC retention time 4.42 min [M+H]$^+$ 646.2 method B

Step 12

5-(2,4-Dihydroxy-5-isopropyl-phenyl)-4-(4-morpholin-4-ylmethyl-phenyl)-isoxazole-3-carboxylic acid ethylamide

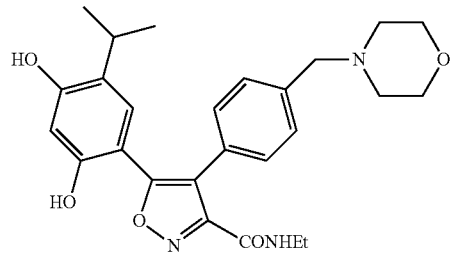

5-(2,4-Bis-benzyloxy-5-isopropyl-phenyl)-4-(4-morpholin-4-ylmethyl-phenyl)-isoxazole-3-carboxylic acid ethylamide (1 eq) was dissolved in an. DCM and under a nitrogen atmosphere, was cooled to 0° C. 1MBCl$_3$ in DCM was added drop wise and the solution was stirred under these conditions for 30 minutes. Methanol (2 ml) was added and the reaction mixture was concentrated in vacuo. Purification of the sample by preparative LC/MS gave 5-(2,4-dihydroxy-5-isopropyl-phenyl)-4-(4-morpholin-4-ylmethyl-phenyl)-isoxazole-3-carboxylic acid ethylamide as a white solid.

LC retention time 1.991 min [M+H]$^+$ 466.3

This compound had activity 'A' in the Hsp90 fluorescence polarization assay.

In a similar manner to the preparation of the compound of example 78, examples 78a-u were prepared.

| Example | Structure | MH+ | Hsp90 IC50 |
|---|---|---|---|
| 78a | 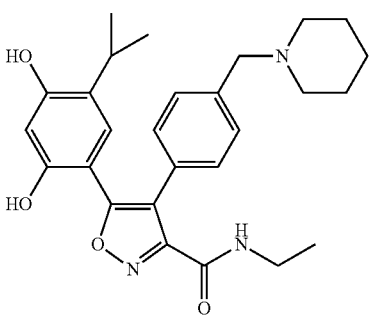 [SMILES: CCNC(=O)c1noc(-c2cc(C(C)C)c(O)cc2O)c1-c1ccc(CN2CCCCC2)cc1] | 464 | A |

-continued

| Example | Structure | MH+ | Hsp90 IC50 |
|---|---|---|---|
| 78b | 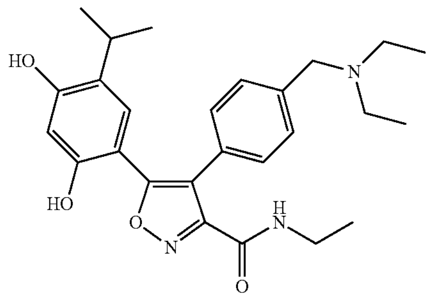 [SMILES: CCNC(=O)c1noc(-c2cc(C(C)C)c(O)cc2O)c1-c1ccc(CN(CC)CC)cc1] | 452 | A |
| 78c | 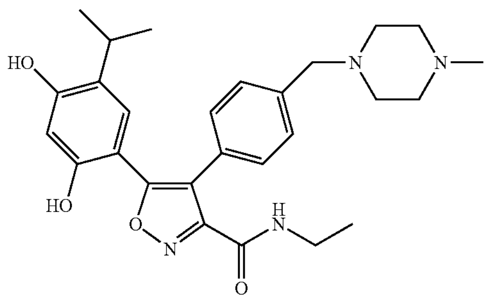 [SMILES: CCNC(=O)c1noc(-c2cc(C(C)C)c(O)cc2O)c1-c1ccc(CN2CCN(C)CC2)cc1] | 479 | A |
| 78d | 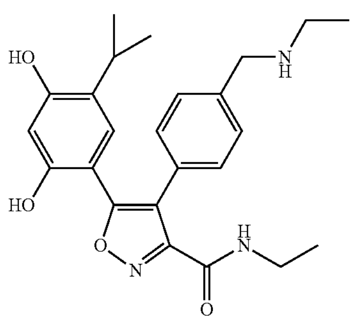 [SMILES: CCNCc1ccc(-c2c(C(=O)NCC)noc2-c2cc(C(C)C)c(O)cc2O)cc1] | 424 | A |
| 78e | 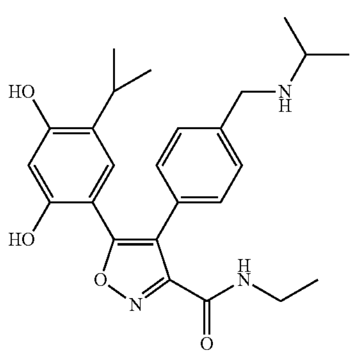 [SMILES: CCNC(=O)c1noc(-c2cc(C(C)C)c(O)cc2O)c1-c1ccc(CNC(C)C)cc1] | 439 | A |

| Example | Structure | MH+ | Hsp90 IC50 |
|---|---|---|---|
| 78f | 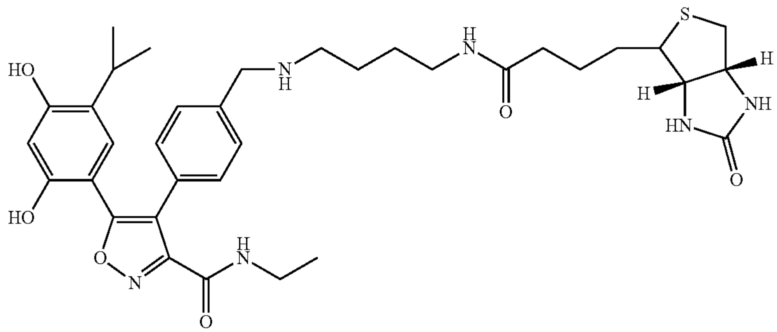 [SMILES: CCNC(=O)c1noc(-c2cc(C(C)C)c(O)cc2O)c1-c1ccc(CNCCCCNC(=O)CCCC2SC[C@@H]3NC(=O)N[C@H]23)cc1] | 680 | A |
| 78g | 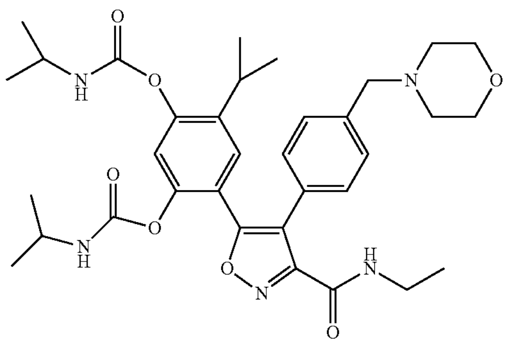 [SMILES: CCNC(=O)c1noc(-c2cc(C(C)C)c(OC(=O)NC(C)C)cc2OC(=O)NC(C)C)c1-c1ccc(CN2CCOCC2)cc1] | 636 | Pro-drug see Example 78v |
| 78h | 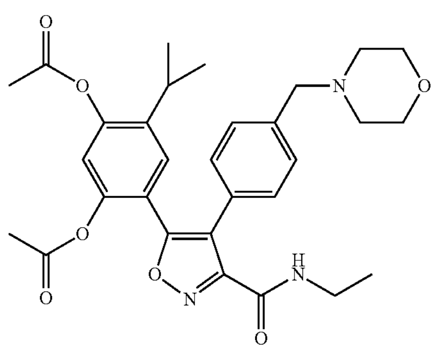 [SMILES: CCNC(=O)c1noc(-c2cc(C(C)C)c(OC(C)=O)cc2OC(C)=O)c1-c1ccc(CN2CCOCC2)cc1] | 550 | Pro-drug see Example 78v |
| 78i | 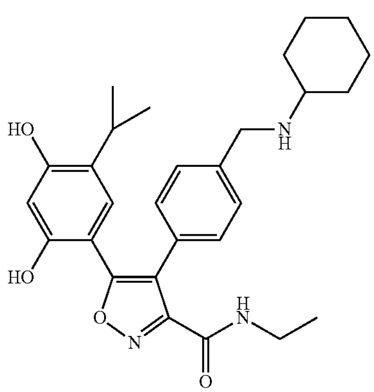 [SMILES: CCNC(=O)c1noc(-c2cc(C(C)C)c(O)cc2O)c1-c1ccc(CNC2CCCCC2)cc1] | 478 | A |

-continued

| Example | Structure | MH+ | Hsp90 IC50 |
|---|---|---|---|
| 78j | 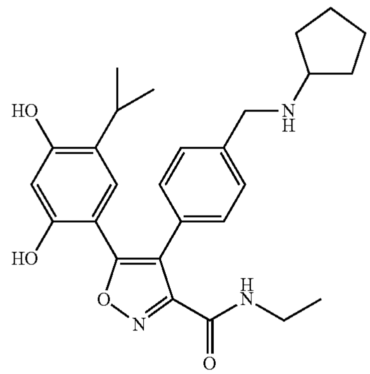 [SMILES: CCNC(=O)c1noc(-c2cc(C(C)C)c(O)cc2O)c1-c1ccc(CNC2CCCC2)cc1] | 464 | A |
| 78k | 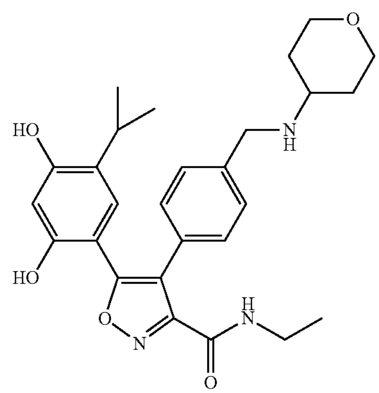 [SMILES: CCNC(=O)c1noc(-c2cc(C(C)C)c(O)cc2O)c1-c1ccc(CNC2CCOCC2)cc1] | 480 | A |
| 78l | 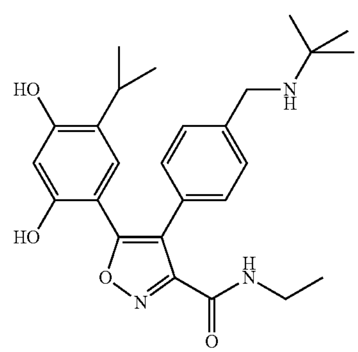 [SMILES: CCNC(=O)c1noc(-c2cc(C(C)C)c(O)cc2O)c1-c1ccc(CNC(C)(C)C)cc1] | 452 | A |
| 78m | 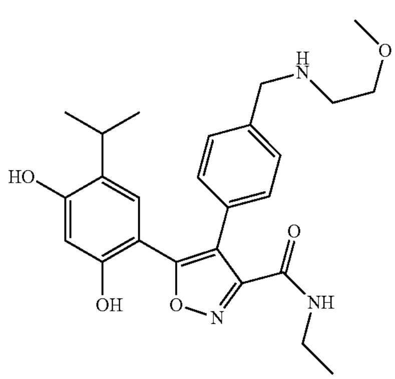 [SMILES: CCNC(=O)c1noc(-c2cc(C(C)C)c(O)cc2O)c1-c1ccc(CNCCOC)cc1] | 454 | A |

-continued

| Example | Structure | MH+ | Hsp90 IC50 |
|---|---|---|---|
| 78n | 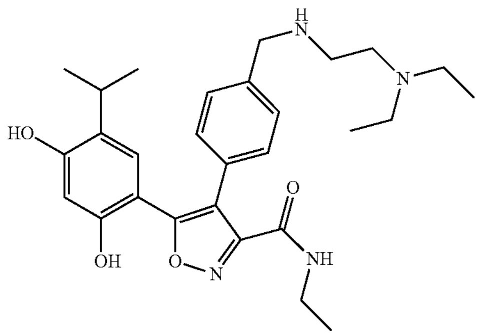 [SMILES: CCNC(=O)c1noc(-c2cc(C(C)C)c(O)cc2O)c1-c1ccc(CNCCN(CC)CC)cc1] | 495 | A |
| 78p | 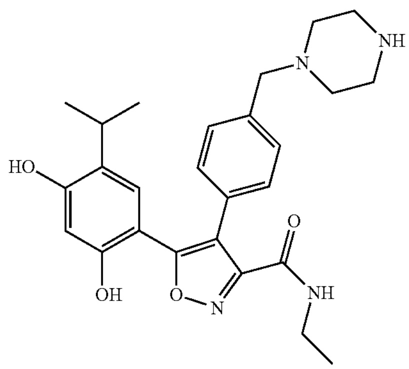 [SMILES: CCNC(=O)c1noc(-c2cc(C(C)C)c(O)cc2O)c1-c1ccc(CN2CCNCC2)cc1] | 465 | A |
| 78q | 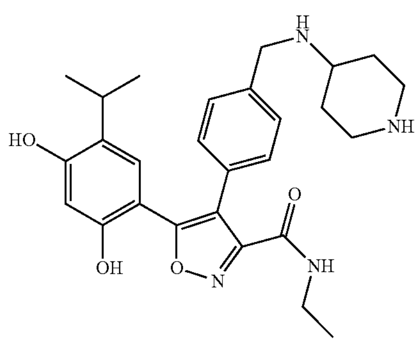 [SMILES: CCNC(=O)c1noc(-c2cc(C(C)C)c(O)cc2O)c1-c1ccc(CNC2CCNCC2)cc1] | 479 | A |
| 78r | 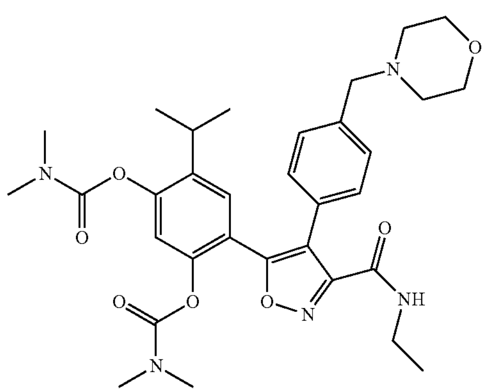 [SMILES: CCNC(=O)c1noc(-c2cc(C(C)C)c(OC(=O)N(C)C)cc2OC(=O)N(C)C)c1-c1ccc(CN2CCOCC2)cc1] | 608 | Pro-drug see Example 78v |

-continued

| Example | Structure | MH+ | Hsp90 IC50 |
|---|---|---|---|
| 78s | 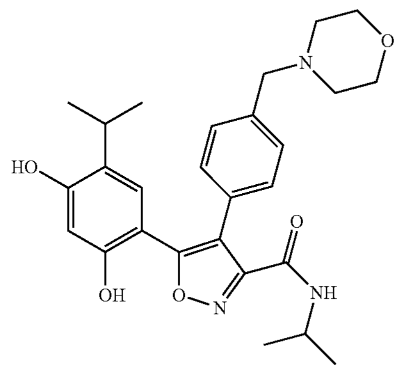 [SMILES: CC(C)NC(=O)c1noc(-c2cc(C(C)C)c(O)cc2O)c1-c1ccc(CN2CCOCC2)cc1] | 480 | A |
| 78t | 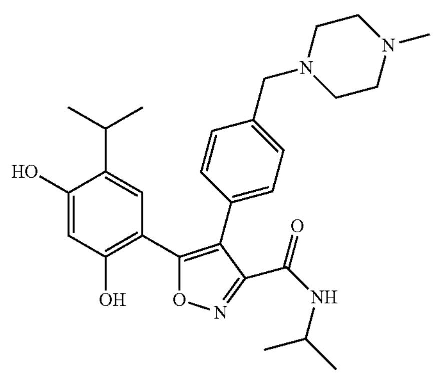 [SMILES: CC(C)NC(=O)c1noc(-c2cc(C(C)C)c(O)cc2O)c1-c1ccc(CN2CCN(C)CC2)cc1] | 493 | A |
| 78u | 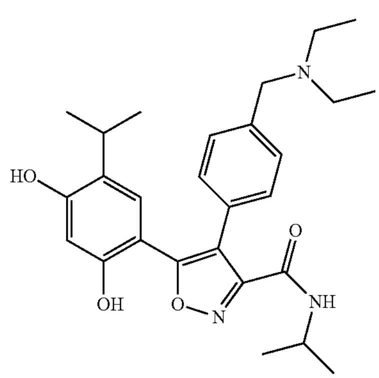 [SMILES: CCN(CC)Cc1ccc(-c2c(C(=O)NC(C)C)noc2-c2cc(C(C)C)c(O)cc2O)cc1] | 466 | A |
| 78w | 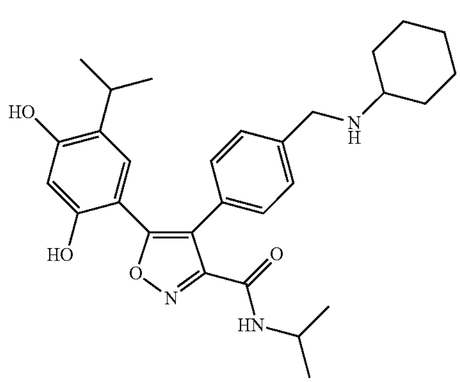 [SMILES: CC(C)NC(=O)c1noc(-c2cc(C(C)C)c(O)cc2O)c1-c1ccc(CNC2CCCCC2)cc1] | 492 | A |

| Example | Structure | MH+ | Hsp90 IC50 |
|---|---|---|---|
| 78y | 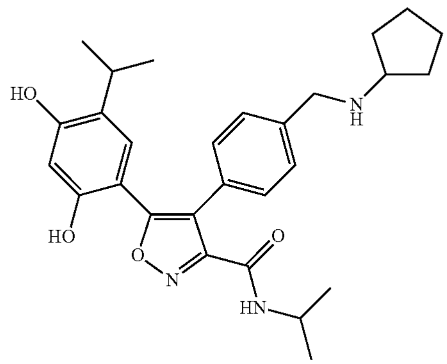 [SMILES: CC(C)NC(=O)c1noc(-c2cc(C(C)C)c(O)cc2O)c1-c1ccc(CNC2CCCC2)cc1] | 478 | A |
| 78z | 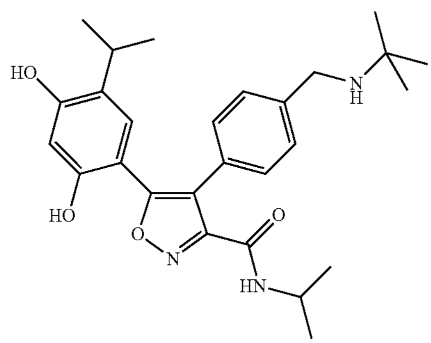 [SMILES: CC(C)NC(=O)c1noc(-c2cc(C(C)C)c(O)cc2O)c1-c1ccc(CNC(C)(C)C)cc1] | 466 | A |
| 78aa | 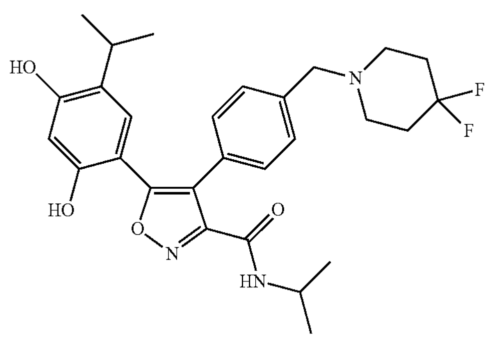 [SMILES: CC(C)NC(=O)c1noc(-c2cc(C(C)C)c(O)cc2O)c1-c1ccc(CN2CCC(F)(F)CC2)cc1] | 514 | A |
| 78ab | 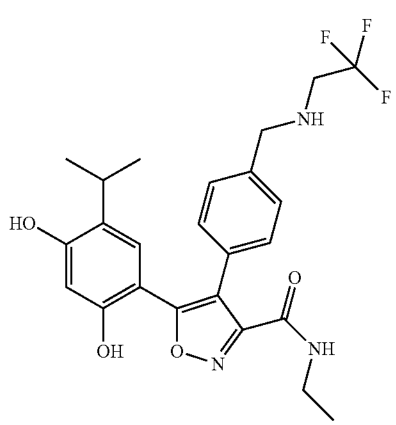 [SMILES: CCNC(=O)c1noc(-c2cc(C(C)C)c(O)cc2O)c1-c1ccc(CNCC(F)(F)F)cc1] | 478 | A |

-continued

| Example | Structure | MH+ | Hsp90 IC50 |
|---|---|---|---|
| 78ac | 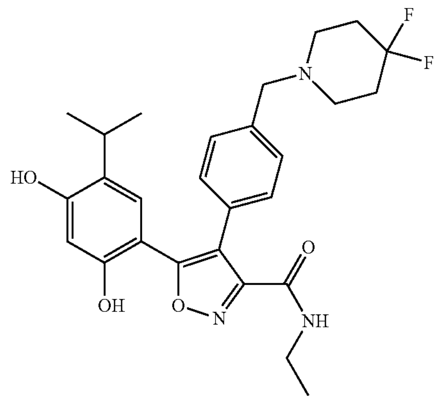 [SMILES: CCNC(=O)c1noc(-c2cc(C(C)C)c(O)cc2O)c1-c1ccc(CN2CCC(F)(F)CC2)cc1] | 500 | A |
| 78ad | 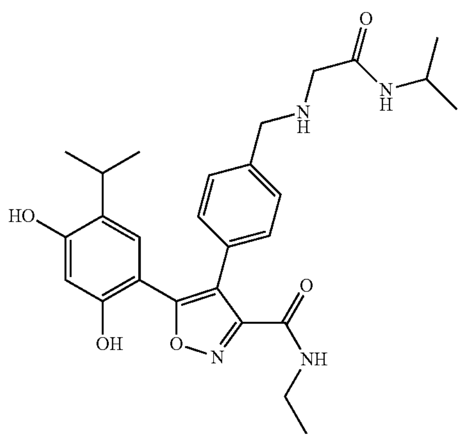 [SMILES: CCNC(=O)c1noc(-c2cc(C(C)C)c(O)cc2O)c1-c1ccc(CNCC(=O)NC(C)C)cc1] | 495 | A |
| 78ae | 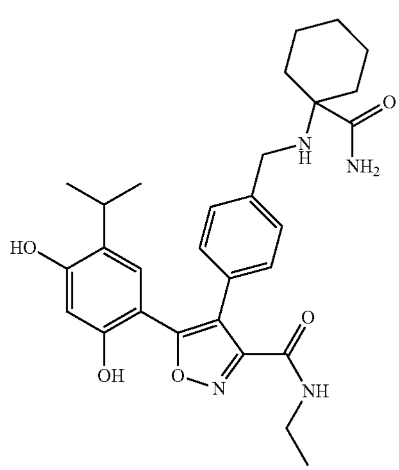 [SMILES: CCNC(=O)c1noc(-c2cc(C(C)C)c(O)cc2O)c1-c1ccc(CNC2(C(N)=O)CCCCC2)cc1] | 521 | A |

| Example | Structure | MH+ | Hsp90 IC50 |
|---|---|---|---|
| 78af | 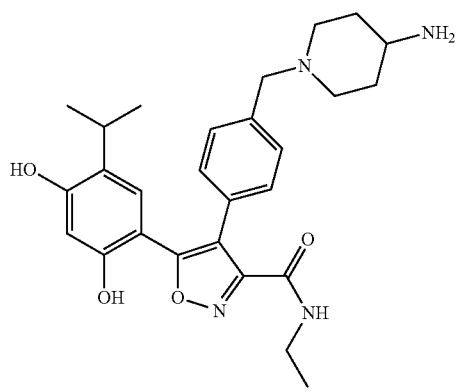 [SMILES: CCNC(=O)c1noc(-c2cc(C(C)C)c(O)cc2O)c1-c1ccc(CN2CCC(N)CC2)cc1] | 479 | A |
| 78ag | 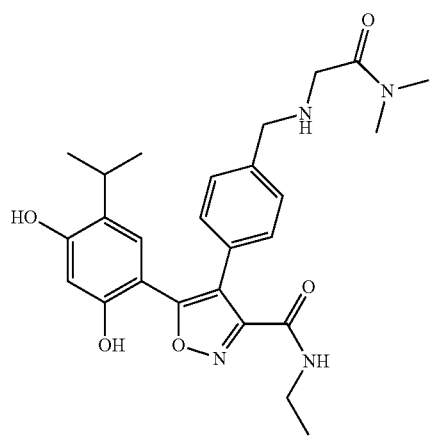 [SMILES: CCNC(=O)c1noc(-c2cc(C(C)C)c(O)cc2O)c1-c1ccc(CNCC(=O)N(C)C)cc1] | 481 | A |
| 78ah | 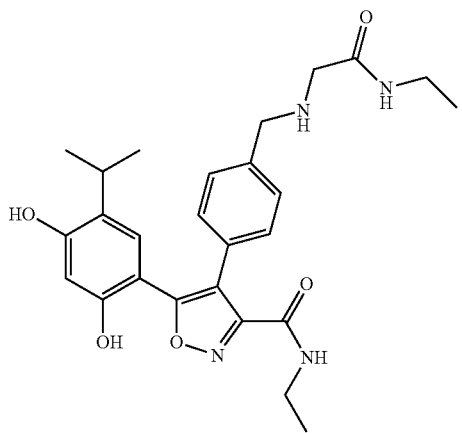 [SMILES: CCNC(=O)CNCc1ccc(-c2c(C(=O)NCC)noc2-c2cc(C(C)C)c(O)cc2O)cc1] | 481 | A |

| Example | Structure | MH+ | Hsp90 IC50 |
|---|---|---|---|
| 78ai | 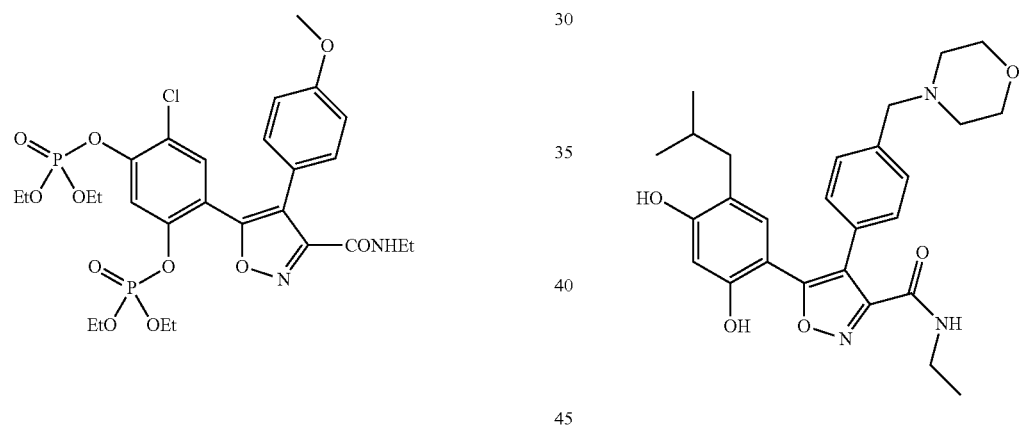 | 608 | Pro-drug see Example 78v |

Example 78v

Phosphoric acid 4-chloro-5-(diethoxy-phosphoryloxy)-2-[3-ethylcarbamoyl-4-(4-methoxy-phenyl)-isoxazol-5-yl]-phenyl ester diethyl ester To a solid mixture of 5-(5-Chloro-2,4-dihydroxy-phenyl)-4-(4-methoxy-phenyl)-isoxazole-3-carboxylic acid ethylamide (11 mg, $2.1 \times 10^{-2}$ mmol) and MgO (25 mg) in a small vial, 10 drops of diethyl chlorophosphate was added. The resulting mixture was heated and stirred at 70° C. for an hour, the progress of the reaction was monitored by TLC. When cooled, MeOH (1 ml) and DCM (1 ml) were added. After filtration, the solvents were evaporated and yellow oil was obtained. The di-phosphoryl ester was separated by preparative TLC, yielding 4 mg. $R_f$=0.35; $^1$H NMR δ=7.95 (1H, s, broad); 7.74 (1H, s); 7.55 (1H, s); 7.32 (2H, d, J=9.0 Hz); 6.90 (2H, d, J=9.0 Hz); 4.30 (8H, q); 3.80 (3H, s); 3.40 (2H, q); 1.35 (12H, t) and 1.25 (3H, t). LCMS: (M+1)$^+$=661.1 (RT=7.60 min.)

Example 79

Preparation of 5-(2,4-Dihydroxy-5-isobutyl-phenyl)-4-(4-morpholin-4-ylmethyl-phenyl)-isoxazole-3-carboxylic acid ethylamide Reaction Scheme

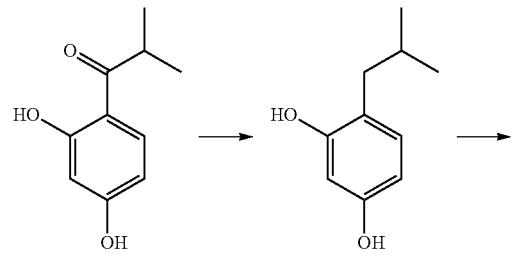

137
-continued

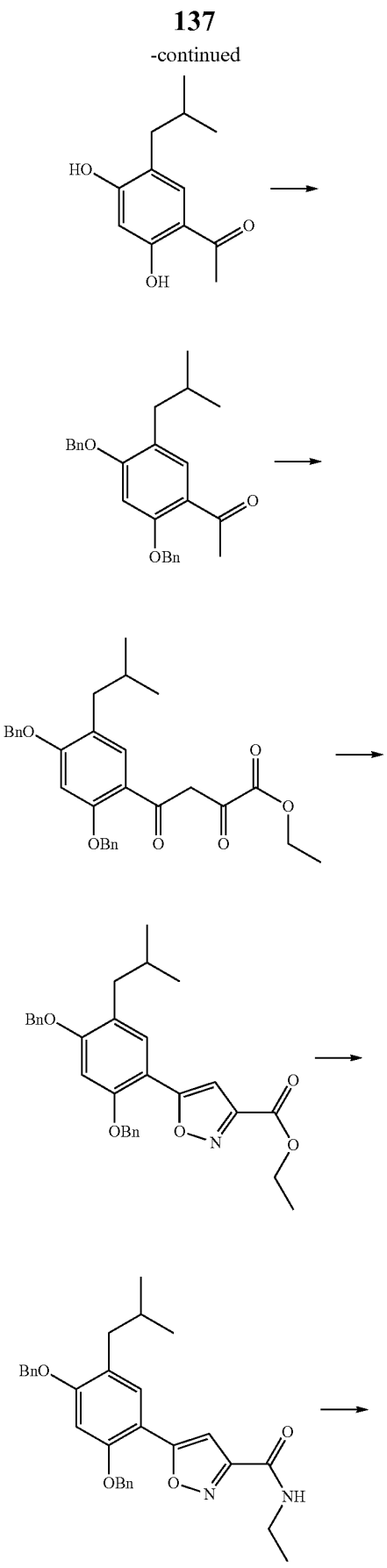

138
-continued

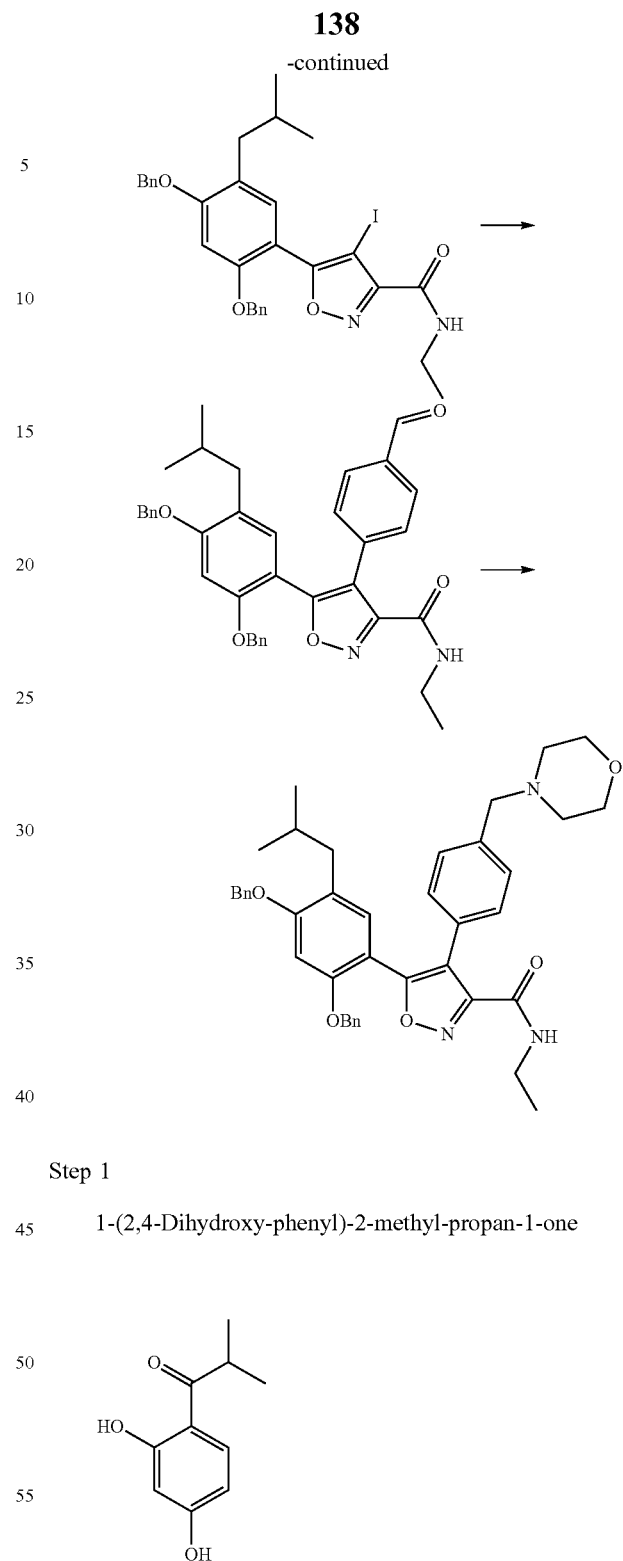

Step 1

1-(2,4-Dihydroxy-phenyl)-2-methyl-propan-1-one

Resorcinol (1 eq) was taken up in BF$_3$.OEt$_2$ (6 eq) and isobutyric acid (1 eq) added. The solution was heated for 1.5 hours at 90° C. than allowed to cool to room temperature. The solution was added drop wise to 10% NaOAc (aq) and allowed to stand for 4 hours, before being extracted in to EtOAc. The organic phases were combined and washed with sat. NaHCO$_3$ (aq), then dried over magnesium sulfate, filtered and concentrated in vacuo to give 1-(2,4-dihydroxyphenyl)-2-methyl-propan-1-one as a red oil which was used without additional purification LC retention time 2.279 min [M+H]+ 181.1

Step 2

4-Isobutyl-benzene-1,3-diol

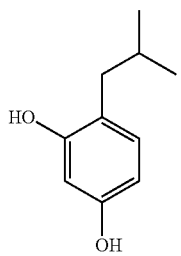

Ethyl chloroformate (3 eq) was added slowly to a cooled (0° C.) solution of 1-(2,4-dihydroxy-phenyl)-2-methyl-propan-1-one (1 eq) and triethylamine (3 eq) in THF. The mixture was warmed to ambient temperature and stirred for three hours before being filtered and the solids washed with cold THF. The combined filtrates were cooled to 0° C. and sodium borohydride (4 eq) in a volume of water equal to the THF filtrates added slowly. The mixture was warmed to ambient temperature, stirred for three hours and diluted with water. The mixture was twice extracted with diethyl ether, the combined extracts concentrated to dryness and re-suspended in 10% aqueous sodium hydroxide solution (4 eq). After refluxing for 90 minutes, the mixture was cooled, acidified with 5M aq HCl and twice extracted with diethyl ether. The organic extracts were dried over magnesium sulphate, filtered and concentrated to dryness to give 4-isobutyl-benzene-1,3-diol as a cloudy oil, which was used without further purification.

NMR consistent with structure.

Example 3

1-(2,4-Dihydroxy-5-isobutyl-phenyl)-ethanone

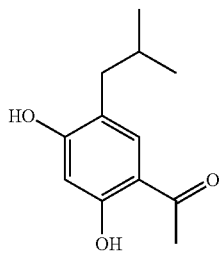

4-Isobutyl-benzene-1,3-diol (1 eq) was taken up in BF$_3$.OEt$_2$ (6 eq) and acetic acid (2 eq) was added. The solution was heated for 16 hours at 90° C. than allowed to cool to room temperature. The solution was added drop wise to 10% NaOAc (aq) and allowed to stand for 4 hours, before being extracted twice with diethyl ether. The organic phases were combined and washed with sat. NaHCO$_3$ (aq), then dried over magnesium sulfate, filtered and concentrated in vacuo to give 1-(2,4-dihydroxy-5-isobutyl-phenyl)-ethanone, which was used without additional purification.

NMR consistent with structure.

Step 4

1-(2,4-Bis-benzyloxy-5-isobutyl-phenyl)-ethanone

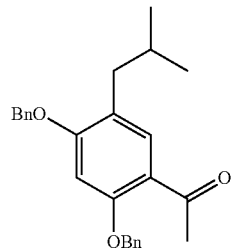

1-(2,4-Dihydroxy-5-isobutyl-phenyl)-ethanone (1 eq) was dissolved in DMF and potassium carbonate (4.4 eq) then benzyl bromide (4.4 eq) was added. The suspension was heated, with stirring to 150° C., under nitrogen, for 16 hrs. The solution was cooled to room temperature, filtered and concentrated to dryness. This solid was purified column chromatography (silica, hexanes:ethyl acetate 4:1) then re-crystallised from ethyl acetate:hexanes to give 1-(2,4-Bis-benzyloxy-5-isobutyl-phenyl)-ethanone as colourless crystals.

LC retention time 3.030 min [M+H]+ 389.3

Step 5

4-(2,4-Bis-benzyloxy-5-isobutyl-phenyl)-2,4-dioxo-butyric acid ethyl ester

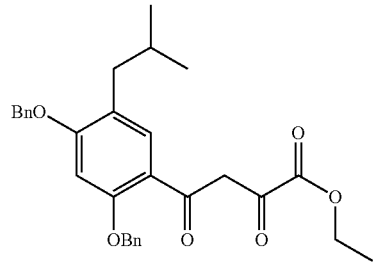 [SMILES: CCOC(=O)C(=O)CC(=O)c1cc(CC(C)C)c(OCc2ccccc2)cc1OCc1ccccc1]

Sodium (3 eq) was added to ethanol under nitrogen at room temperature and stirred until complete dissolution occurred. 1-(2,4-Bis-benzyloxy-5-isobutyl-phenyl)-ethanone (1 eq) was added, followed by diethyl oxalate (1.5 eq) and the reaction mixture heated to reflux for 4 hours. The mixture was allowed to cool to room temperature and acidified with 2M HCl (aq) to give a yellow precipitate of 4-(2,4-Bis-benzyloxy-5-isobutyl-phenyl)-2,4-dioxo-butyric acid ethyl ester, which was obtained by filtration.

LC retention time 3.254 min [M+H]+ 489.3

Step 6

5-(2,4-Bis-benzyloxy-5-isobutyl-phenyl)-isoxazole-3-carboxylic acid ethyl ester

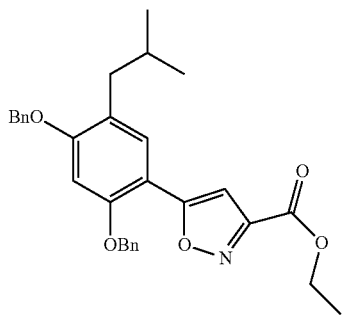 [SMILES: CCOC(=O)c1cc(-c2cc(CC(C)C)c(OCc3ccccc3)cc2OCc2ccccc2)on1]

4-(2,4-Bis-benzyloxy-5-isobutyl-phenyl)-2,4-dioxo-butyric acid ethyl ester (1 eq) was dissolved in ethanol with stirring. Hydroxylamine hydrochloride (1.2 eq) was added and the solution was heated to reflux for 2 hours. The reaction mixture was cooled to room temperature, to give a precipitate. This precipitate was obtained by filtration to give 5-(2,4-Bis-benzyloxy-5-isobutyl-phenyl)-isoxazole-3-carboxylic acid ethyl ester as a white solid.

LC retention time 3.261 min [M+H]$^+$ 486.3

Step 7

5-(2,4-Bis-benzyloxy-5-isobutyl-phenyl)-isoxazole-3-carboxylic acid ethylamide

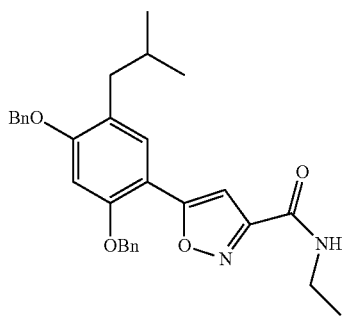 [SMILES: CCNC(=O)c1cc(-c2cc(CC(C)C)c(OCc3ccccc3)cc2OCc2ccccc2)on1]

5-(2,4-Bis-benzyloxy-5-isobutyl-phenyl)-isoxazole-3-carboxylic acid ethyl ester was dissolved in 2-Methylamine in methanol (10 eq) and heated in the Smith Synthesiser microwave at 120° C. for 600 seconds. The solution was concentrated in vacuo to give 5-(2,4-bis-benzyloxy-5-isobutyl-phenyl)-isoxazole-3-carboxylic acid ethylamide as a white solid which was used without additional purification.

LC retention time 3.112 min [M+H]$^+$ 485.3

Step 8

5-(2,4-Bis-benzyloxy-5-isobutyl-phenyl)-4-iodo-isoxazole-3-carboxylic acid ethylamide

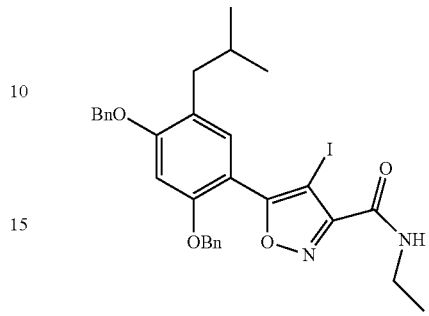

5-(2,4-Bis-benzyloxy-5-isobutyl-phenyl)-isoxazole-3-carboxylic acid ethylamide (1 eq) and N-iodosuccinimide (2.0 eq), were dissolved in acetonitrile, ceric ammonium nitrate (0.1 eq) added and the solution was stirred at room temperature overnight. The reaction mixture was concentrated in vacuo and the resulting gum was partitioned between ethyl acetate and brine. The organic phase was dried over magnesium sulfate, filtered and concentrated in vacuo. The residue was purified by column chromatography, eluting with 4:1 hexane:ethyl acetate, to give 5-(2,4-bis-benzyloxy-5-isobutyl-phenyl)-4-iodo-isoxazole-3-carboxylic acid ethylamide as an oil.

LC retention time 3.089 min [M+H]$^+$ 611.2

Step 9

5-(2,4-Bis-benzyloxy-5-isobutyl-phenyl)-4-(4-formyl-phenyl)-isoxazole-3-carboxylic acid ethylamide

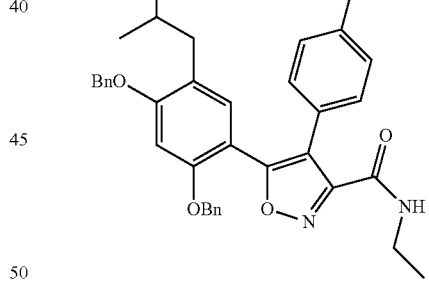

5-(2,4-Bis-benzyloxy-5-isobutyl-phenyl)-4-iodo-isoxazole-3-carboxylic acid ethylamide (1 eq) was dissolved in DMF and 1M Na$_2$CO$_3$ (aq) (3 eq) was added, followed by 4-formylphenylboronic acid (2 eq) and catalytic PdCl$_2$(PPh$_3$)$_2$. Nitrogen was bubbled through the solution for ten minutes at ambient temperature, after which time, the temperature was elevated to 80° C. under a nitrogen atmosphere, for 2 hours. The reaction mixture was allowed to cool to room temperature and the reaction mixture was diluted with ethyl acetate. This solution was washed with brine, then dried over magnesium sulfate, filtered and concentrated in vacuo to give an oil which was purified by column chromatography, eluting with 10% EtOAc in hexane, to give 5-(2,4-bis-benzyloxy-5-isobutyl-phenyl)-4-(4-formyl-phenyl)-isoxazole-3-carboxylic acid ethylamide as a white solid.

LC retention time 5.57 min [M+H]$^+$ 589.1 method B

Step 10

5-(2,4-Bis-benzyloxy-5-isobutyl-phenyl)-4-(4-morpholin-4-ylmethyl-phenyl)-isoxazole-3-carboxylic acid ethylamide

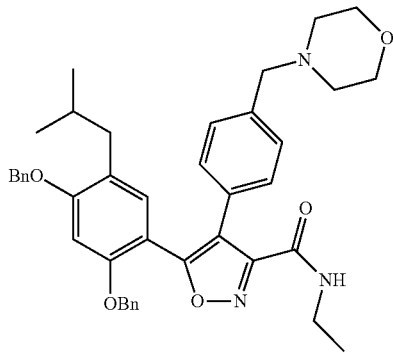 [SMILES: CCNC(=O)c1noc(-c2cc(CC(C)C)c(OCc3ccccc3)cc2OCc2ccccc2)c1-c1ccc(CN2CCOCC2)cc1]

5-(2,4-Bis-benzyloxy-5-isobutyl-phenyl)-4-(4-formyl-phenyl)-isoxazole-3-carboxylic acid ethylamide (1 eq) was dissolved in methanol and powdered 3 Å sieves were added. Morpholine (2 eq) was added, followed by acetic acid (5 eq). After stirring for 30 minutes, sodium cyanoborohydride (2 eq) was added portionwise and the suspension was stirred under nitrogen at ambient temperature for 16 hours. The reaction mixture was filtered through celite and concentrated to dryness. Column chromatography, eluting with 5% MeOH in DCM gave 5-(2,4-bis-benzyloxy-5-isobutyl-phenyl)-4-(4-morpholin-4-ylmethyl-phenyl)-isoxazole-3-carboxylic acid ethylamide as a colourless oil.

LC retention time 4.53 min [M+H]$^+$ 660.2 method B

Step 11

5-(2,4-Dihydroxy-5-isobutyl-phenyl)-4-(4-morpholin-4-ylmethyl-phenyl)-isoxazole-3-carboxylic acid ethylamide

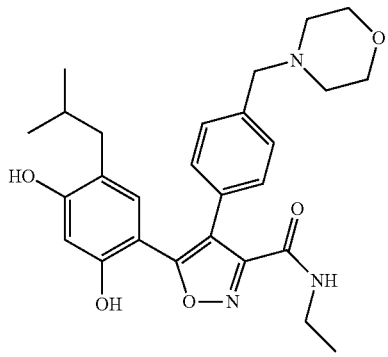 [SMILES: CCNC(=O)c1noc(-c2cc(CC(C)C)c(O)cc2O)c1-c1ccc(CN2CCOCC2)cc1]

5-(2,4-Bis-benzyloxy-5-isobutyl-phenyl)-4-(4-morpholin-4-ylmethyl-phenyl)-isoxazole-3-carboxylic acid ethylamide (1 eq) was dissolved in an. DCM and under a nitrogen atmosphere, was cooled to 0° C. 1M BCl$_3$ in DCM (9 eq) was added dropwise and the solution was stirred for 30 minutes. Methanol (2 ml) was added and the reaction mixture was concentrated in vacuo. Purification of the sample by preparative LC/MS gave 5-(2,4-dihydroxy-5-isobutyl-phenyl)-4-(4-morpholin-4-ylmethyl-phenyl)-isoxazole-3-carboxylic acid ethylamide as a white solid.

LC retention time 1.902 min [M+H]$^+$ 480.3

This compound had activity 'A' in the Hsp900 fluorescence polarization assay.

In a similar manner to the preparation of the compound of example 79, example 80 was prepared. Purification of the sample by preparative LC/MS gave the compound as a white solid

| Example | Structure | MH+ | Hsp90 IC50 |
|---|---|---|---|
| 80 | 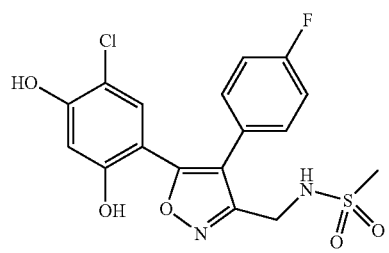 | 480 | A |

Example 81

N-[5-(5-Chloro-2,4-dihydroxy-phenyl)-4-(4-fluoro-phenyl)-isoxazol-3-ylmethyl]-methanesulfonamide

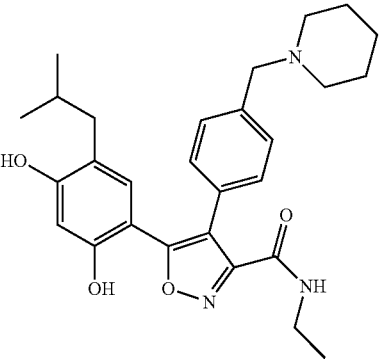 [SMILES: CCNC(=O)c1noc(-c2cc(CC(C)C)c(O)cc2O)c1-c1ccc(CN2CCCCC2)cc1]

Example 82

N-[5-(5-Chloro-2,4-dihydroxy-phenyl)-4-(4-fluoro-phenyl)-isoxazol-3-ylmethyl]-acetamide 5-(2,4-Bis-benzyloxy-5-chloro-phenyl)-4-(4-fluoro-phenyl)-isoxazole-3-carboxylic acid amide

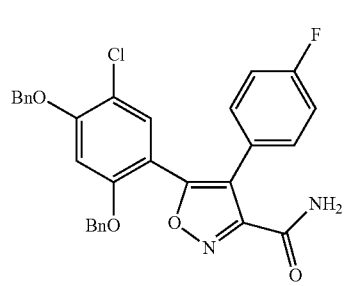 [SMILES: NC(=O)c1noc(-c2cc(Cl)c(OCc3ccccc3)cc2OCc2ccccc2)c1-c1ccc(F)cc1]

5-(2,4-Bis-benzyloxy-5-chloro-phenyl)-4-iodo-isoxazole-3-carboxylic acid amide (0.45 g, 0.80 mmol) was cross coupled to 4-fluorophenylboronic acid (0.17 g, 1.5 equiv.) using the standard conditions described above. The crude product, an orange solid (0.40 g), was taken on to the next step without further purification.

LCMS (LCQ) $t_R$=8.70, MS m/z 529.1 $[M+H]^+$

C-[5-(2,4-Bis-benzyloxy-5-chloro-phenyl)-4-(4-fluoro-phenyl)-isoxazol-3-yl]-methylamine

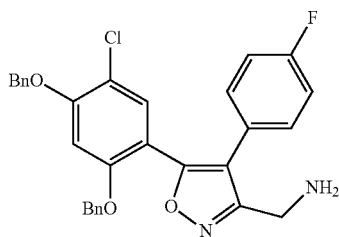 [SMILES: NCc1noc(-c2cc(Cl)c(OCc3ccccc3)cc2OCc2ccccc2)c1-c1ccc(F)cc1]

To a solution of 5-(2,4-Bis-benzyloxy-5-chloro-phenyl)-4-(4-fluoro-phenyl)-isoxazole-3-carboxylic acid amide (0.40 g, 0.76 mmol) in anhydrous THF (20 ml) under argon was added 1M Borane-THF complex (1 ml) and the solution refluxed overnight. After cooling the reaction was quenched with methanol (10 ml) and the product purified using a Isolute® SPE Flash SCX-2 5 g to provide 0.30 g (77% yield) as a powder.

LCMS (LCQ) $t_R$=7.54, MS m/z 515.2 $[M+H]^+$

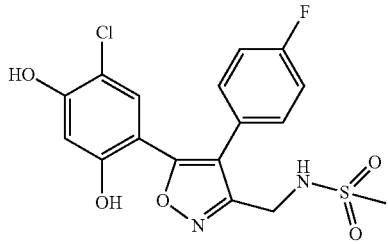 [SMILES: CS(=O)(=O)NCc1noc(-c2cc(Cl)c(O)cc2O)c1-c1ccc(F)cc1]

N-[5-(5-Chloro-2,4-dihydroxy-phenyl)-4-(4-fluoro-phenyl)-isoxazol-3-ylmethyl]-methanesulfonamide C-[5-(2,4-Bis-benzyloxy-5-chloro-phenyl)-4-(4-fluoro-phenyl)-isoxazol-3-yl]-methylamine (100 mg, 0.19 mmol) was dissolved in DCM (3 ml) before the addition of methane sulfonyl chloride (17 µl, 1.1 equiv.) and triethylamine (30 µl, 1.1 equiv.). The solution was stirred at room temperature overnight before evaporated to dryness in vacuo leaving a the crude benzyl protected product as a blue coloured residue (90 mg). This was deprotected using the standard procedure with boron trichloride described above and purified by preparative TLC (10% ethanol in DCM) and soxhlet extraction of the silica by ether gave the pure compound as a near colourless solid (8 mg, 10% yield).

LCMS (LCQ) $t_R$=6.65, MS m/z 411.2 [M−H]−

$\delta H$ (d4-MeOH), 7.19 (2H, m, Ar—H), 7.04 (1H, s, Ar—H), 7.03 (2H, m, Ar—H), 6.34 (1H, s, Ar—H), 4.27 (2H, s, $CH_2NH$), 2.81 (3H, s, SO2CH3).

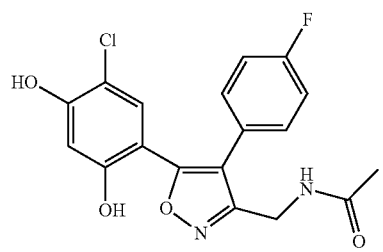 [SMILES: CC(=O)NCc1noc(-c2cc(Cl)c(O)cc2O)c1-c1ccc(F)cc1]

N-[5-(5-Chloro-2,4-dihydroxy-phenyl)-4-(4-fluoro-phenyl)-isoxazol-3-ylmethyl]-acetamide To a solution of C-[5-(2,4-Bis-benzyloxy-5-chloro-phenyl)-4-(4-fluoro-phenyl)-isoxazol-3-yl]-methylamine (100 mg, 0.19 mmol) in DCM was added acetic anhydride (130 µl, 7.0 equiv.) and triethylamine (81 µl, 3.0 equiv.). The solution was stirred at room temperature until the amine was consumed. The solvent was removed in vacuo to leave the yellow tinged oily crude benzyl protected product. This was deprotected using the standard procedure with boron trichloride described above and purified by preparative TLC and soxhlet extraction of the silica by ether gave the pure compound as a colourless solid (10 mg, 14% yield).

LCMS (LCQ) $t_R$=6.57, MS m/z 377.1 $[M+H]^+$ $\delta_H$ (d$^4$-MeOH), 7.17 (2H, m, Ar—H), 7.01 (1H, s, Ar—H), 6.98 (2H, m, Ar—H), 6.32 (1H, s, Ar—H), 4.37 (2H, s, $CH_2NH$), 1.77 (3H, s, $COCH_3$).

Examples 83, 84 and 85

5-(5-Ethyl-4-hydroxy-2-methoxy-phenyl)-4-(4-morpholin-4-ylmethyl-phenyl)-isoxazole-3-carboxylic acid ethylamide (83); 5-(5-Ethyl-2-hydroxy-4-methoxy-phenyl)-4-(4-morpholin-4-ylmethyl-phenyl)-isoxazole-3-carboxylic acid ethylamide (84); 5-(5-Ethyl-2,4-dimethoxy-phenyl)-4-(4-morpholin-4-ylmethyl-phenyl)-isoxazole-3-carboxylic acid ethylamide (85)

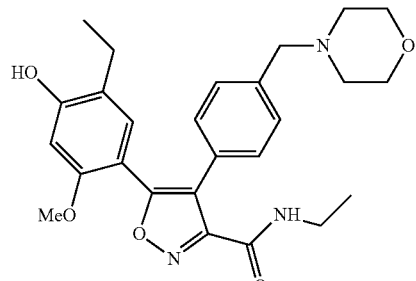

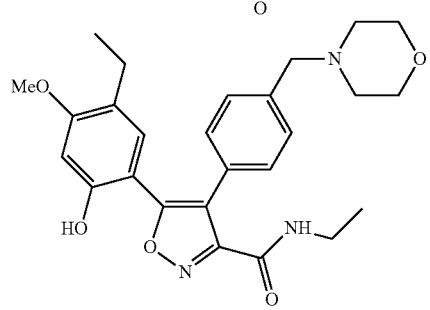

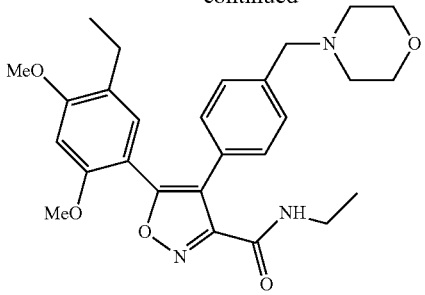

To an argon charged flask containing 5-(5-Ethyl-2,4-dihydroxy-phenyl)-4-(4-morpholin-4-ylmethyl-phenyl)-isoxazole-3-carboxylic acid ethylamide (25 mg, 0.055 mmol) and N,N-(Diisopropyl)aminomethylpolystyrene [PS-DIEA](35 mg, 3.83 mmol/g, 2.4 equiv.) was added anhydrous DCM (2.3 ml) and anhydrous methanol (0.25 ml). During gentle stirring, 2M (Trimethylsilyl)diazomethane in hexanes (28 μl, 1.0 equiv.) was added and the solution stirred overnight at room temperature. Argon was bubbled through the solution for 10 mins, the resin filtered off, and the volitiles removed in vacuo. The crude residue was purified by semi-preparative HPLC to yield 5-(5-Ethyl-4-hydroxy-2-methoxy-phenyl)-4-(4-morpholin-4-ylmethyl-phenyl)-isoxazole-3-carboxylic acid ethylamide (83) (5.52 mg, 21%), 5-(5-Ethyl-2-hydroxy-4-methoxy-phenyl)-4-(4-morpholin-4-ylmethyl-phenyl)-isoxazole-3-carboxylic acid ethylamide (84) (1.14 mg, 4%), 5-(5-Ethyl-2,4-dimethoxy-phenyl)-4-(4-morpholin-4-ylmethyl-phenyl)-isoxazole-3-carboxylic acid ethylamide (1.46 mg, 5%) and the non-methylated starting material.

83: LCMS (LCT) $t_R$=4.95, MS m/z 466.4 [M+H]$^+$
84: LCMS (LCT) $t_R$=5.14, MS m/z 466.4 [M+H]$^+$
(85): LCMS (LCT) $t_R$=5.45, MS m/z 480.4 [M+H]$^+$
NMR data confirmed the assignments.

Example 86

Ethyl 5-(5-chloro-2-hydroxy-phenyl)-4-(4-morpholin-4-ylmethyl-phenyl)-isoxazole-3-carboxamide

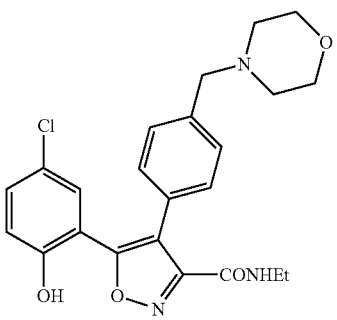

Step 1

Methyl 2-benzoyloxy-5-chloro-benzoate

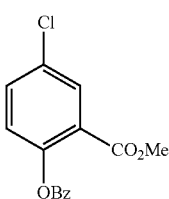

A mixture of methyl 5-chloro-2-hydroxy-benzoate (2.5 g, 13.4 mmol), $K_2CO_3$ (3.7 g, 26.8 mmol) and benzyl bromide (2.98 g, 17.4 mmol) in acetone (30 ml) was refluxed for 12 hours. After cooling, acetone was evaporated. EtOAc (100 ml) was added and filtered. The organic layer was then washed with 1M HCl (1×80 ml), brine (2×80 ml) and dried with $Na_2SO_4$. After filtration and evaporation of the solvent, yellow semi-solids were obtained (3.2 g). $^1$H NMR (d$_6$-acetone) δ=7.73 (1H, d); 7.60-7.30 (1H+5H, m); 7.28 (1H, d); 5.30 (2H, s) and 3.90 (3H, s).

Step 2

1-(2-Benzyloxy-5-chloro-phenyl)-2-(triphenyl-λ$^5$-phosphanylidene)-ethanone

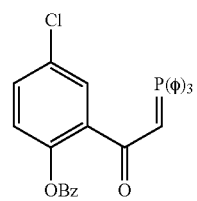

To a stirred suspension of triphenylphosphonium bromide (2.14 g, 6.0 mmol) in dried THF (30 ml) at room temperature was added 1.6M n-BuLi in hexane (5.25 ml, 8.39 mmol). The orange suspension was stirred for 3 hours. Next, a solution of methyl 2-benzoyloxy-5-chloro-benzoate (0.83 g, 3.0 mmol) in THF (8 ml) was slowly added. The resulting mixture was stirred at 60° C. for 2 hours and filtered after cooled. DCM (100 ml) was added to the filtrate and the combined organic layers were washed with brine (2×80 ml). After filtration and evaporation of the solvent, yellow oil was obtained (2.0 g). They were then purified by chromatography, eluted with EtOAc:hexane/1:1, yielded 0.97 g solids. R$_f$=0.43. $^1$H NMR (d$_6$-acetone) δ=7.80-7.52 (20H, m); 7.40-7.20 (1H+1H+1H, m); 5.25 (2H, s); 4.72 (1H, s, trans-H) and 4.62 (1H, s, cis-H). LCMS: (M+1)$^+$=521.2 (RT=5.94 min.)

Step 3

Ethyl 4-(2-benzyloxy-5-chloro-phenyl)-2,4-dioxo-3-(triphenyl-λ$^5$ phosphanylidene)-butyrate

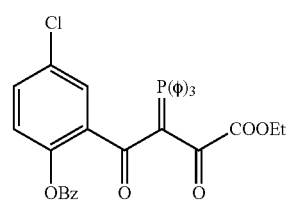

To a solution of 1-(2-Benzyloxy-5-chloro-phenyl)-2-(triphenyl-λ$^5$-phosphanylidene)-ethanone (0.49 g, 0.94 mmol), NEt$_3$ (96 mg, 0.94 mmol) and DMAP (12 mg, 0.09 mmol) in dry toluene (20 ml) at room temperature, ethyl chlorooxoacetate (0.38 g, 2.78 mmol) in toluene (5 ml) was added. The mixture was stirred for 2 hours and poured into water (50 ml). The organic layer was separated and the aq. layer was extracted with EtOAc (2×40 ml). The combined organic layers were then washed with sat. NaHCO$_3$ solution (2×40 ml), sat. citric acid (1×40 ml), brine (1×40 ml) and dried. Crude oil (0.36 g) was purified by chromatography, eluted with EtOAc. R$_f$=0.88. $^1$H NMR (d$_6$-acetone) δ=7.75-7.40 (15H, m); 7.30 (1H, dd); 7.15 (1H, d); 7.05 (1H, d); 5.10

(2H, s); 3.60 (2H, q) and 1.10 (3H, s). LCMS: (M+1)⁺=621.2 (RT=6.49 min.)
Step 4

Ethyl 3-(2-benzoyloxy-5-chloro-benzoyl)-3-bromo-3H-azirine-2-carboxylate

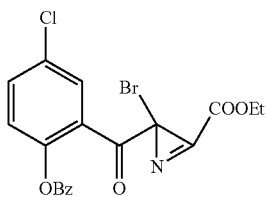

To a solution of ethyl 4-(2-benzyloxy-5-chloro-phenyl)-2,4-dioxo-3-(triphenyl-$\lambda^5$-phosphanylidene)-butyrate (0.143 g, 0.23 mmol) in DCM (8 ml) at room temperature, a mixture of TMSN₃ (40 mg, 0.35 mmol) and NBS (62 mg, 0.35 mmol) in DCM (6 ml) was added. The resulting solution was stirred for 2 hours. After evaporation of the solvent, the crude product was purified by preparative TLC. Yellow solids (38 mg) were obtained. R$_f$=0.73 (EtOAc: hexane 1:2). ¹H NMR (d₆-acetone) δ=7.80 (1H, d); 7.60 (1H, dd); 7.40 (5H, m); 7.30 (1H, d); 5.20 (2H, s); 4.10 (2H, q) and 1.00 (3H, t). LCMS: (M+1)⁺=438.0 (RT=7.32 min.)
Step 5

Ethyl 5-(2-benzoyloxy-5-chloro-phenyl)-4-bromo-isoxazole-3-carboxylate

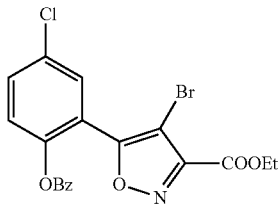

Ethyl 3-(2-benzoyloxy-5-chloro-benzoyl)-3-bromo-3H-azirine-2-carboxylate (55 mg, 0.12 mmol) was heated at reflux in dry toluene for 2 hours. After evaporation of the solvent, crude solids (34 mg) were obtained and purified by preparative TLC (EtOAc:hexane/1:2). R$_f$=0.73 (fluorescent). ¹H NMR (d₆-acetone) δ=7.60 (1H, d); 7.50 (1H, dd); 7.40 (1H, d); 7.30 (5H, m); 5.25 (2H, s); 4.42 (2H, q) and 1.40 (3H, t). LCMS: (M+1)⁺=438.0 (RT=7.09 min.)
Step 6

Ethyl 5-(2-benzyloxy-5-chloro-phenyl)-4-bromo-isoxazole-3-carboxamide

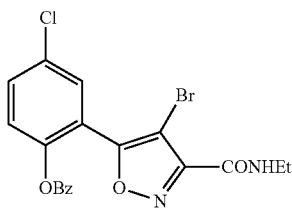

To a solution of ethyl 5-(2-benzoyloxy-5-chloro-phenyl)-4-bromo-isoxazole-3-carboxylate (30 mg, 6.8×10⁻² mmol) in EtOH (1 ml), ethylamine (70% in water, 1 ml) was added. The solution was heated at 100° C. in a CEM® microwave reactor (200 W) for one hour. After that, the solvent was evaporated and the compound purified by preparative TLC to yield solids (20 mg). R$_f$=0.39 (EtOAc:hexane/1:4). ¹H NMR (d₆-acetone) δ=8.10 (1H, s, broad); 7.50 (1H, d); 7.45-7.35 (1H+1H, m); 7.25 (5H, m); 5.20 (2H, s); 3.40 (2H, q) and 1.20 (3H, t). LCMS: (M+1)⁺=437.1 (RT=6.57 min.)
Step 7

Ethyl 5-(2-benzyloxy-5-chloro-phenyl)-4-(4-morpholin-4-ylmethyl-phenyl)-isoxazole-3-carboxamide

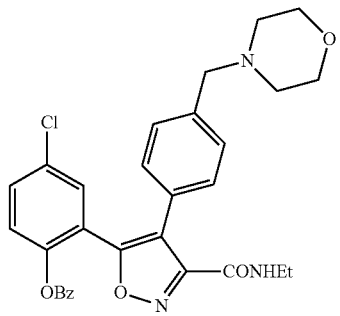

A mixture of ethyl 5-(2-enzyloxy-5-chloro-phen-4-bromo-isoxazole-3-carboxamide (30 mg, 5.6×10⁻² mmol), Pd(Ph₃P)₄ (4 mg, 3.5×10⁻² mmol), 4[4-(4,4,5,5-Tetramethyl-[1,3,2]dioxaborolan-2-yl)-benzyl]morpholine (63 mg, 0.2 mmol) and 1M NaHCO₃ solution (0.2 ml) in DME (1 ml) was stirred at 80° C. under Argon gas for 16 hours. After cooling, the solution was diluted with water (8 ml) and extracted with EtOAc (2×20 ml). The combined organic layers were washed with brine (1×20 ml) and dried. After filtration and evaporation of the solvents, the crude product was purified by preparative TLC, yielded 30 mg solids. R$_f$=0.44 (EtOAc). ¹H NMR (d₆-acetone) δ=8.25 (1H, s, broad); 7.60 (1H, d); 7.55 (1H, dd); 7.45 (1H, d); 7.30-6.90 (9H, m); 5.00 (2H, s); 3.55 (4H, m); 3.45 (2H+2H, s+q); 2.30 (4H, m) and 1.20 (3H, t). LCMS: (M+1)⁺=532.2 (RT=4.39 min.)
Step 8

Ethyl 5-(5-chloro-2-hydroxy-phenyl)-4-(4-morpholin-4-ylmethyl-phenyl)-isoxazole-3-carboxamide

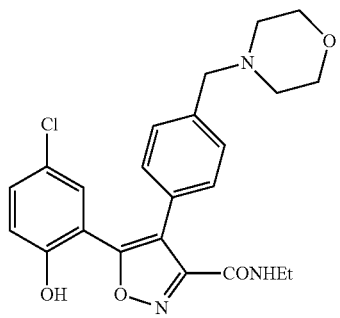

To a solution of ethyl 5-(2-benzyloxy-5-chloro-phenyl)-4-(4-morpholin-4-ylmethyl-phenyl)-isoxazole-3-carboxamide (25 mg, 4.7×10⁻² mmol) in DCM (5 ml) at 0° C., 1M BCl₃ in DCM (0.15 ml) was added. The resulting cloudy yellow solution was then stirred at 0° C. for 15 minutes and room temperature 3 to 4 hours until it became clear. After that, the solution was quenched by MeOH (1 ml). Sat. NaHCO₃ (1 ml) was then added and extracted with EtOAc (2×2 ml) and dried. After the solvent was filtered and evaporated, the crude oil was purified by preparative TLC (EtOAc:MeOH/50:1), yielded 12 mg solids. ¹H NMR (d₄-MeOD) δ=7.60 (2H, d); 7.50-7.30 (1H+1H+1H, m); 7.00 (2H, d); 3.70 (4H, m); 3.60 (2H, s); 3.50 (2H, q); 2.60 (4H, m) and 1.25 (3H, t). LCMS: (M+1)⁺=442.2 (RT=3.54 min.)

The 4-hydroxy-isomer was prepared in a similar way as its 2-hydroxy counterpart as follows:

Example 87

Ethyl 5-(3-chloro-4-hydroxy-phenyl)-4-(4-morpholin-4-ylmethyl-phenyl)-isoxazole-3-carboxamide

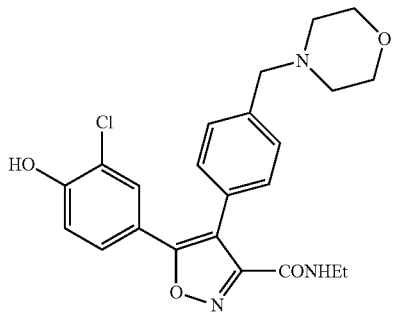

Step 1

Methyl 4-benzoyloxy-3-chloro-benzoate

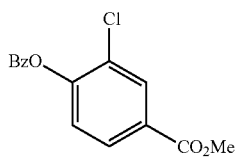

Methyl 3-chloro-4-hydroxy-benzoate (1.0 g, 5.36 mmol) gave a crude solid (1.57 g). ¹H NMR (d₆-acetone) δ=8.00 (1H, d); 7.95 (1H, dd); 7.60-7.40 (5H, m); 7.35 (1H, d); 5.40 (2H, s) and 3.90 (3H, s).
Step 2

1-(4-Benzyloxy-3-chloro-phenyl)-2-(triphenyl-λ⁵-phosphanylidene)-ethanone

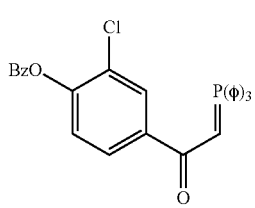

Methyl 4-benzoyloxy-3-chloro-benzoate (1.5 g, 5.40 mmol) gave a crude solid (2.5 g). R_f=0.31 (EtOAc:hexane/1:1). ¹H NMR (d₆-acetone) δ=8.05 (1H, d); 7.90 (1H, dd); 7.85-7.35 (20H, m); 7.20 (1H, d); 5.30 (2H, s); 4.60 (1H, s, trans-H) and 4.50 (1H, s, cis-H). LCMS: (M+1)⁺=521.2 (RT=5.29 min.)
Step 3

Ethyl 4-(4-benzyloxy-3-chloro-phenyl)-2,4-dioxo-3-(triphenyl-λ⁵ phosphanylidene)-butyrate

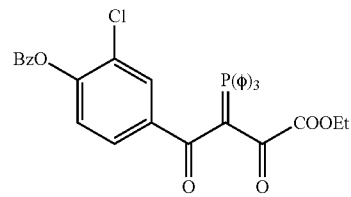

1-(4-Benzyloxy-3-chloro-phenyl)-2-(triphenyl-λ⁵-phosphanylidene)-ethanone (1.84 g, 3.53 mmol) gave a crude solid (1.43 g). ¹H NMR (d₆-acetone) δ=8.00-7.35 (22H, m); 7.20 (1H, d); 5.35 (2H, s); 3.55 (2H, q) and 1.14 (3H, s). LCMS: (M+1)⁺=621.2 (RT=7.29 min.)
Step 4

Ethyl 3-(4-benzoyloxy-3-chloro-benzoyl)-3-bromo-3H-azirine-2-carboxylate

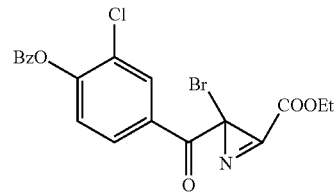

Ethyl 4-(4-benzyloxy-3-chloro-phenyl)-2,4-dioxo-3-(triphenyl-λ⁵ phosphanylidene)-butyrate (0.74 g, 1.19 mmol) gave a solid (0.168 g) after column and preparative TLC purification. R_f=0.24 (EtOAc:hexane/1:6). ¹H NMR (d₆-acetone) δ=8.00 (1H, d); 7.90 (1H, dd); 7.50 (1H, d); 7.40 (5H, m); 5.40 (2H, s); 4.05 (2H, q) and 0.95 (3H, t). LCMS: (M+1)⁺=438.1 (RT=7.27 min.)
Step 5

Ethyl 5-(4-benzoyloxy-3-chloro-phenyl)-4-bromo-isoxazole-3-carboxylate

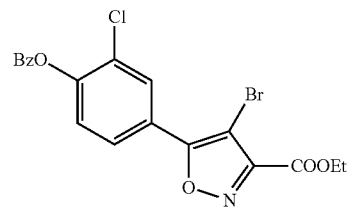

Ethyl 3-(4-benzoyloxy-3-chloro-benzoyl)-3-bromo-3H-azirine-2-carboxylate (68 mg, 0.16 mmol) gave a solid (20 mg) after preparative TLC and crystallisation (EtOH). R$_f$=0.26 (fluorescent) (EtOAc:hexane/1:4). $^1$H NMR (d$_6$-acetone) δ=8.00 (1H, d); 7.90 (1H, dd); 7.50 (1H, d); 7.40 (5H, m); 5.35 (2H, s); 4.45 (2H, q) and 1.40 (3H, t). LCMS: (M+1)$^+$=438.0 (RT=7.39 min.)

Step 6

Ethyl 5-(4-benzyloxy-3-chloro-phenyl)-4-bromo-isoxazole-3-carboxamide

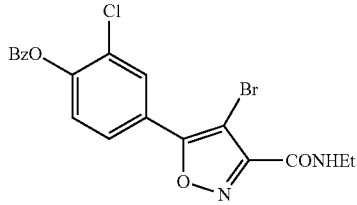

Ethyl 5-(4-benzoyloxy-3-chloro-phenyl)-4-bromo-isoxazole-3-carboxylate (10 mg, 2.3×10$^{-2}$ mmol) gave a crude solid (8 mg). R$_f$=0.53 (EtOAc:hexane/1:2). $^1$H NMR (d$_6$-acetone) δ=8.15 (1H, s, broad); 8.00 (1H, d); 7.90 (1H, dd); 7.50 (1H, d); 7.40 (5H, m); 5.32 (2H, s); 3.42 (2H, q) and 1.20 (3H, t).

Step 7

Ethyl 5-(4-benzyloxy-3-chloro-phenyl)-4-(4-morpholin-4-ylmethyl-phenyl)-isoxazole-3-carboxamide

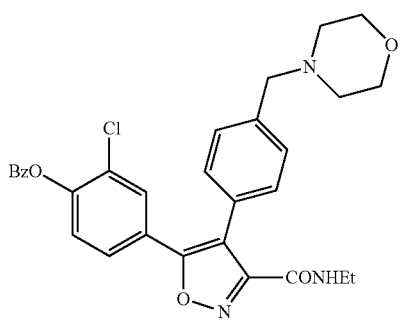

Ethyl 5-(4-benzyloxy-3-chloro-phenyl)-4-bromo-isoxazole-3-carboxamide (10 mg, 2.3×10$^{-2}$ mmol) gave a crude solid (10 mg), which was then used in the next step without any further purification.

Step 8

Ethyl 5-(3-chloro-4-hydroxy-phenyl)-4-(4-morpholin-4-ylmethyl-phenyl)-isoxazole-3-carboxamide

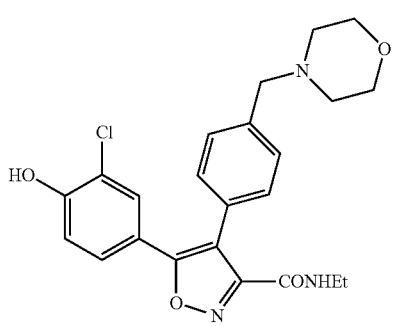

Ethyl 5-(4-benzyloxy-3-chloro-phenyl)-4-(4-morpholin-4-ylmethyl-phenyl)-isoxazole-3-carboxamide (8 mg, 1.5×10$^{-2}$ mmol) gave a crude solid (2 mg) after twice purified by preparative TLC (EtOAc:MeOH/50:1). $^1$H NMR (d$_4$-MeOD) δ=7.70 (2H, d); 7.60 (1H, d); 7.45 (1H+1H, m); 7.00 (2H, d); 3.80 (4H, m); 3.75 (2H, s); 3.50 (2H, q); 2.82 (4H, m) and 1.25 (3H, t). LCMS: (M+1)=442.2 (RT=4.47 min.)

Example 88

3-[4-(4-Bromo-phenyl)-isoxazol-5-yl]-5-chloro-2,6-dihydroxy-benzaldehyde

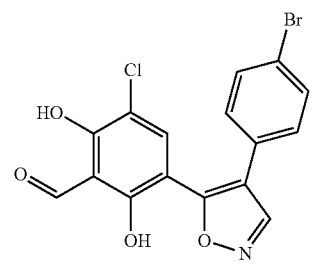 [SMILES: O=Cc1c(O)c(Cl)cc(-c2oncc2-c2ccc(Br)cc2)c1O]

Step 1

3-(4-Bromo-phenyl)-6-chloro-7-hydroxy-4-oxo-4H-chromene-8-carbaldehyde

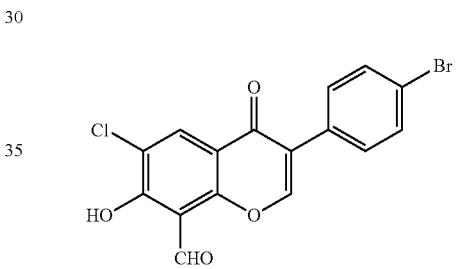

3-(4-Bromo-phenyl)-6-chloro-7-hydroxy-chromen-4-one (0.35 g, 1 mmol) and hexamethylene tetramine (0.14 g, 1 mmol) were dissolved in glacial acetic acid (20 ml) and heated overnight at 100° C. Warm 6M HCl (10 ml) was added and the mixture heated for a further hour before being poured in to water. The precipitate formed was filtered, washed and dried to provide the pure desired product as a pale brown solid.

LCMS (LCQ) t$_R$=8.27, MS m/z 377.3/379.2 [M–H]$^-$

Step 2

3-[4-(4-Bromo-phenyl)-isoxazol-5-yl]-5-chloro-2,6-dihydroxy-benzaldehyde

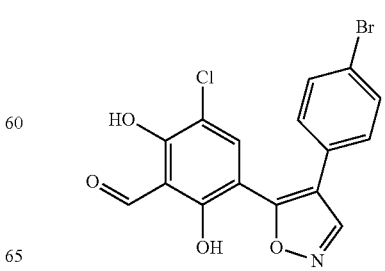

To a solution of 3-(4-bromo-phenyl)-6-chloro-7-hydroxy-4-oxo-4H-chromene-8-carbaldehyde 53.5 mg, 0.14 mmol) in EtOH (6 ml), hydroxylamine hydrochloride (100 mg, 1.4 mmol) was added. The resulting mixture was heated at reflux for 16 hours. EtOH was evaporated and EtOAc (20 ml) was added. The organic layer was washed with sat. NaHCO₃ and dried. Solids (33 mg) were obtained when the resulting oil was triturated with ether. $^1$H NMR (d$_6$-DMSO) δ=9.83 (1H, s); 8.70 (1H, s); 8.21 (1H, s); 7.78 (2H, d) and 7.68 (2H, s). LCMS: (M+1)$^+$=394.1 (RT=8.60 min.)

Example 89

5-(5-Ethyl-2-hydroxy-4-methoxy-phenyl)-4-(4-fluoro-phenyl)-isoxazole-3-carboxylic acid hydroxyamide

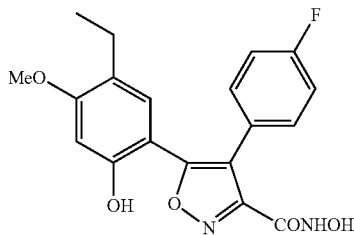

Step 1

1-(5-Ethyl-2,4-dihydroxy-phenyl)-2-(4-fluoro-phenyl)-ethanone

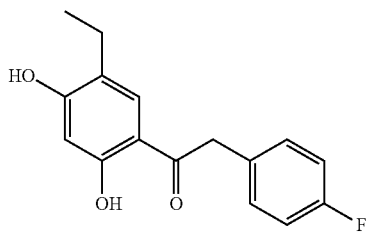 [SMILES: CCc1cc(C(=O)Cc2ccc(F)cc2)c(O)cc1O]

Ethyl resorcinol (5.37 g, 39 mmol) and 4-fluorophenylacetic acid (6.00 g, 39 mmol) were dissolved in etherate BF₃ (40 ml). The solution was heated at 80° C. for 4 hours. When cooled, water (100 ml) was added carefully and the solution was extracted with EtOAc (2×80 ml). The organic layers were then washed with sat. NaHCO₃ (caution) (2×100 ml) and brine (2×100 ml) and dried with Na₂SO₄. After purification with decolourising charcoal, a dark green syrup (10.5 g) was obtained. R$_f$=0.4 (EtOAc:n-hexane/1:3). The compound was used in the next step without further purification. $^1$H NMR (d$_6$-acetone) δ=7.80 (1H, s); 7.35 (2H, m); 7.00 (1H, m); 6.35 (1H, s); 4.35 (2H, s); 2.55 (2H, q) and 1.10 (3H, t).

Step 2

4-(5-Ethyl-2,4-dihydroxy-phenyl)-3-(4-fluoro-phenyl)-2,4-dioxo-butyric acid ethyl ester

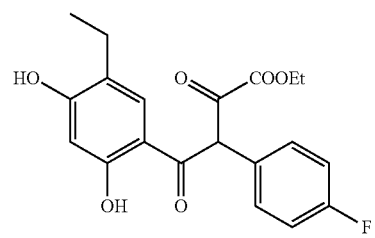 [SMILES: CCOC(=O)C(=O)C(C(=O)c1cc(CC)c(O)cc1O)c1ccc(F)cc1]

To a solution of 1-(5-Ethyl-2,4-dihydroxy-phenyl-2-(4-fluoro-phenyl)-ethanone (10.3 g, 37.6 mmol) in dried pyridine (100 ml) at 0° C., ethyl chlorooxoacetate (15.4 g, 112.8 mmol) was added. The solution was stirred at 0° C. for 4 hours and at room temperature for 16 hours. The aq. layer was neutralised with 1M HCl and extracted with DCM (2×100 ml). The combined DCM layers were then washed with 2M HCl (2×80 ml), sat. NaHCO₃ (1×100 ml), brine (1×100 ml) and dried with Na₂SO₄. After filtration and evaporation of the solvent, dark brown oil was obtained (11.4 g). R$_f$=0.22 (EtOAc:n-hexane/1:2). LCMS shows it is a mixture of desired product [(M−1)$^-$=373.1, RT=7.27) and the cyclised chromene carboxylate [(M−1)$^-$=355.4, RT=7.83) in a ratio of ca. 6:1. A small amount of sample was purified by prep. TLC for spectroscopic analysis. $^1$H NMR (do-acetone) δ=7.75 (1H, s); 7.30 (2H, m); 7.00 (1H, m); 6.45 (1H, s); 4.65 (1H, s); 4.25 (2H, q); 2.55 (2H, q) and 1.10 (6H, t)

Step 3

6-Ethyl-3-(4-fluoro-phenyl)-7-hydroxy-4-oxo-4H-chromene-2-carboxylic acid ethyl ester

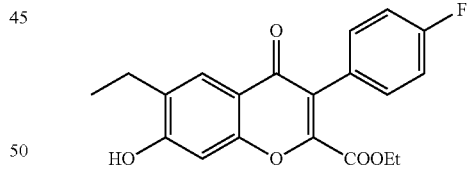

4-(5-Ethyl-2,4-dihydroxy-phenyl)-3-(4-fluoro-phenyl)-2,4-dioxo-butyric acid ethyl ester (3.22 g, 8.6 mmol) was refluxed in a mixture of 0.8M HCl and MeOH (20 ml/20 ml) for 3 hours at 100° C. After that, MeOH was evaporated and the aq. layer was extracted with EtOAc (2×60 ml). The combined organic layers were washed with sat. NaHCO₃ (1×80 ml), brine (2×80 ml), water (1×80 ml) and dried with Na₂SO₄. After purification with decolourising charcoal and evaporation of the solvent, brown sticky solids were obtained. They were then extracted with hot ether, dark yellow solids were obtained (0.26 g). R$_f$=0.43 (EtOAc:n-hexane/1:2). LCMS: (M+1)$^+$=357.3 (RT=7.83). $^1$H NMR (d$_6$-acetone) δ=9.75 (1H, s); 7.80 (1H, s); 7.25 (2H, m); 7.10 (1H, m); 6.90 (1H, s); 4.05 (2H, q); 2.70 (2H, q); 1.20 (3H, t) and 0.95 (3H, t).

Step 4

6-Ethyl-3-(4-fluoro-phenyl)-7-methoxy-4-oxo-4H-chromene-2-carboxylic acid ethyl ester

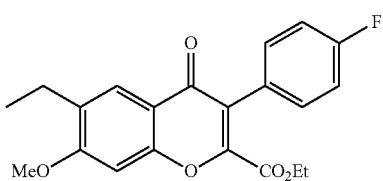 [SMILES: CCOC(=O)c1oc2cc(OC)c(CC)cc2c(=O)c1-c1ccc(F)cc1]

Iodomethane (0.10 ml, 12 equiv.) was added to a solution of 6-Ethyl-3-(4-fluoro-phenyl)-7-hydroxy-4-oxo-4H-chromene-2-carboxylic acid ethyl ester (50 mg, 0.14 mmol) and potassium carbonate (58 mg, 3.0 equiv.) in acetone and the mixture refluxed overnight. The volatiles were then evaporated in vacuo and the residue partitioned between water (15 ml) and EtOAc (15 ml). The organic layer was washed with brine, dried over $MgSO_4$ and evaporated to dryness in vacuo to give a white crystalline product (45 mg, 87% yield)

$\delta_H$ ($CDCl_3$), 7.96 (1H, s, Ar—H), 7.27 (2H, m, Ar—H), 7.12 (2H, m, Ar—H), 6.92 (1H, s, Ar—H), 4.16 (2H, q, $CO_2CH_2CH_3$), 3.95 (3H, s, $OCH_3$), 2.71 (3H, q, $CH_2CH_3$), 1.24 (3H, t, $CO_2CH_2CH_3$), 1.04 (3H, t, $CH_2CH_3$)

Step 5

5-(5-Ethyl-2-hydroxy-4-methoxy-phenyl)-4-(4-fluoro-phenyl)-isoxazole-3-carboxylic acid hydroxyamide

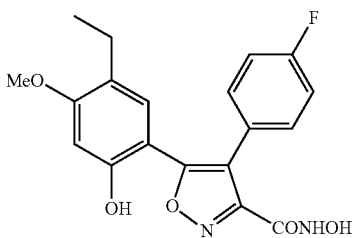

To 6-Ethyl-3-(4-fluoro-phenyl)-7-methoxy-4-oxo-4H-chromene-2-carboxylic acid ethyl ester (25 mg, 0.068 mmol) in ethanol (2.5 ml) was added hydroxylamine (50% in water, 1 ml) and the solution stirred for 48 h. The volatiles were evaporated off in vacuo and the residue purified by preparative TLC (10% MeOH in DCM) to give the desired product as a light brown solid (3 mg, 12% yield).

LCMS (LCT) $t_R$=6.54, MS m/z 373.17 $[M+H]^+$ $\delta_H$ ($d_6$-Acetone), 10.73 (1H, broad s), 8.59 (1H, broad s), 7.39 (2H, m, Ar—H), 7.07 (2H, m, Ar—H), 7.00 (1H, s, Ar—H), 6.55 (1H, s, Ar—H), 3.82 (3H, s, $OCH_3$), 2.48 (2H, q, $CH_2CH_3$), 1.30 (1H, broad s), 1.01 (3H, t, $CH_2CH_3$).

Example 90

5-(5-Ethyl-2,4-dihydroxy-phenyl)-4-(4-fluoro-phenyl)-isoxazole-3-carboxylic acid hydroxyamide

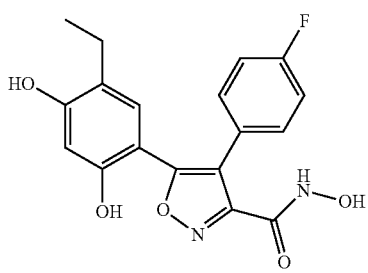 [SMILES: CCc1cc(-c2onc(C(=O)NO)c2-c2ccc(F)cc2)c(O)cc1O]

To 6-Ethyl-3-(4-fluoro-phenyl)-7-hydroxy-4-oxo-4H-chromene-2-carboxylic acid ethyl ester (25 mg, 0.070 mmol) in ethanol (2.5 ml) was added hydroxylamine (50% in water, 1 ml) and the solution stirred for 48 hrs. The volitiles were evaporated off in vacuo and the residue purified by preparative TLC (15% MeOH in DCM) to give the desired product as a brown solid (2 mg, 8% yield).

LCMS (LCT) $t_R$=5.63, MS m/z 359.13 $[M+H]^+$ $\delta_H$ ($d_6$-Acetone), 10.72 (1H, broad s, CONH), 8.69 (1H, broad s, Ar—OH), 8.59 (1H, broad s, Ar—OH), 7.39 (2H, m, Ar—H), 7.06 (2H, m, Ar—H), 6.99 (1H, s, Ar—H), 6.52 (1H, s, Ar—H), 2.49 (2H, q, $CH_2CH_3$), 1.31 (1H, broad s), 1.08 (3H, t, $CH_2CH_3$).

Biological Results

The intrinsic ATPase activity of HSP90 may be measured using yeast HSP90 as a model system. The assay, based on the use of malachite green for the measurement of inorganic phosphate, was used to test the HSP90 inhibitory activity of some of the compounds of the Examples herein.

Malachite Green ATPase Assay

Materials

Chemicals are of the highest purity commercially available and all aqueous solutions are made up in AR water. Because of the need to minimise contamination with inorganic phosphate, precautions should be taken with solutions and apparatus used in the assays. Glassware and pH meters are rinsed with double distilled or deionised water before use and, wherever possible, plastic ware should be used. Gloves are worn for all procedures.

(1) Greiner 384-well (Greiner 781101) or Costar 384-well flat-bottomed polystyrene multiwell plates (VWR).
(2) Assay buffer of (a) 100 mM Tris-HCl, pH 7.4, (b) 150 mM KCl, (c) 6 mM $MgCl_2$. Stored at room temperature.
(3) 0.0812% (w/v) malachite green (M 9636, Sigma Aldrich Ltd., Poole, UK). Stored at room temperature.
(4) 2.32% (w/v) polyvinyl alcohol USP (P 1097, Sigma Aldrich Ltd, Poole, UK) in boiling water (see Comment 1), allowed to cool, and stored at room temperature.
(5) 5.72% (w/v) ammonium molybdate in 6 M hydrochloric acid. Stored at room temperature.
(6) 34% (w/v) sodium citrate. Stored at room temperature.
(7) 100 mM ATP, disodium salt, special quality (47699, Sigma Aldrich). Stored at $-20°$ C.
(8) *E. coli* expressed yeast HSP90 protein, purified >95% (see, e.g., Panaretou et al., 1998) and stored in 50 uL aliquots at $-80°$ C.

Method

1. Dilute test compounds to 500 µM in AR water (DMSO concentration will be 2.5%). Transfer 2.5 µl of these compounds directly from the daughter plate to the assay plate, giving a final assay concentration of 100 µM. To obtain 12 point IC50 values, perform serial dilutions 1:2 to produce a range of assay concentrations from 100 µM to 97.6 nM (2.5% DMSO), and transfer 2.5 µl of each concentration into the assay plate. Column 1 in the assay plate contains no compound, as a negative control. An additional row with no compound is also used as a background.
2. Prepare ATP by diluting 100 mM stock to 925 µM with assay buffer, and aliquot 5 µl of diluted ATP to each well including controls (final assay concentration 370 µM).
3. Add 5 µl of buffer to background row.
4. Dilute enzyme preparation to 1.05 µM with assay buffer, and aliquot 5 µl into each compound well and to the negative control column.
5. Collect the reagents to the bottom of the well, cover plate with plate seal and incubate overnight at 37 deg C.
6. First thing in the morning prepare the Malachite Green Reagent. Add 2 parts of Malachite Green Solution, 1 part of Polyvinyl Alcohol Solution, 1 part of Ammonium Molybdate Solution, and 2 parts of AR water.
7. Invert to mix, and leave for approximately 1 hour until the colour turns from brown to golden yellow.
8. Add 40 µl of Malachite Green Reagent to each well, allow 5 mins for colour to develop.
9. Add 5 µl of Sodium Citrate Reagent to each well (see comment 2)
10. Re-cover with plate seal and shake on plate shaker for at least 15 mins.
11. Measure Absorbance at 620 nM using a suitable plate reader (e.g. Victor, Perkin Elmer Life Sciences, Milton Keynes, UK). Under these conditions, the control absorbance is 0.9 to 1.4, and the background is 0.2-0.35 giving a signal to noise ratio of ~12. The Z' factor calculated from data obtained using these conditions is between 0.6 and 0.9.

Comments (1) The polyvinyl alcohol dissolves in boiling water with difficulty and stirring for 2-3 h is required.
(2) The time interval between addition of the malachite green reagent and the sodium citrate should be kept as short as possible in order to reduce the non-enzymatic hydrolysis of ATP. Once the sodium citrate is added, the colour is stable for up to 4 h at room temperature.
(3) Compounds can be added to the assay plates using a Biomek FX Robot (Beckman Coulter). A Multidrop 384 dispenser (Thermo Labsystems, Basingstoke, UK) can be conveniently used to add reagents to the plate.
(4) The assay conditions were optimised with respect to time, protein and substrate concentration in order to achieve minimal protein concentration whilst retaining signal to noise differential.
(5) Signal to noise (S/N) is calculated using the following equation:

$(S-B)/\sqrt{(SD\ of\ S)^2 + (SD\ of\ B)^2}$ (6) To determine specific activity of HSP90, a range of inorganic phosphate concentrations (0-10 µM) are prepared and the absorbance at 620 nm measured as described. Specific activity is calculated from the resulting calibration curve.

The compounds tested in the above assay were assigned to one of two activity ranges, namely A=<50 µM; B=>50 µM, and those assignments are reported above.

A growth inhibition assay was also employed for the evaluation of candidate HSP90 inhibitors:

Assessment of Cytotoxicity by Sulforhodamine B (SRB) Assay: Calculation of 50% Inhibitory Concentration ($IC_{50}$).

Day 1

1) Determine cell number by haemocytometer.
2) Using an 8 channel multipipettor, add 160 µl of the cell suspension (3600 cells/well or $2\times10^4$ cells/ml) to each well of a 96-well microtitre plate.
3) Incubate overnight at 37° C. in a $CO_2$ incubator.

Day 2

4) Stock solutions of drugs are prepared, and serial dilutions of each drug are performed in medium to give final concentrations in wells.
5) Using a multipipettor, 40 µl of drug (at 5× final concentration) is added to quadruplicate wells.
6) Control wells are at either side of the 96 well plates, where 40 µl of medium is added.
7) Incubate plates in $CO_2$ incubator for 4 days (48 hours).

Day 6

8) Tip off medium into sink and immerse plate slowly into 10% ice cold trichloroacetic acid (TCA). Leave for about 30 mins on ice.
9) Wash plates three times in tap water by immersing the plates into baths of tap water and tipping it off.
10) Dry in incubator.
11) Add 100 µl of 0.4% SRB in 1% acetic acid to each well (except the last row (right hand) of the 96 well plate, this is the 0% control, ie no drug, no stain. The first row will be the 100% control with no drug, but with stain). Leave for 15 mins.
12) Wash off unbound SRB stain with four washes of 1% acetic acid.
13) Dry plates in incubator.
14) Solubilise SRB using 100 µl of 10 mM Tris base and put plates on plate shaker for 5 mins.
15) Determine absorbance at 540 nm using a plate reader. Calculate mean absorbance for quadruplicate wells and express as a percentage of value for control, untreated wells.
16) Plot % absorbance values versus log drug concentration and determine the $IC_{50}$.

By way of illustration, the compound of Example 2 gave an IC50 in the 'A' range (<50 uM) for the SRB growth arrest assay.

A Fluorescence Polarization_Assay was also Employed for the Evaluation of some of the Compounds of the Examples Fluorescence Polarization Assay Fluorescence polarization {also known as fluorescence anisotropy} measures the rotation of a fluorescing species in solution, where the larger molecule the more polarized the fluorescence emission.

When the fluorophore is excited with polarized light, the emitted light is also polarized. The molecular size is proportional to the polarization of the fluorescence emission.

The fluoroscein-labelled probe—RBT0045864-FAM-

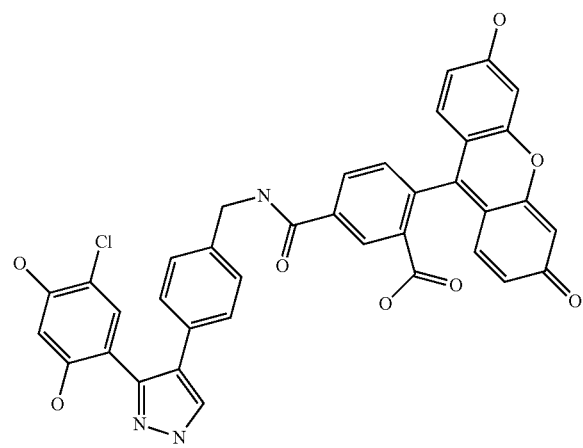 [SMILES: O=C(NCc1ccc(-c2c[nH]nc2-c2cc(Cl)c(O)cc2O)cc1)c1ccc(-c2c3ccc(=O)cc-3oc3cc(O)ccc23)c(C(=O)O)c1]

binds to HSP90 {full-length human, full-length yeast or N-terminal domain HSP90} and the anisotropy {rotation of the probe:protein complex} is measured.

Test compound is added to the assay plate, left to equilibrate and the anisotropy measured again. Any change in anisotropy is due to competitive binding of compound to HSP90, thereby releasing probe.

Materials

Chemicals are of the highest purity commercially available and all aqueous solutions are made up in AR water.
1) Costar 96-well black assay plate #3915
2) Assay buffer of (a) 100 mM Tris pH7.4; (b) 20 mM KCl; (c) 6 mM $MgCl_2$. Stored at room temperature.
3) BSA (bovine serum albumen) 10 mg/ml (New England Biolabs #B9001S)
4) 20 mM probe in 100% DMSO stock concentration. Stored in the dark at RT. Working concentration is 200 nM diluted in AR water and stored at 4° C. Final concentration in assay 80 nM.
5) E. coli expressed human full-length HSP90 protein, purified >95% (see, e.g., Panaretou et al., 1998) and stored in 50 µL aliquots at −80° C.

Protocol
1) Add 100 µl 1× buffer to wells 11A and 12A (=FP BLNK)
2) Prepare assay mix—all reagents are kept on ice with a lid on the bucket as the probe is light-sensitive.

|  | i. | Final Conc" |
|---|---|---|
| 1× Hsp90 FP Buffer | 10 ml | 1× |
| BSA 10 mg/ml (NEB) | 5.0 µl | 5 µg/ml |
| Probe 200 µM | 4.0 µl | 80 nM |
| Human full-length Hsp90 | 6.25 µl | 200 nM |

3) Aliquot 100 µl assay mix to all other wells
4) Seal plate and leave in dark at room temp for 20 minutes to equilibrate Compound Dilution Plate—1×3 dilution series
1) In a clear 96-well v-bottom plate—{#VWR 007/008/257} add 10 µl 100% DMSO to wells B1 to H11
2) To wells A1 to A11 add 17.5 µl 100% DMSO
3) Add 2.5 µl cpd to A1. This gives 2.5 mM {50×} stock cpd—assuming cpds 20 mM.
4) Repeat for wells A2 to A10. Control in columns 11 and 12.
5) Transfer 5 µl from row A to row B—not column 12. Mix well.
6) Transfer 5 µl from row B to row C. Mix well.
7) Repeat to row G.
8) Do not add any compound to row H—this is the 0 row.
9) This produces a 1×3 dilution series from 50 µM to 0.07 µM.
10) In well B12 prepare 20 µl of 100 µM standard compound.
11) After first incubation the assay plate is read on a Fusion™ a-FP plate reader (Packard BioScience, Pangbourne, Berkshire, UK).
12) After the first read, 2 µl of diluted compound is added to each well for columns 1 to 10. In column 11 {provides standard curve} only add compound B11-H11. Add 2 µl of 100 mM standard cpd to wells B12-H12 {is positive control}
13) The Z' factor is calculated from zero controls and positive wells. It typically gives a value of 0.7-0.9.

The compounds tested in the above assay were assigned to one of two activity ranges, namely A=<10 µM; B=>10 µM, and those assignments are reported above. By way of illustration, the compound of Example 2 gave an IC50 in the 'A' range.

REFERENCES

A number of publications are cited above in order to more fully describe and disclose the invention and the state of the art to which the invention pertains. Full citations for these references are provided below. Each of these references is incorporated herein by reference in its entirety into the present disclosure.

Argon Y and Simen B B. 1999 "Grp94, an ER chaperone with protein and peptide binding properties", *Semin. Cell Dev. Biol.*, Vol. 10, pp. 495-505.

Bijlmakers M-J J E, Marsh M. 2000 "Hsp90 is essential for the synthesis and subsequent membrane association, but not the maintenance, of the Src-kinase p56Ick", *Molecular Biology of the Cell*, Vol. 11(5), pp. 1585-1595.

Bucci M; Roviezzo F; Cicala C; Sessa W C, Cirino G. 2000 "Geldanamycin, an inhibitor of heat shock protein 90 (Hsp90) mediated signal transduction has anti-inflammatory effects and interacts with glucocorticoid receptor in vivo", *Brit. J. Pharmacol.*, Vol 131(1), pp. 13-16.

Chen C-F, Chen Y, Dai K D, Chen P-L, Riley D J and Lee W-H. 1996 "A new member of the hsp90 family of molecular chaperones interacts with the retinoblastoma protein during mitosis and after heat shock", *Mol. Cell. Biol.*, Vol. 16, pp. 4691-4699.

Chiosis G, Timaul M N, Lucas B, Munster P N, Zheng F F, Sepp-Lozenzino L and Rosen N. 2001 "A small molecule designed to bind to the adenine nucleotide pocket of HSP90 causes Her2 degradation and the growth arrest and differentiation of breast cancer cells", *Chem. Biol.*, Vol. 8, pp. 289-299.

Conroy S E and Latchman D S. 1996 "Do heat shock proteins have a role in breast cancer?", *Brit. J. Cancer*, Vol. 74, pp. 717-721.

Felts S J, Owen B A L, Nguyen P, Trepel J, Donner D B and Toft D O. 2000 "The HSP90-related protein TRAP1 is a mitochondrial protein with distinct functional properties", *J. Biol. Chem.*, Vol. 5, pp. 3305-3312.

Fuller W, Cuthbert A W. 2000 "Post-translational disruption of the delta F508 cystic fibrosis transmembrane conductance regulator (CFTR)-molecular Chaperone complex with geldanamycin stabilizes delta F508 CFTR in the rabbit reticulocyte lysate", *J. Biol. Chem.*; Vol 275(48), pp. 37462-37468.

Hickey E, Brandon S E, Smale G, Lloyd D and Weber L A. 1999 "Sequence and regulation of a gene encoding a human 89-kilodalton heat shock protein", *Mol. Cell. Biol.*, Vol. 9, pp. 2615-2626.

Hoang A T, Huang J, Rudra-Gonguly N, Zheng J, Powell W C, Rabindron S K, Wu C and Roy-Burman P. 2000 "A novel association between the human heat shock transcription factor I (HSF1) and prostate adenocarcinoma, *Am. J. Pathol.*, Vol. 156, pp. 857-864.

Hostein I, Robertson D, Di Stefano F, Workman P and Clarke P A. 2001 "Inhibition of signal transduction by the HSP90 inhibitor 17-allylamino-17-demethoxygeldanamycin results in cytostasis and apoptosis", *Cancer Res.*, Vol. 61, pp. 4003-4009.

Hur E, Kim H—H, Choi S M, Kim J H, Yim S, Kwon H J, Choi Y, Kim D K, Lee M-O, Park H. 2002 "Reduction of hypoxia-induced transcription through the repression of hypoxia-inducible factor-1α/aryl hydrocarbon receptor nuclear translocator DNA binding by the 90-kDa heat-shock protein inhibitor radicicol", *Mol. Pharmacol.*, Vol 62(5), pp. 975-982.

Hutter et al, 1996, *Circulation*, Vol. 94, pp. 1408.

Jameel A, Skilton R A, Campbell T A, Chander S K, Coombes R C and Luqmani Y A. 1992 "Clinical and biological significance of HSP89a in human breast cancer", *Int. J. Cancer*, Vol. 50, pp. 409-415.

Jolly C and Morimoto R I. 2000 "Role of the heat shock response and molecular chaperones in oncogenesis and cell death", *J. Natl. Cancer Inst.*, Vol. 92, pp. 1564-1572.

Kawanishi K, Shiozaki H, Doki Y, Sakita I, Inoue M, Yano M, Tsujinata T, Shamma A and Monden M. 1999 "Prognostic significance of heat shock proteins 27 and 70 in patients with squamous cell carcinoma of the esophagus", *Cancer*, Vol. 85, pp. 1649-1657.

Kelland L R, Abel G, McKeage M J, Jones M, Goddard P M, Valenti M, Murrer B A and Harrap K R. 1993 "Preclinical antitumour evaluation of bis-acetalo-amino-dichloro-cyclohexylamine platinum (IV): an orally active platinum drug", *Cancer Research*, Vol. 53, pp. 2581-2586.

Kelland L R, Sharp S Y, Rogers P M, Myers T G and Workman P. 1999 "DT-diaphorase expression and tumor cell sensitivity to 17-allylamino, 17-demethoxygeldanamycin, an inhibitor of heat shock protein 90", *J. Natl. Cancer Inst.*, Vol. 91, pp. 1940-1949.

Kurebayashi J, Otsuki T, Kurosumi M, Soga S, Akinaga S, Sonoo, H. 2001 "A radicicol derivative, KF58333, inhibits expression of hypoxia-inducible factor-1α and vascular endothelial growth factor, angiogenesis and growth of human breast cancer xenografts", *Jap. J. Cancer Res.*, Vol 92(12), 1342-1351.

Kwon H J, Yoshida M, Abe K, Horinouchi S and Bepple T. 1992 "Radicicol, an agent inducing the reversal of transformed phentoype of src-transformed fibroblasts, *Biosci., Biotechnol., Biochem., Vol.* 56, pp. 538-539.

Lebeau J, Le Cholony C, Prosperi M T and Goubin G. 1991 "Constitutive overexpression of 89 kDa heat shock protein gene in the HBL100 mammary cell line converted to a tumorigenic phenotype by the EJ/T24 Harvey-ras oncogene", *Oncogene*, Vol. 6, pp. 1125-1132.

Marcu M G, Chadli A, Bouhouche I, Catelli M and Neckers L. 2000a "The heat shock protein 90 antagonist novobiocin interacts with a previously unrecognized ATP-binding domain in the carboxyl terminus of the chaperone", *J. Biol. Chem.*, Vol. 275, pp. 37181-37186.

Marcu M G, Schulte T W and Neckers L. 2000b "Novobiocin and related coumarins and depletion of heat shock protein 90-dependent signaling proteins", *J. Natl. Cancer Inst.*, Vol. 92, pp. 242-248.

Martin K J, Kritzman B M, Price L M, Koh B, Kwan C P, Zhang X, MacKay A, O'Hare M J, Kaelin C M, Mutter G L, Pardee A B and Sager R. 2000 "Linking gene expression patterns to therapeutic groups in breast cancer", *Cancer Res.*, Vol. 60, pp. 2232-2238.

Neckers L, Schulte T W and Momnaaugh E. 1999 "Geldanamycin as a potential anti-cancer agent: its molecular target and biochemical activity", *Invest. New Drugs*, Vol. 17, pp. 361-373.

Page J, Heath J, Fulton R, Yalkowsky E, Tabibi E, Tomaszewski J, Smith A and Rodman L. 1997 "Comparison of geldanamycin (NSC-122750) and 17-allylaminogeldanamycin (NSC-330507D) toxicity in rats", *Proc. Am. Assoc. Cancer Res.*, Vol. 38, pp. 308.

Panaretou B, Prodromou C, Roe S M, O'Brien R, Ladbury J E, Piper P W and Pearl L H. 1998 "ATP binding and hydrolysis are essential to the function of the HSP90 molecular chaperone in vivo", *EMBO J., Vol.* 17, pp. 4829-4836.

Plumier et al, 1997, *Cell. Stress Chap.*, Vol. 2, pp. 162

Pratt W B. 1997 "The role of the HSP90-based chaperone system in signal transduction by nuclear receptors and receptors signalling via MAP kinase", *Annu. Rev. Pharmacol. Toxicol.*, Vol. 37, pp. 297-326.

Prodromou C and Pearl L H. 2000a "Structure and in vivo function of HSP90", *Curr. Opin. Struct. Biol.*, Vol. 10, pp. 46-51.

Prodromou C, Roe S M, O'Brien R, Ladbury J E, Piper P W and Pearl L H. 1997 "Identification and structural characterization of the ATP/ADP-binding site in the HSP90 molecular chaperone", *Cell*, Vol. 90, pp. 65-75.

Prodromou C, Panaretou B, Chohan S, Siligardi G, O'Brien R, Ladbury J E, Roe S M, Piper P W and Pearl L H. 2000b "The ATPase cycle of HSP90 drives a molecular 'clamp' via transient dimerization of the N-terminal domains", *EMBO J.*, Vol. 19, pp. 4383-4392.

Rajder et al, 2000, *Ann. Neurol.*, Vol. 47, pp. 782.

Roe S M, Prodromou C, O'Brien R, Ladbury J E, Piper P W and Pearl L H. 1999 "Structural basis for inhibition of the HSP90 molecular chaperone by the antitumour antibiotics radicicol and geldanamycin", *J. Med. Chem.*, Vol. 42, pp. 260-266.

Rutherford S L and Lindquist S. 1998 "HSP90 as a capacitor for morphological evolution. *Nature*, Vol. 396, pp. 336-342.

Schulte T W, Akinaga S, Murakata T, Agatsuma T, Sugimoto S, Nakano H, Lee Y S, Simen B B, Argon Y, Felts S, Toft D O, Neckers L M and Sharma S V. 1999 "Interaction of radicicol with members of the heat shock protein 90 family of molecular chaperones", *Mol. Endocrinology*, Vol. 13, pp. 1435-1448.

Schulte T W, Akinaga S, Soga S, Sullivan W, Sensgard B, Toft D and Neckers L M. 1998 "Antibiotic radicicol binds to the N-terminal domain of HSP90 and shares important biologic activities with geldanamcyin", *Cell Stress and Chaperones*, Vol. 3, pp. 100-108.

Schulte T W and Neckers L M. 1998 "The benzoquinone ansamycin 17-allylamino-17-deemthoxygeldanamcyin binds to HSP90 and shares important biologic activities with geldanamycin", *Cancer Chemother. Pharmacol.*, Vol. 42, pp. 273-279.

Sittler et al, 2001, *Hum. Mol. Genet.*, Vol. 10, pp. 1307.

Smith D F. 2001 "Chaperones in signal transduction", in: *Molecular chaperones in the cell* (P Lund, ed.; Oxford University Press, Oxford and NY), pp. 165-178.

Smith D F, Whitesell L and Katsanis E. 1998 "Molecular chaperones: Biology and prospects for pharmacological intervention", *Pharmacological Reviews*, Vol. 50, pp. 493-513.

Song H Y, Dunbar J D, Zhang Y X, Guo D and Donner D B. 1995 "Identification of a protein with homology to hsp90 that binds the type 1 tumour necrosis factor receptor", *J. Biol. Chem.*, Vol. 270, pp. 3574-3581.

Stebbins C E, Russo A, Schneider C, Rosen N, Hartl F U and Pavletich N P. 1997 "Crystal structure of an HSP90-geldanamcyin complex: targeting of a protein chaperone by an antitumor agent", *Cell*, Vol. 89, pp. 239-250.

Supko J G, Hickman R L, Grever M R and Malspeis L. 1995 "Preclinical pharmacologic evaluation of geldanamycin as an antitumour agent", *Cancer Chemother. Pharmacol.*, Vol. 36, pp. 305-315.

Tratzelt et al, 1995, *Proc. Nat. Acad. Sci.*, Vol. 92, pp. 2944.

Trost et al, 1998, *J. Clin. Invest.*, Vol. 101, pp. 855.

Tytell M and Hooper P L. 2001 "Heat shock proteins: new keys to the development of cytoprotective therapies", *Emerging Therapeutic Targets*, Vol. 5, pp. 267-287.

Uehara U, Hori M, Takeuchi T and Umezawa H. 1986 "Phenotypic change from transformed to normal induced by benzoquinoid ansamycins accompanies inactivation of p60src in rat kidney cells infected with Rous sarcoma virus", *Mol. Cell. Biol.*, Vol. 6, pp. 2198-2206.

Waxman, Lloyd H. Inhibiting hepatitis C virus processing and replication. (Merck & Co., Inc., USA). PCT Int. Appl. (2002), WO 0207761

Winklhofer et al, 2001, *J. Biol. Chem.*, Vol. 276, 45160.

Whitesell L, Mimnaugh E G, De Costa B, Myers C E and Neckers L M. 1994 "Inhibition of heat shock protein HSP90-pp60v-src heteroprotein complex formation by benzoquinone ansamycins: essential role for stress proteins in oncogenic transformation", *Proc. Natl. Acad. Sci. U S A.*, Vol. 91, pp. 8324-8328.

Yorgin et al. 2000 "Effects of geldanamycin, a heat-shock protein 90-binding agent, on T cell function and T cell nonreceptor protein tyrosine kinases", *J. Immunol.*, Vol 164(6), pp. 2915-2923.

Young J C, Moarefi I and Hartl F U. 2001 "HSP90: a specialized but essential protein-folding tool", *J. Cell. Biol.*, Vol. 154, pp. 267-273.

Zhao J F, Nakano H and Sharma S. 1995 "Suppression of RAS and MOS transformation by radicicol", *Oncogene*, Vol. 11, pp. 161-173.

The invention claimed is:

1. A method of inhibiting Heat Shock Protein 90 (HSP90) activity in mammals comprising administering to the mammal an amount of a compound of formula (A) or (B) or a salt, N-oxide, hydrate or solvate thereof, or a prodrug thereof effective to inhibit HSP90 activity:

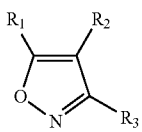

(A)

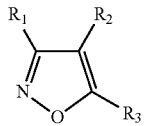

(B)

wherein $R_1$ is a group of formula (IB)

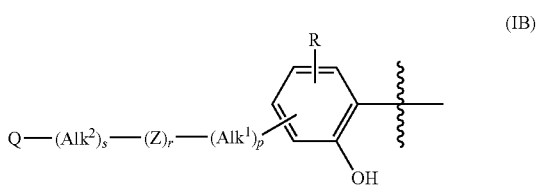

(IB)

wherein in any compatible combination

R represents one or more optional substituents, $Alk^1$ and $Alk^2$ are optionally substituted divalent $C_1$-$C_6$ alkylene or $C_2$-$C_6$ alkenylene radicals, p, r and s are independently 0 or 1, Z is —O—, —S—, —(C=O)—, —(C=S)—, —SO$_2$—, —C(=O )O—, —C(=O )NR$^A$—, —C(=S)NR$^A$—, —SO$_2$NR$^A$—, —NR$^A$C(=O)—, —NR$^A$SO$_2$— or NR$^A$— wherein R$^A$ is hydrogen or $C_1$-$C_6$ alkyl, and Q is hydrogen or an optionally substituted carbocyclic or heterocyclic radical;

$R_2$ is (i) a group of formula (IA):

—Ar$^1$ -(Alk$^1$)$_p$-(Z)$_r$-(Alk$^2$)$_s$-Q  (IA)

wherein in any compatible combination

Ar$^1$ is an optionally substituted aryl or heteroaryl radical, and

Alk$^1$, Alk$^2$, p, r, s, Z, R$^A$ and Q are as defined in relation to $R_1$;

(ii) a carboxamide radical; or (iii) a non aromatic carbocyclic or heterocyclic ring wherein a ring carbon is optionally substituted, and/or a ring nitrogen is optionally substituted by a group of formula —(Alk$^1$)$_p$-(Z)$_r$-(Alk$^2$)$_s$-Q wherein Q, Alk$^1$, Alk$^2$, Z, p, r and s are as defined above in relation to group (IA); and $R_3$ is hydrogen, optionally substituted cycloalkyl, cycloalkenyl, $C_1$-$C_6$ alkyl, $C_1$-$C_6$ alkenyl, or $C_1$-$C_6$ alkynyl; or a carboxyl, carboxamide, or carboxyl ester group.

2. The method as claimed in claim 1 wherein the compound has formula (ID) or the formula B regioisomer thereof,

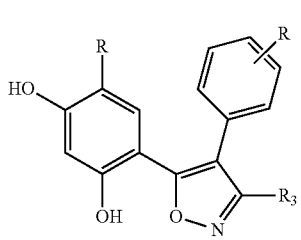

(ID)

wherein each R independently represents an optional substituent and $R^3$ represents a carboxamide group.

3. The method as claimed in claim 1 wherein the compound has formula (IE) or the formula B regioisomer thereof,

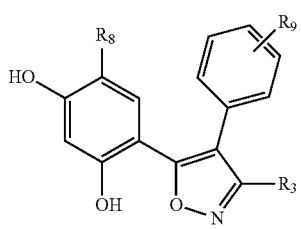
(IE)

wherein $R_3$ represents a carboxamide group; $R_9$ represents —$CH_2NR^{10}R^{11}$ or —$NR^{10}R^{11}$ wherein the substituted amino group —$NR^{10}R^{11}$ is a solubilising group; and $R_8$ represents an optional substituent.

4. The method as claimed in claim 1 wherein the compound is selected from:
- 5-(2,4-Dihydroxy-5-isopropyl-phenyl)-4-(4-morpholin-4-ylmethyl-phenyl)-isoxazole-3-carboxylic acid ethylamide
- 5-(2,4-Dihydroxy-5-isopropyl-phenyl)-4-(4-piperidin-1-ylmethyl-phenyl)-isoxazole-3-carboxylic acid ethylamide
- 4-(4-Diethylaminomethyl-phenyl)-5-(2,4-dihydroxy-5-isopropyl-phenyl)-isoxazole-3-carboxylic acid ethylamide
- 5-(2,4-Dihydroxy- 5-isopropyl-phenyl)-4- [4-(4-methyl-piperazin- 1 -ylmethyl)-phenyl]- isoxazole-3-carboxylic acid ethylamide
- 5-(2,4-Dihydroxy-5 -isopropyl-phenyl)-4-(4-ethylaminomethyl-phenyl)-isoxazole-3 -carboxylic acid ethylamide
- 5-(2,4-Dihydroxy-5-isopropyl-phenyl)-4-[4-(isopropylamino-methyl)-phenyl]-isoxazole-3-carboxylic acid ethylamide
- 4-(4-Cyclohexylaminomethyl-phenyl)-5-(2,4-dihydroxy-5 -isopropyl-phenyl)-isoxazole-3 -carboxylic acid ethylamide
- 4-[4-(tert-Butylamino-methyl)-phenyl]-5-(2,4-dihydroxy-5-isopropyl-phenyl)-isoxazole-3-carboxylic acid ethylamide
- 5-(2,4-Dihydroxy-5-isopropyl-phenyl)-4-{4-[(2-methoxy-ethylamino)-methyl]-phenyl}-isoxazole-3-carboxylic acid ethylamide
- 5 -(2,4-Dihydroxy-5-isopropyl-phenyl)-4-(4-morpholin-4-ylmethyl-phenyl)-isoxazole-3 -carboxylic acid isopropylamide
- 5-(2,4-Dihydroxy-5-isopropyl-phenyl)-4-[4-(4-methyl-piperazin-1-ylmethyl)-phenyl]-isoxazole-3-carboxylic acid isopropylamide
- 5-(5-tert-Butyl-2,4-dihydroxy-phenyl)-4-[4-(4-methyl-piperazin-1-ylmethyl)-phenyl]-isoxazole-3-carboxylic acid ethylamide
- 5-(5-tert-Butyl-2,4-dihydroxy-phenyl)-4-(4-piperidin-1-ylmethyl-phenyl)-isoxazole-3-carboxylic acid ethylamide
- 5-(2,4-Dihydroxy-5-isobutyl-phenyl)-4-(4-morpholin-4-ylmethyl-phenyl)-isoxazole-3-carboxylic acid ethylamide
- 5-(2,4-Dihydroxy-5-isobutyl-phenyl)-4-(4-piperidin-1-ylmethyl-phenyl)-isoxazole-3-carboxylic acid ethylamide
- 5-(5-tert-Butyl-2,4-dihydroxy-phenyl)-4-(4-morpholin-4-ylmethyl-phenyl)-isoxazole-3-carboxylic acid ethylamide
- 5-(5-tert-Butyl-2,4-dihydroxy-phenyl)-4-(4-diethylaminomethyl-phenyl)-isoxazole-3-carboxylic acid ethylamide
- 3-(5-Chloro-2,4-dihydroxy-phenyl)-4-(4-morpholin-4-ylmethyl-phenyl)-isoxazole-5-carboxylic acid ethylamide
- 4-(4-Diethylaminomethyl-phenyl)-5-(4,6-dihydroxy-2'-methyl-biphenyl-3-yl)-isoxazole-3-carboxylic acid ethylamide
- 4-(4-Diethylaminomethyl-phenyl)-5-(4'-fluoro-4,6-dihydroxy-biphenyl-3-yl)-isoxazole-3-carboxylic acid ethylamide
- 4-(4-Diethylaminomethyl-phenyl)-5-(4,6-dihydroxy-biphenyl-3-yl)-isoxazole-3-carboxylic acid ethylamide
- 5-(2'-Fluoro-4,6-dihydroxy-biphenyl-3-yl)-4-(4-pyrrolidin-1-ylmethyl-phenyl)-isoxazole-3-carboxylic acid ethylamide
- 5-(4,6-Dihydroxy-biphenyl-3-yl)-4-(4-morpholin-4-ylmethyl-phenyl)-isoxazole-3-carboxylic acid ethylamide
- 5-(2,4-Dihydroxy-5-phenethyl-phenyl)-4-(4-morpholin-4-ylmethyl-phenyl)-isoxazole-3-carboxylic acid ethylamide
- 5-(5-Chloro-2,4-dihydroxy-phenyl)-4-(4-piperidin-1-ylmethyl-phenyl)-isoxazole-3-carboxylic acid isopropylamide
- 4-(4-Diethylaminomethyl-phenyl)-5-(5-ethyl-2,4-dihydroxy-phenyl)-isoxazole-3-carboxylic acid ethylamide
- 5-(5-Ethyl-2,4-dihydroxy-phenyl)-4-[4-(4-methyl-piperazin-1-ylmethyl)-phenyl]-isoxazole-3-carboxylic acid ethylamide
- 5 -(5-Ethyl-2,4-dihydroxy-phenyl)-4-(4-morpholin-4-ylmethyl-phenyl)-isoxazole-3 -carboxylic acid ethylamide
- 5 -(5 -Chloro-2,4-dihydroxy-phenyl)-4-(4-diethylaminomethyl-phenyl)-isoxazole-3 -carboxylic acid ethylamide
- 5-(5-Chloro-2,4-dihydroxy-phenyl)-4-[4-(4-methyl-piperazin-1-ylmethyl)-phenyl]-isoxazole-3-carboxylic acid ethylamide
- 5-(5 -Chloro-2,4-dihydroxy-phenyl)-4-(4-morpholin-4-ylmethyl-phenyl)-isoxazole-3 -carboxylic acid ethylamide and salts, hydrates, solvates and prodrugs thereof.

5. The method as claimed in claim 1 wherein the radical $Ar^1$ present in $R_1$ has formula (1B)

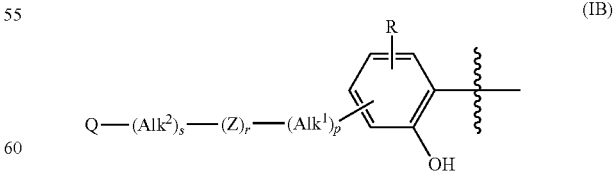
(IB)

wherein $Alk^1$, $Alk^2$, p, r, s, Z and Q are as defined in claim 1, and R represents one or more optional substituents.

6. The method as claimed in claim 5 wherein that the ring carbon atom adjacent the hydroxyl group in radical (IB) is unsubstituted.

7. The method as claimed in claim 1 wherein, in $R_1$, each of p, r, and s is 0, and Q is hydrogen.

8. The method as claimed in claim 7 wherein $R_1$ is optionally substituted phenyl.

9. The method as claimed in claim 7 wherein $R_1$ is 2-hydroxyphenyl, optionally further substituted by one or more of hydroxy, methyl, ethyl, methoxy, ethoxy, chloro, or bromo.

10. The method as claimed in claim 7 wherein $R_1$ is 2,4-dihydroxyphenyl, substituted in the 5-position by a small lipophilic substituent.

11. The method as claimed in claim 10 wherein the small lipophilic substituent methyl, ethyl, isopropyl, isobutyl, tert-butyl, chloro, or bromo.

12. The method as claimed in claim 10 wherein the hydroxyl groups in $R_1$ are protected by groups which are cleaved in the body to release the hydroxyl groups.

13. The method as claimed in claim 12 wherein the protecting groups are methylcarbonyloxy, or isopropylamino-carbonyloxy.

14. The method as claimed in claim 1 wherein, in $R_1$, p, r and s are each 0, and Q is an optionally substituted carbocyclic or heterocyclic ring.

15. The method as claimed in claim 14 wherein Q is an optionally substituted phenyl or pyridyl ring.

16. The method as claimed in claim 1 wherein, in $R_1$, p and/or s are each 1 and r is 0.

17. The method as claimed in claim 1 wherein, in $R_1$, each of p, r, and s is 1.

18. The method as claimed in claim 1 wherein, in $R_1$, p and s are each 0 and r is 1.

19. The method as claimed in claim 1 wherein $R_2$ is a group of formula (1A).

20. The method as claimed in claim 19 wherein $R_2$ is optionally substituted 2-, 3-, or 4-pyridyl, 2- or 3-furanyl, 2- or 3-thienyl, or thiazolyl.

21. The method as claimed in claim 20 wherein optional substituents present in $R_2$ are selected from methoxy, ethoxy, methylenedioxy, ethylenedioxy, fluoro, chloro, bromo, and trifluoromethyl.

22. The method as claimed in claim 19 wherein $R_2$ is phenyl substituted in the 4 position by methoxy, ethoxy, fluoro, chloro, bromo, piperazinyl, N-methylpiperazinyl, or piperidinyl.

23. The method as claimed in claim 1 wherein $R_2$ has the partial structure:

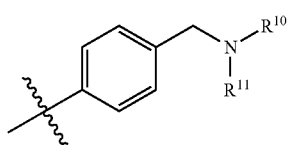

wherein the substituted amino group —$NR^{10}R^{11}$ is a solubilising group.

24. The method as claimed in claim 23 wherein the solubilising group is selected from morpholinyl, piperidinyl, piperazinyl, pyrrolidinyl, ethylamino, isopropylamino, diethylamine, cyclohexylamino, cyclopentylamino, methoxyethylamino, piperidin-4-yl, N-acetylpiperazinyl, methylsulfonylamino, thiomorpholinyl, thiomorpholinyldioxide, 4-hydroxyethylpiperidinyl, and 4-hydroxypiperidinyl.

25. The method as claimed in claim 1 wherein $R_2$ is a carboxamide group of formula —$CONR^B(Alk)_nR^A$ wherein
Alk is a divalent alkylene, alkenylene or alkynylene radical, and the Alk radical may be optionally substituted,
n is 0 or 1,
$R^B$ is hydrogen or a $C_1$-$C_6$ alkyl or $C_2$-$C_6$ alkenyl group,
$R^A$ is hydroxy or optionally substituted carbocyclic; or heterocyclyl, in which heterocyclic rings may be substituted,
or $R^A$ and $R^B$ taken together with the nitrogen to which they are attached form an N-heterocyclic ring which may optionally contain one or more additional hetero atoms selected from O, S and N, and which may optionally be substituted on one or more ring C or N atoms.

26. The method as claimed in claim 1 wherein $R_3$ is hydrogen, methyl, ethyl, n- or iso-propyl, trifluoromethyl, hydroxyethyl, methylsulfonaminomethyl, or a carboxamide group —$CONR^B(Alk)_nR^A$ as defined in claim 25.

27. The method as claimed in claim 1 wherein $R_3$ is ethylaminocarbonyl or isopropylaminocarbonyl.

28. The method as claimed in claim 1 wherein the compound has formula (ID) or the formula B regioisomer thereof,

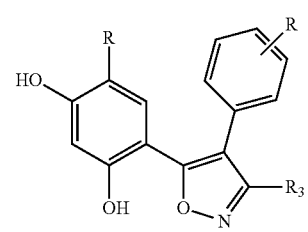

wherein each R independently represents an optional substituent and $R_3$ represents a carboxamide group.

29. The method as claimed in claim 1 wherein the compound has formula (IE) or the formula B regioisomer thereof,

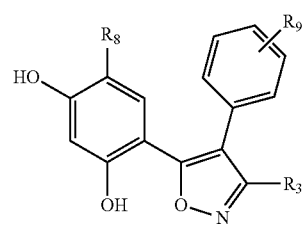

wherein $R_3$ represents a carboxamide group; $R_9$ represents —$CH_2NR^{10}R^{11}$ or $NR^{10}R^{11}$ wherein the substituted amino group —$NR^{10}R^{11}$ is a solubilising group; and $R_8$ represents an optional substituent.

* * * * *